(12) United States Patent
Kaufman et al.

(10) Patent No.: US 9,616,209 B2
(45) Date of Patent: Apr. 11, 2017

(54) DISPENSING APPLICATOR FOR FLUIDS

(71) Applicant: BIOMED PACKAGING SYSTEMS INC., Norwalk, CT (US)

(72) Inventors: Jack W. Kaufman, Los Angeles, CA (US); James Brown, Armonk, NY (US)

(73) Assignee: BIOMED PACKAGING SYSTEMS INC., Norwalk, CT (US)

( * ) Notice: Subject to any disclaimer, the term of this patent is extended or adjusted under 35 U.S.C. 154(b) by 231 days.

(21) Appl. No.: 14/068,905

(22) Filed: Oct. 31, 2013

(65) Prior Publication Data

US 2014/0126949 A1    May 8, 2014

Related U.S. Application Data

(63) Continuation of application No. 13/601,755, filed on Aug. 31, 2012, now Pat. No. 9,220,881, which is a
(Continued)

(51) Int. Cl.
  *B43K 5/14*       (2006.01)
  *A61F 13/40*      (2006.01)
  (Continued)

(52) U.S. Cl.
  CPC ........... *A61M 35/006* (2013.01); *A45D 34/04* (2013.01); *A61L 2/00* (2013.01); *A61L 2/18* (2013.01);
  (Continued)

(58) Field of Classification Search
  CPC ......................... A61M 35/003; A61M 35/006
  (Continued)

(56) References Cited

U.S. PATENT DOCUMENTS

| 2,127,794 A | 8/1938 | Wastman |
| 2,505,295 A | 4/1950 | Meyers |

(Continued)

FOREIGN PATENT DOCUMENTS

| GB | 2 185 880 | 8/1987 |
| WO | WO 2004-062709 | 7/2004 |

(Continued)

OTHER PUBLICATIONS

EP Pat. Appln. No. 08 769 216.6, Supplementary EP Search Report, 10 pages, dated Feb. 17, 2012.
(Continued)

*Primary Examiner* — Jennifer C Chiang
(74) *Attorney, Agent, or Firm* — Andrew F. Young, Esq.; Lackenbach Siegel, LLP

(57) ABSTRACT

A single-piece, injection molded, hand-held liquid dispensing applicator. The single-piece applicator comprising a source of fluid and a frangible applicator tip attached to the fluid source. When the frangible applicator tip is broken, the fluid flows from the source to an absorbent member attached to the applicator tip to spread the liquid on a surface. The frangible tip may comprise a support element permanently connected to the fluid source, a relatively rigid tongue element, and a frangible region therebetween. The tongue element may comprise ribs for reinforcement. The frangible tip may comprise a semi-permeable or non-permeable cover to control the speed and direction of the dispersion of the fluid. The dispensing applicator may be used in various medical applications.

20 Claims, 39 Drawing Sheets

Related U.S. Application Data continuation-in-part of application No. 13/306,681, filed on Nov. 29, 2011, now Pat. No. 9,073,382, which is a continuation of application No. 11/740,910, filed on Apr. 26, 2007, now Pat. No. 8,083,425, which is a continuation-in-part of application No. 11/138,142, filed on May 26, 2005, now Pat. No. 7,614,811, said application No. 13/306,681 is a continuation-in-part of application No. 12/596,103, filed on Jan. 4, 2011, now Pat. No. 8,628,265, which is a continuation of application No. 11/740,920, filed on Apr. 27, 2007, now Pat. No. 8,186,897, which is a continuation-in-part of application No. 11/138,142.

(51) Int. Cl.
   *A61M 35/00* (2006.01)
   *B43M 11/06* (2006.01)
   *A61L 2/00* (2006.01)
   *A61L 2/18* (2006.01)
   *A45D 34/04* (2006.01)

(52) U.S. Cl.
   CPC .......... *A61M 35/003* (2013.01); *B43M 11/06* (2013.01); *A45D 2200/1018* (2013.01)

(58) Field of Classification Search
   USPC .................................................. 401/132–134
   See application file for complete search history.

(56) References Cited

U.S. PATENT DOCUMENTS

| | | | |
|---|---|---|---|
| 3,063,084 A | | 11/1962 | Marinus |
| 3,271,810 A | | 9/1966 | Raffe |
| 3,324,855 A | | 6/1967 | Heimlich |
| 3,481,676 A | * | 12/1969 | Schwartzman ........ A45D 34/04 401/134 |
| 3,777,949 A | | 12/1973 | Chiquiari-Arias |
| 3,847,151 A | * | 11/1974 | D'Alessandro ......... A47L 17/00 15/244.1 |
| 4,218,155 A | | 8/1980 | Weidner |
| 4,415,288 A | * | 11/1983 | Gordon .................. A47K 7/028 401/132 |
| 4,732,287 A | | 3/1988 | Bennett |
| 4,747,720 A | | 5/1988 | Bellehumeur et al. |
| 5,090,832 A | | 2/1992 | Rivera et al. |
| 5,229,061 A | | 7/1993 | Van Dyke et al. |
| 5,302,358 A | | 4/1994 | Anderson et al. |
| 5,326,603 A | | 7/1994 | Van Dyke et al. |
| 5,435,660 A | | 7/1995 | Wirt |
| 5,586,672 A | | 12/1996 | Schneider et al. |
| 5,658,084 A | | 8/1997 | Wirt |
| 6,042,286 A | | 3/2000 | Pazienza |
| 6,082,919 A | | 7/2000 | De Laforcade |
| 6,086,279 A | | 7/2000 | Yen |
| 6,422,778 B2 | | 7/2002 | Baumann et al. |
| 6,533,484 B1 | | 3/2003 | Osei et al. |
| 7,063,476 B1 | | 6/2006 | Pinnix et al. |
| 7,540,681 B2 | * | 6/2009 | Cybulski ............. A61M 35/006 401/133 |
| 7,946,779 B2 | | 5/2011 | Kaufman et al. |
| 2001/0055511 A1 | | 12/2001 | Baumann et al. |
| 2003/0049069 A1 | | 3/2003 | Osei et al. |
| 2003/0086747 A1 | | 5/2003 | Baumann et al. |
| 2004/0114988 A1 | | 6/2004 | Baumann et al. |
| 2004/0253039 A1 | | 12/2004 | Stenton |
| 2006/0269355 A1 | | 11/2006 | Kaufman |
| 2011/0142527 A1 | | 6/2011 | Kaufman et al. |

FOREIGN PATENT DOCUMENTS

| | | |
|---|---|---|
| WO | WO 2006/041801 | 4/2006 |
| WO | WO 2006-041801 | 4/2006 |
| WO | WO 2007/018541 | 2/2007 |

OTHER PUBLICATIONS

EP Pat. Appln No. 08 769 216.6, Communication pursurant to Rules 70(2) and 70a(2) EPC, 1 page, dated Mar. 7, 2012.

PCT/US2008/061776, European Office Action mailed Mar. 7, 2012, received Mar. 13, 2012, 11 pages.

International Search Report and Written Opinion, PCT/US2013/057017 mailed Nov. 19, 2013, 19 pages.

* cited by examiner

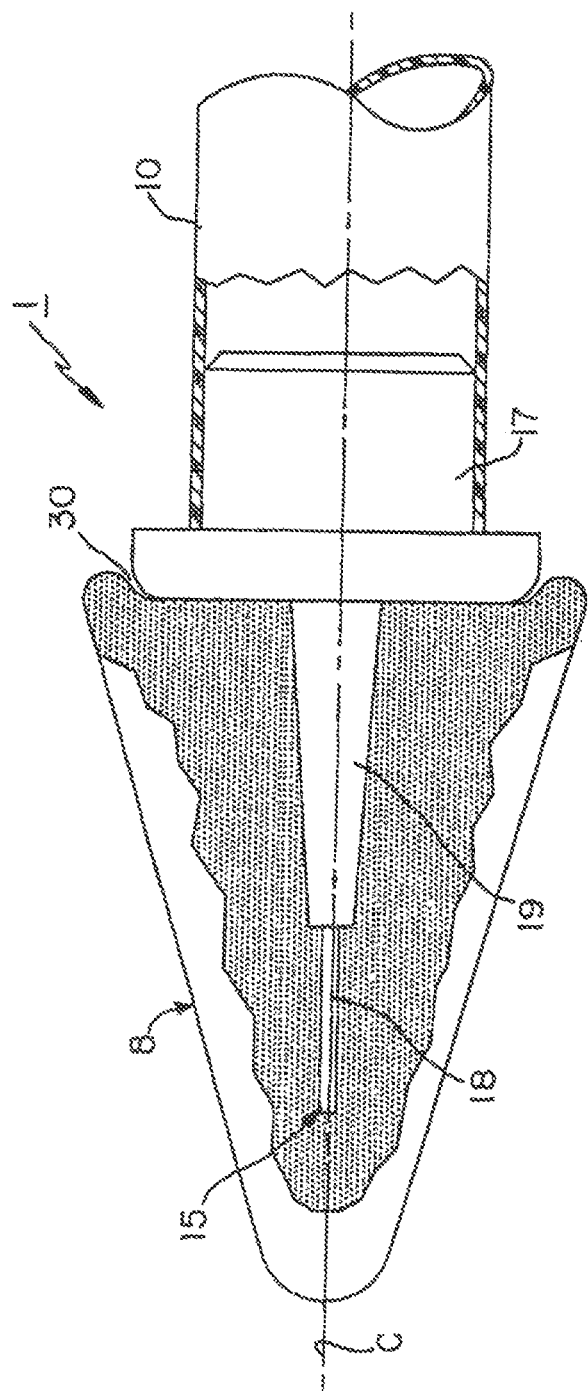

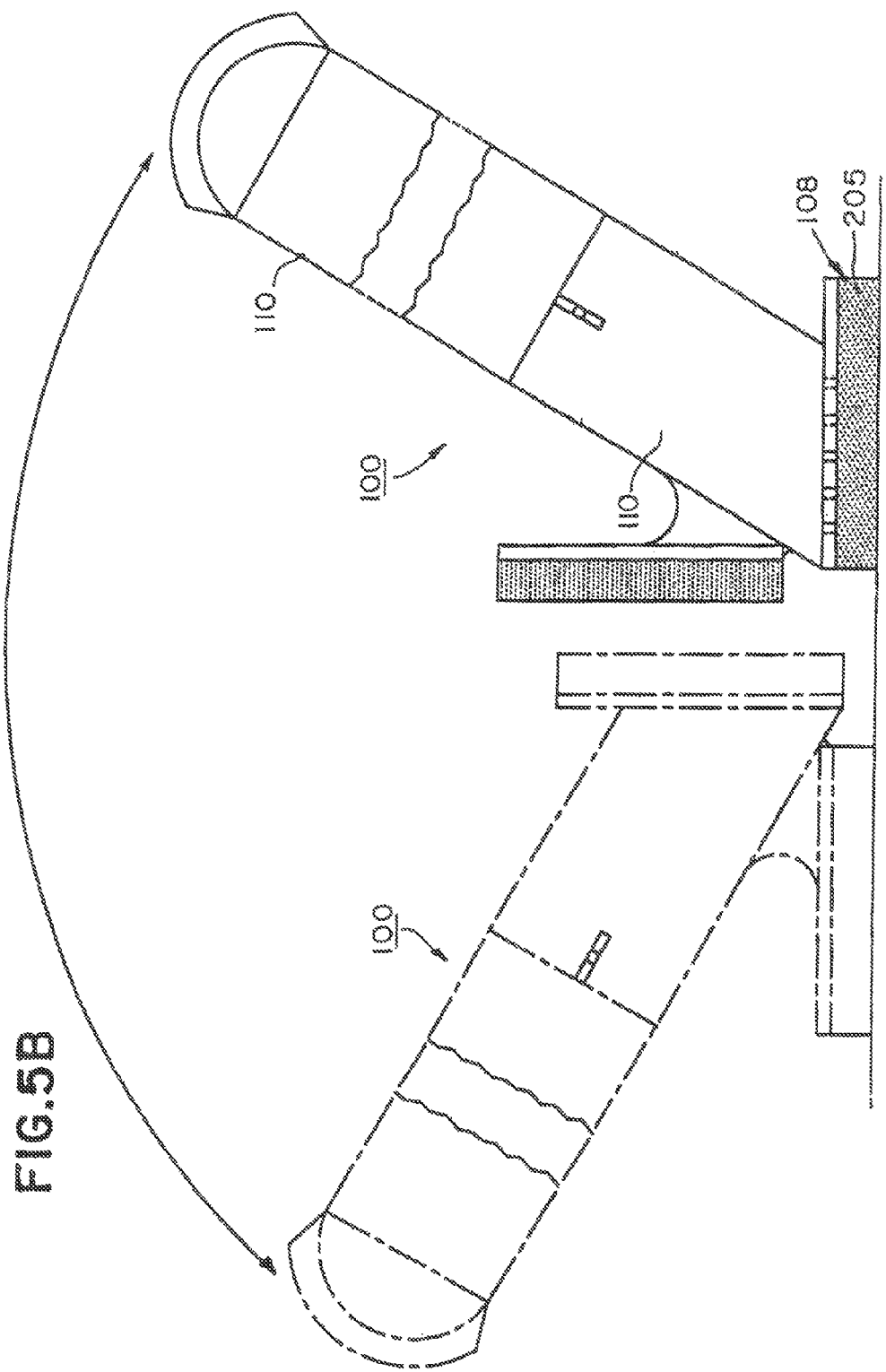

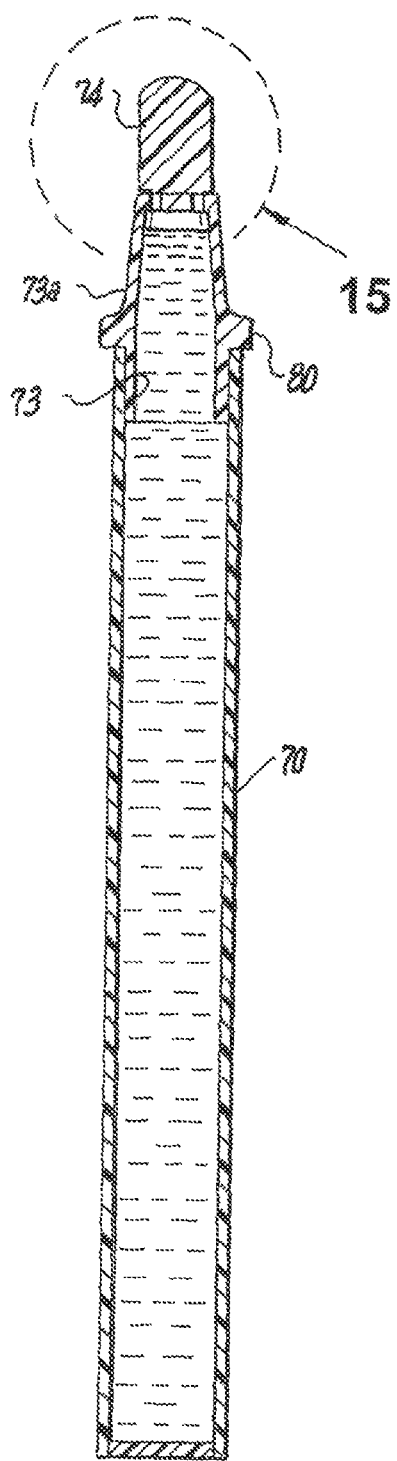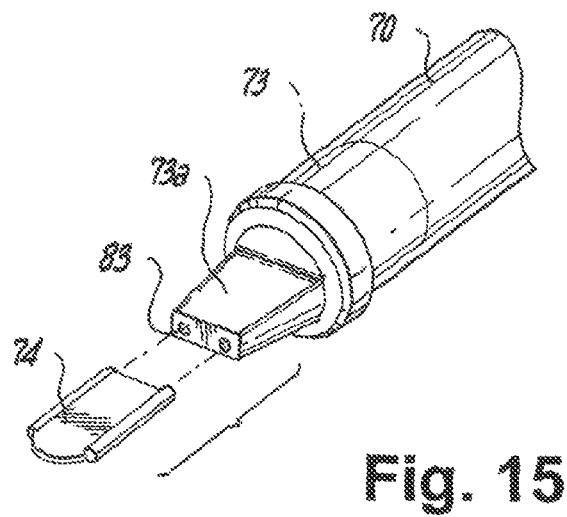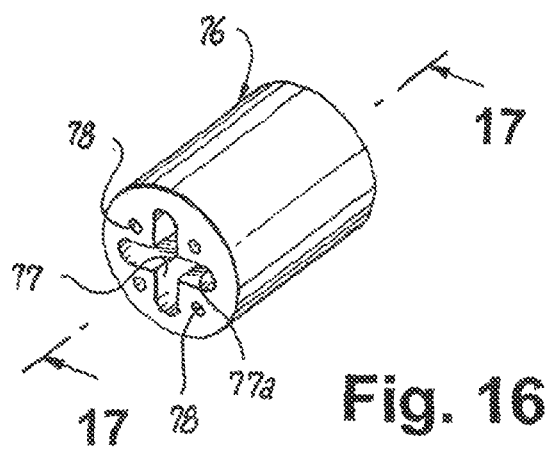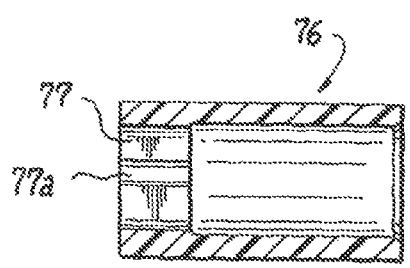
Fig. 14
Fig. 15
Fig. 16
Fig. 17

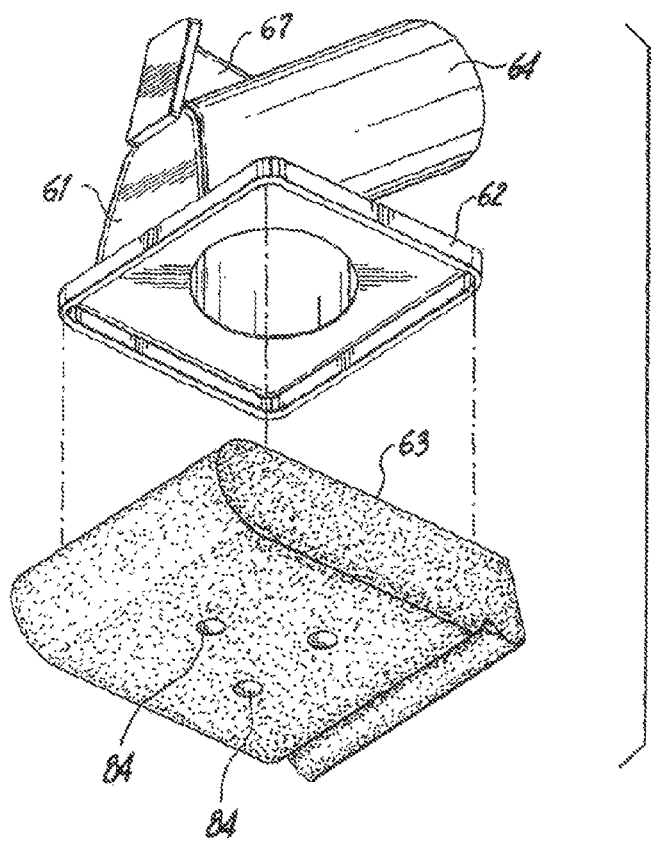
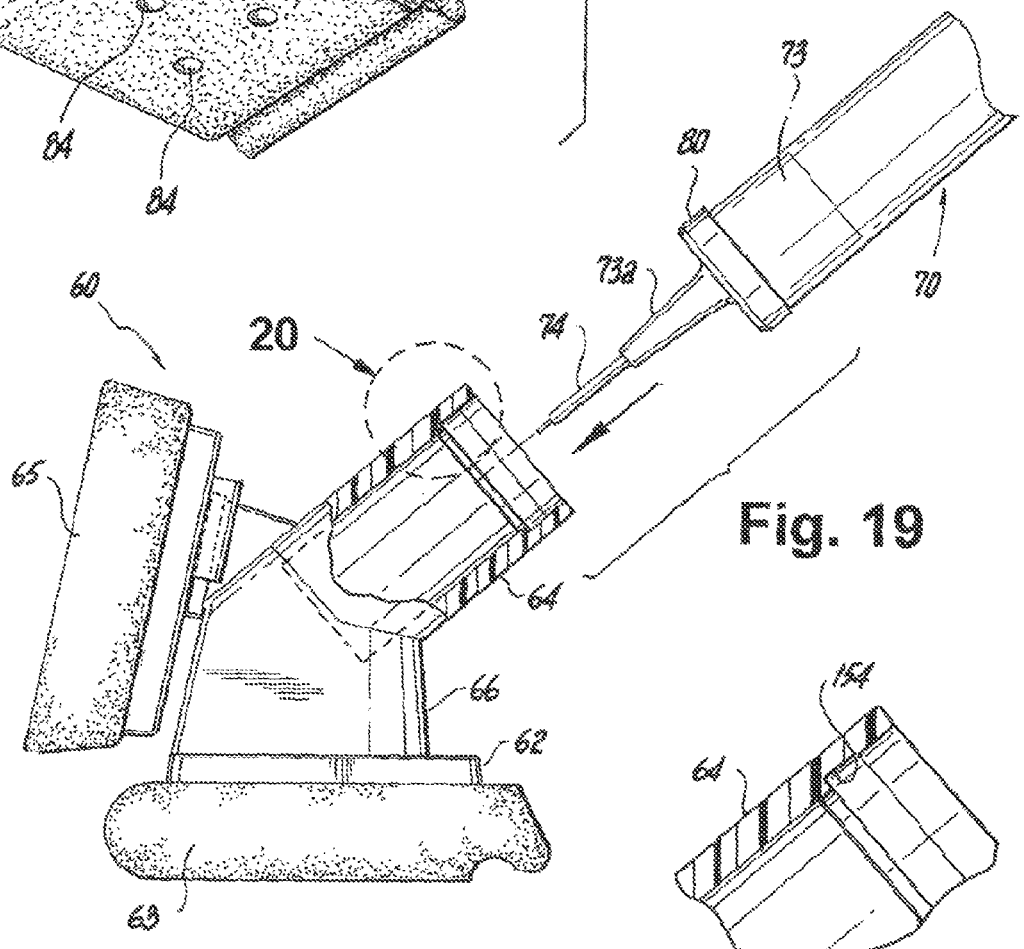

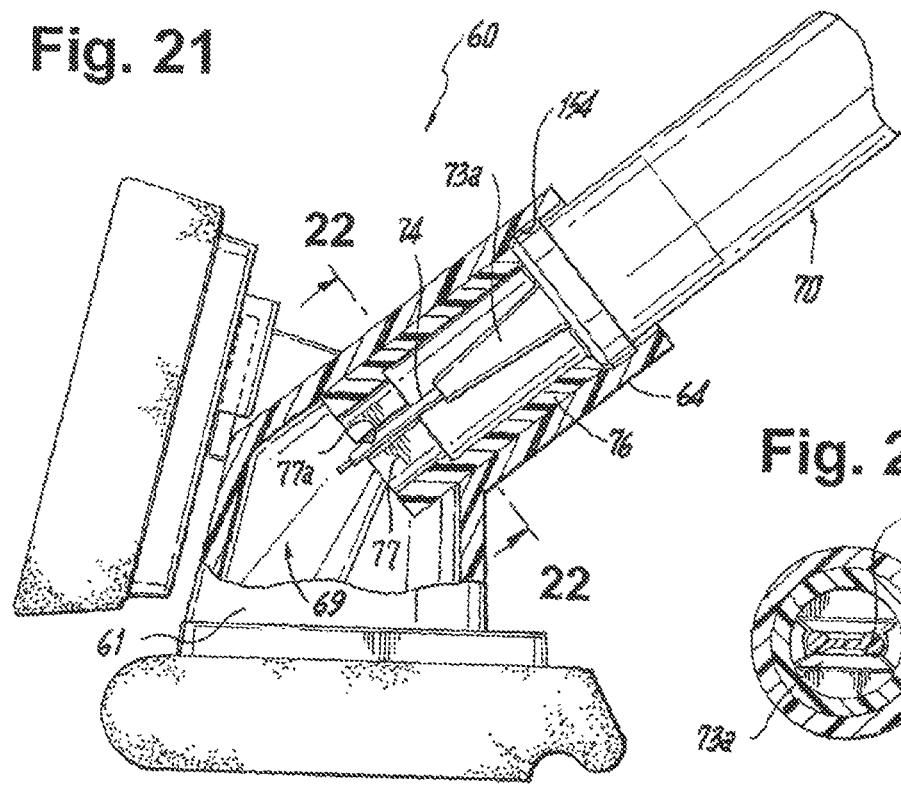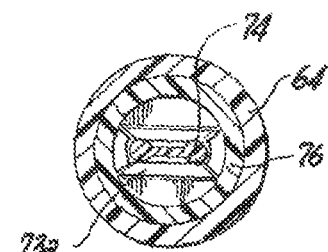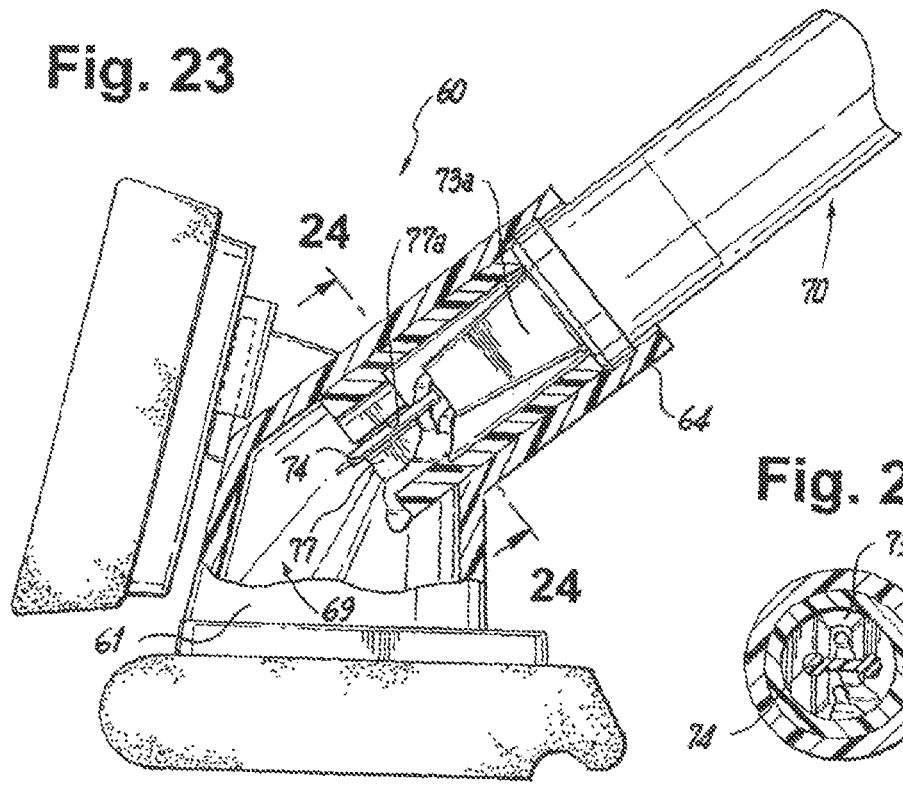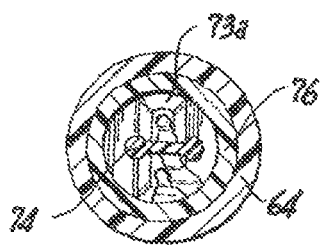

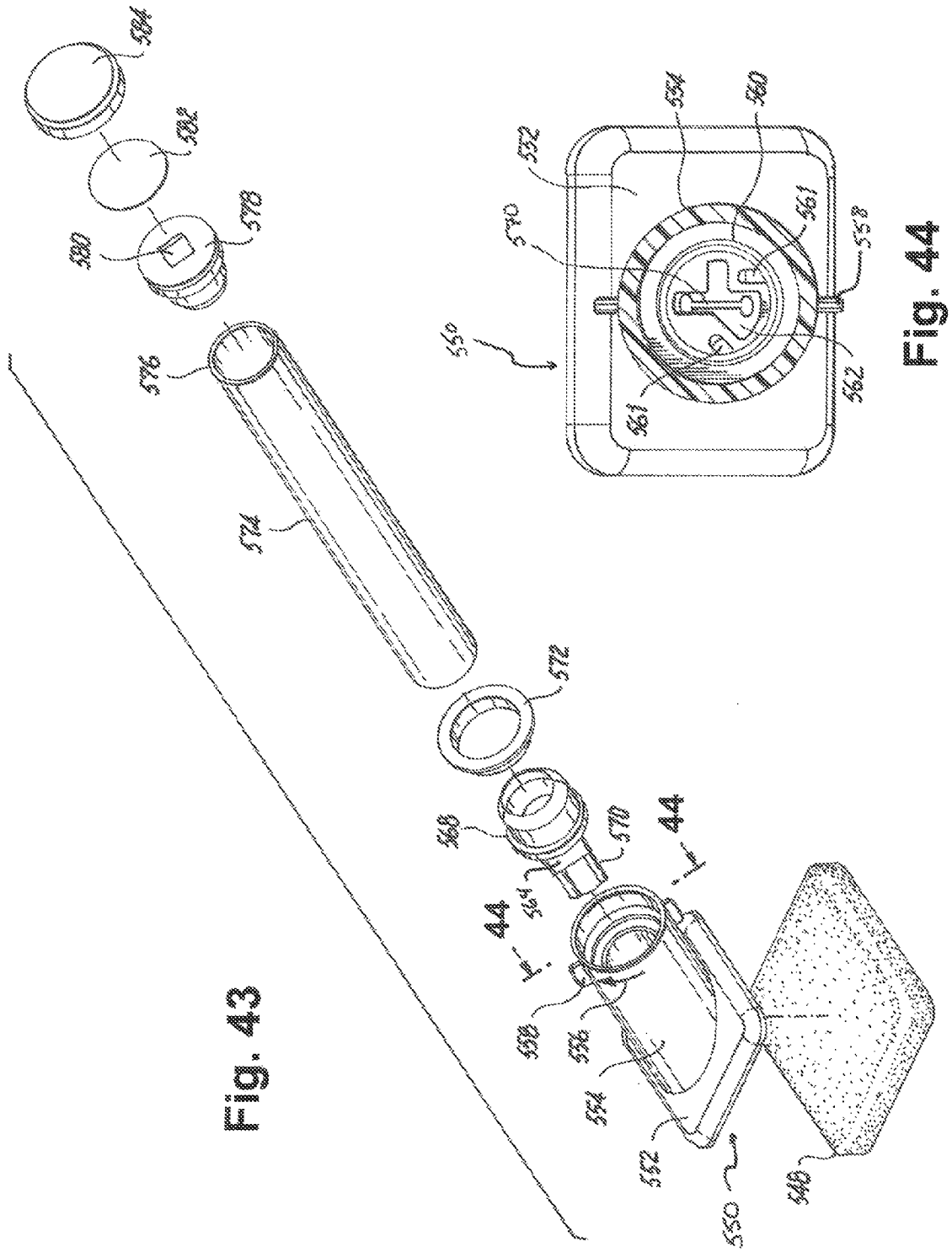

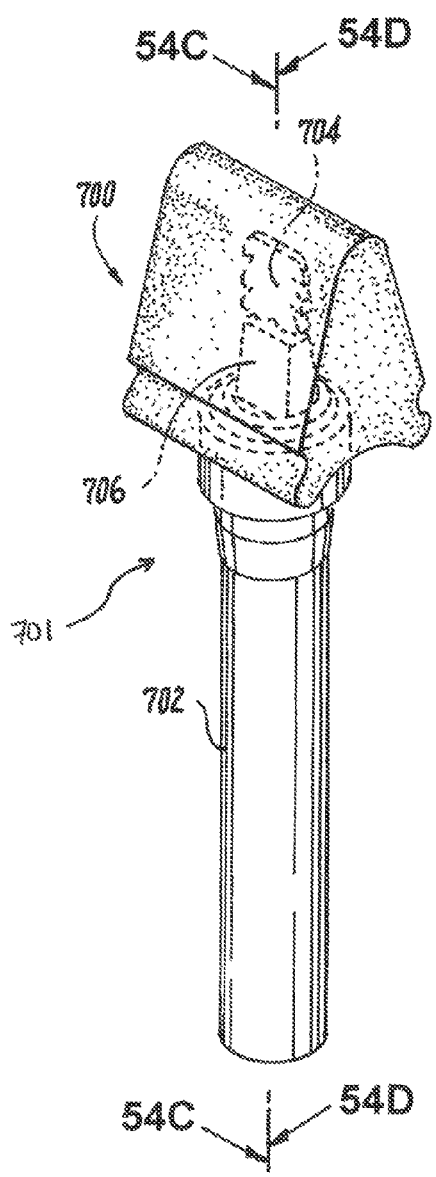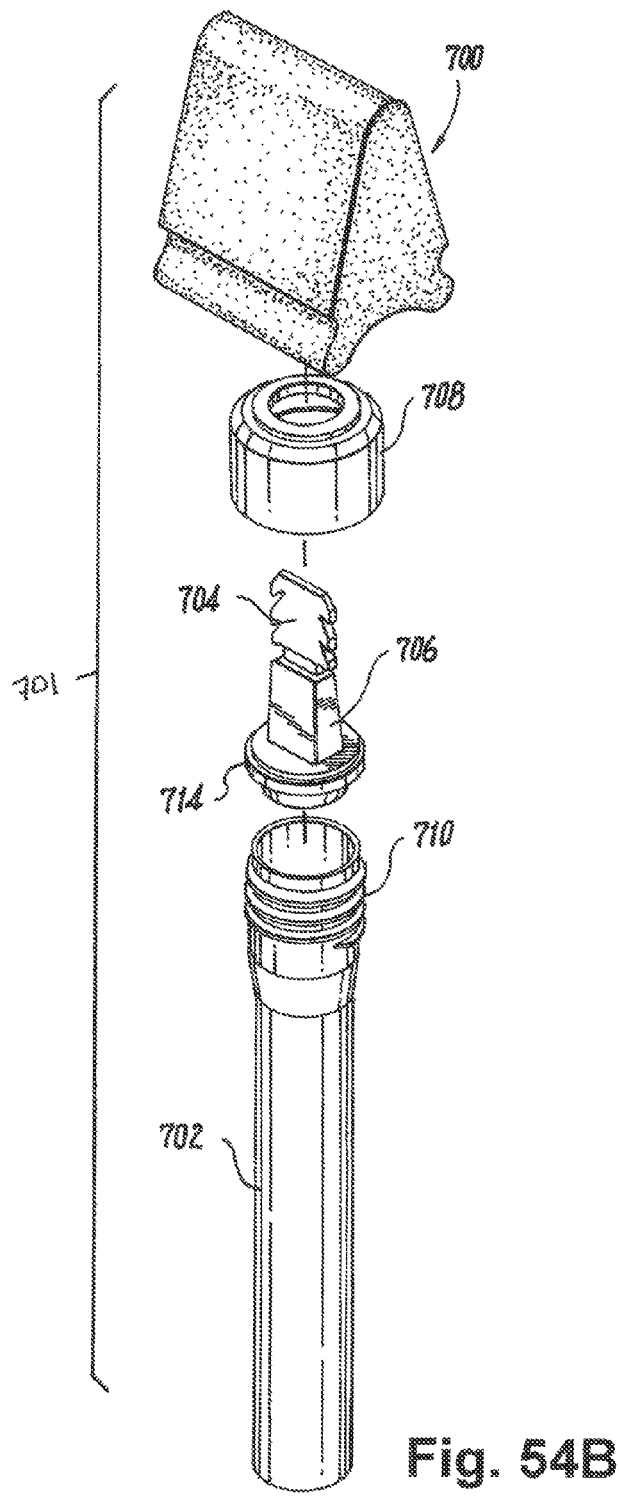
Fig. 54A
Fig. 54B

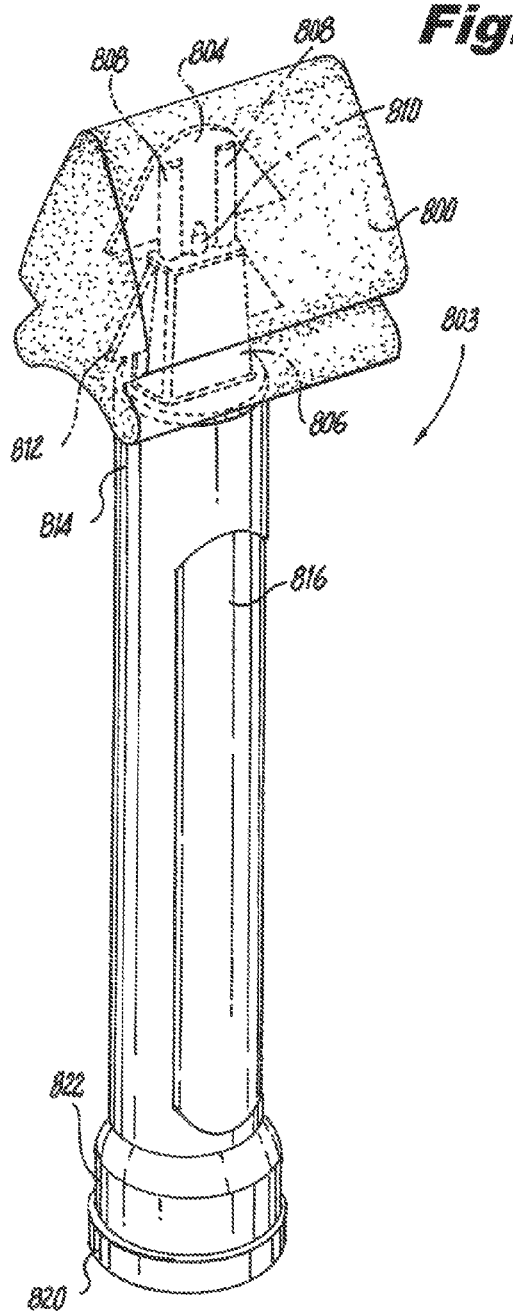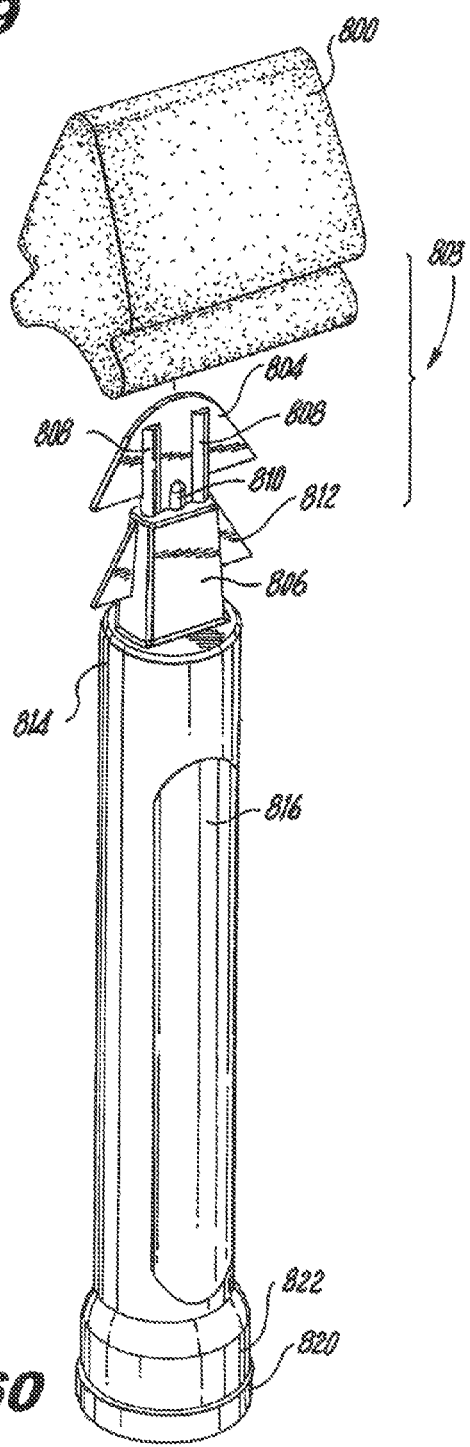
Fig. 59
Fig. 60

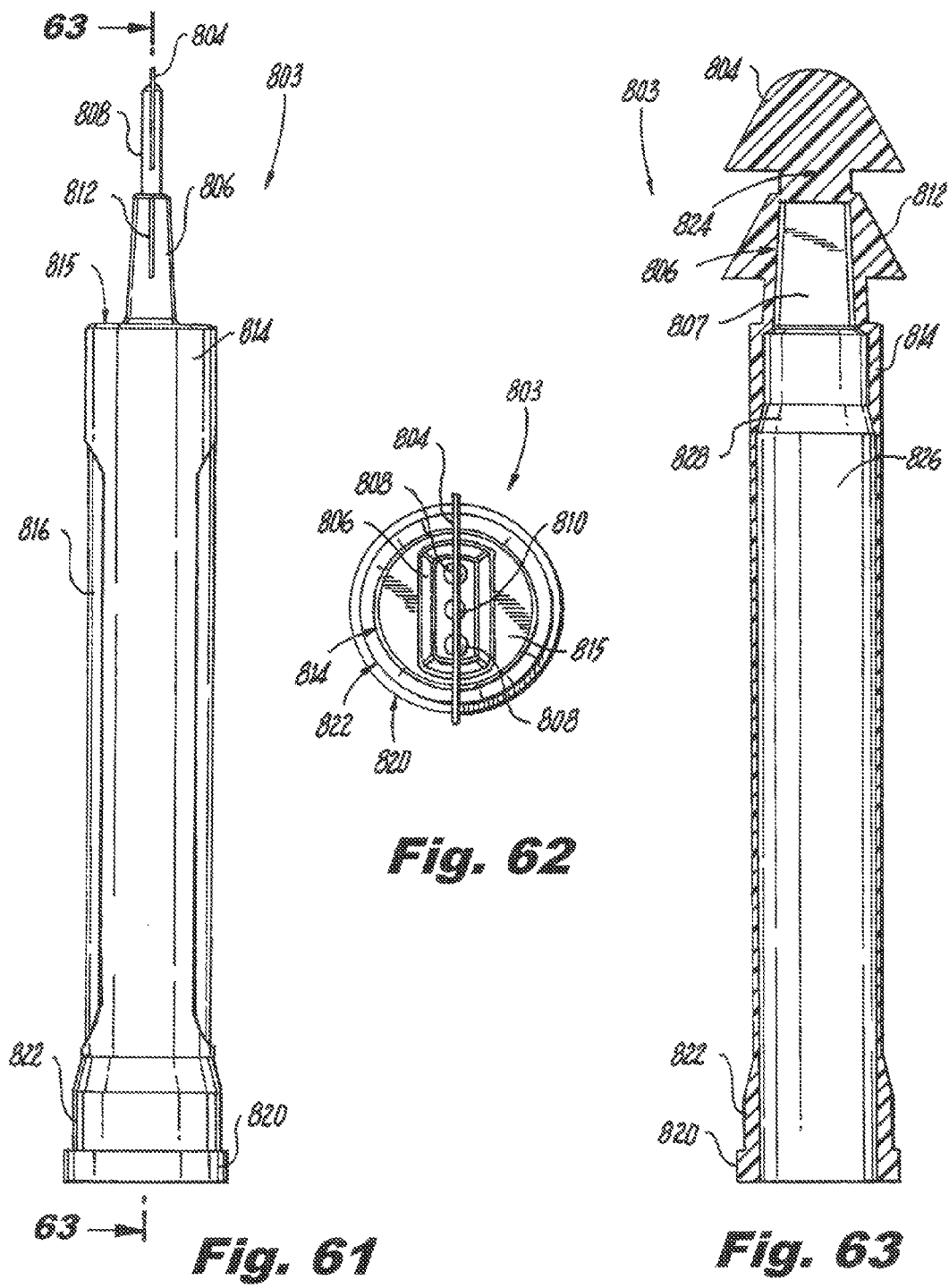

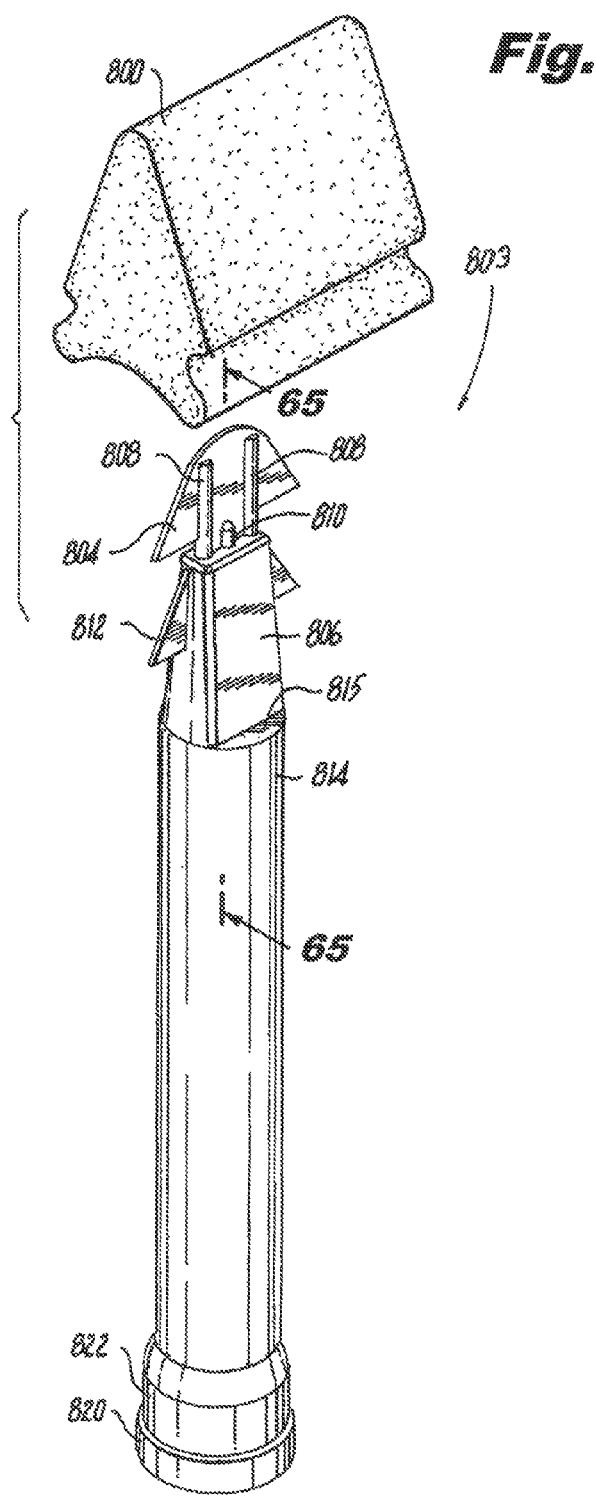
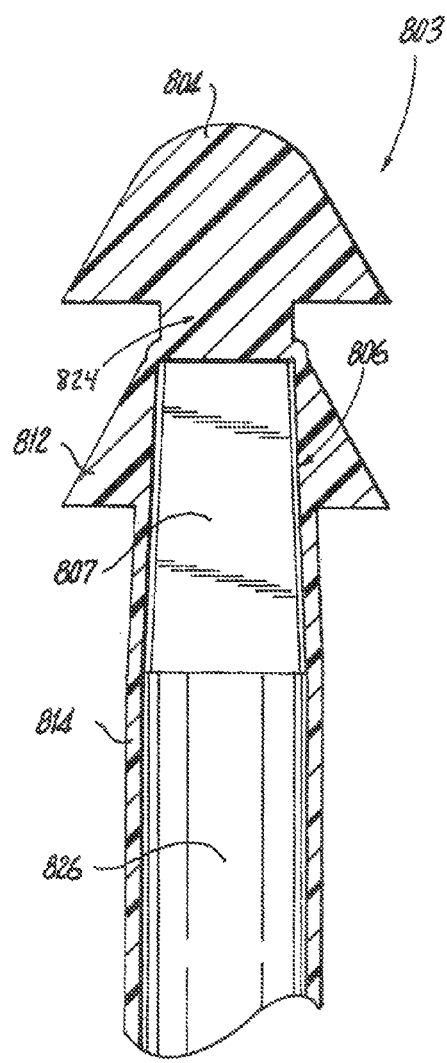
Fig. 64
Fig. 65

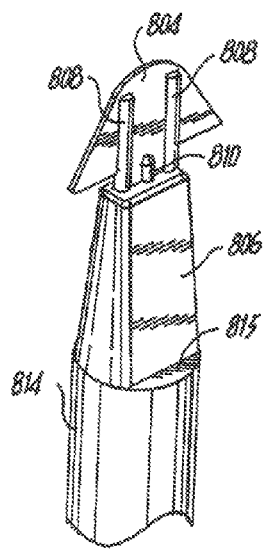 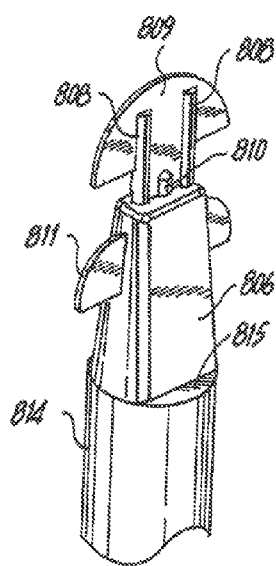 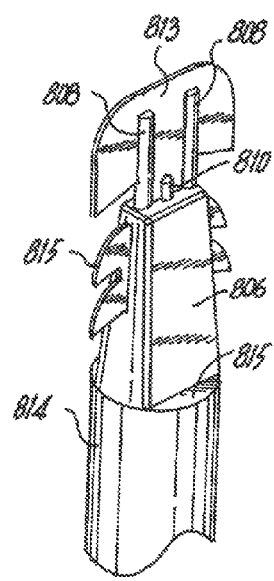
*Fig. 66A*     *Fig. 67A*     *Fig. 68A*
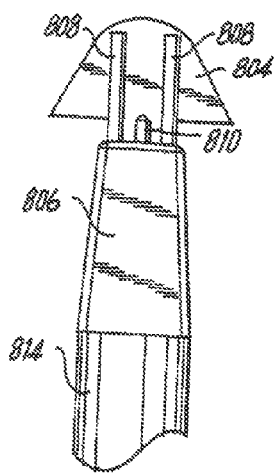 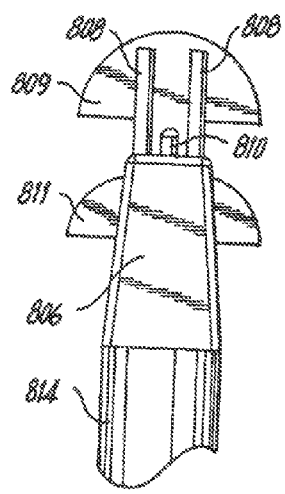 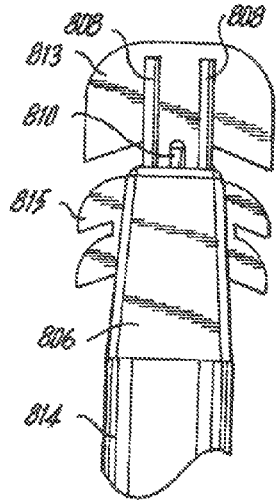
*Fig. 66B*     *Fig. 67B*     *Fig. 68B*

DISPENSING APPLICATOR FOR FLUIDS

CROSS-REFERENCE TO RELATED APPLICATIONS

This application is a continuation-in-part of, and claims priority from, U.S. Ser. No. 13/306,681 for a DISPENSING APPLICATOR FOR FLUIDS, filed Nov. 29, 2011, which is a continuation of, and claims priority from, U.S. Ser. No. 11/740,910 for a DISPENSING APPLICATOR FOR FLUIDS, filed Apr. 26, 2007, and now U.S. Pat. No. 8,083,425, which is a continuation-in-part of, and claims priority from, U.S. patent application Ser. No. 11/138,142 for a DISPENSING APPLICATOR FOR FLUIDS, filed May 26, 2005, and now U.S. Pat. No. 7,614,811, the entire contents of each of which are incorporated herein fully by reference, AND this application is a continuation-in-part of, and claims priority from, U.S. Ser. No. 12/596,103 for a DISPENSING APPLICATOR FOR FLUIDS, filed Jan. 4, 2011, which is a continuation of, and claims priority from, U.S. Ser. No. 11/740,920 for a DISPENSING APPLICATOR FOR FLUIDS, filed Apr. 27, 2007, and now U.S. Pat. No. 8,186,897, which is a continuation-in-part of, and claims priority from, U.S. patent application Ser. No. 11/138,142 for a DISPENSING APPLICATOR FOR FLUIDS, filed May 26, 2005, and now U.S. Pat. No. 7,614,811, the entire contents of each of which are incorporated herein fully by reference.

BACKGROUND OF THE INVENTION

Field of the Invention

The present invention is directed in general to a device for swabbing a surface (e.g., skin) that is gripped by a user at one end and has a sponge or absorbent material at the other end. Further, the present invention is directed to such device for swabbing a surface having a source of a fluid (e.g., disinfectant or medicament) in communication with the sponge or absorbent material. Specifically, the present invention is directed to such a fluid-containing device for swabbing a surface further having an internal means that may be fractured or separated for the purpose of allowing the fluid to flow from the fluid source to the sponge or absorbent material. Further, the present invention is directed to such a fluid-containing means for swabbing a surface further having an anvil structure internal to the fluid-containing means with any of a variety of configurations for causing the fracture of the fracture means.

For illustration purposes, the present invention is described herein as embodied in a hand-held dispensing applicator configured with a tube-like handle as a fluid source and a sponge-like applicator head, it being understood, however, that its broader aspects the invention is not limited thereto but may also be embodied in other forms of dispensing applicators.

Description of the Related Art

Applicators consisting of a wooden or plastic tube having a bud of cotton on one or both ends, are widely used for numerous purposes, such as the topical application of substances to the human body. A demand exists for a product of this kind, which serves not only as an applicator, but also as a container for substances that are to be applied to the human body. To be practical, such a device would have to have a manually frangible portion that can readily be broken, while at the same time being so constructed so as to prevent inadvertent fracture. An applicator of this nature would be useful for numerous purposes.

Prior dispensing applicators allow an excess amount of fluid to flow too quickly, and the fluid tends to pool on the surface. Depending upon the fluid being dispensed, such pooling can lead to patient discomfort, chemical burns, and even electrical shock if the dispensed fluid comes into contact with electrical leads attached to the patient's body.

Moreover, in prior art dispensing applicators, the dispensed fluid tends to accumulate at the rear-most portion of the absorbent member, which is closest to the fluid source, instead of preferably evenly spreading throughout the absorbent member. As the volume of the dispensed fluid gradually increases at the rear portion of the absorbent member, the fluid begins to uncontrollably drip, thus, causing substantial inconvenience to a user.

Accordingly, a need exists for a dispensing applicator overcoming the above-identified drawbacks of the known related art. In particular, a further need exists for a hand-held dispensing applicator that has a simple structure allowing the practitioner to deliver fluid to the surfaces to be treated in a controllable manner. Another need exists for a dispensing applicator that has an easily actuatable structure requiring minimal application of manual force. Further, a need exists for a hand-held dispensing applicator that has a structure minimizing uncontrollable distribution of fluid.

SUMMARY OF THE INVENTION

In light of the foregoing, an embodiment of the present invention provides a hand-held dispensing applicator comprising a source of fluid, a frangible applicator tip attached to the fluid source, and an absorbent member attached to the frangible applicator tip. When the frangible applicator tip is broken, fluid flows from the source to the absorbent member, whereby the fluid is applied and spread on a surface. Preferably, the fluid is applied and spread on a surface in a controlled amount. Preferably, the fluid source is in the shape of a hollow tube container that is integrally formed, as a single piece, from a relatively rigid synthetic resinous material. Preferably, the frangible applicator tip comprises a support element permanently connected to the fluid source, a relatively rigid tongue element extending outwardly of the support element at an end of the container, and a frangible region therebetween. Extending through the support element is a fluid conduit that is open at the end attached to the fluid source and sealed by the tongue element at the end attached to the absorbent member. By deflecting the tongue element relative to the support element, with a force of substantially predetermined magnitude, the frangible region between the tongue and support elements will fracture, thereby permitting fluid to flow from the fluid source through the conduit, and into the attached absorbent member. Preferably, the tongue element comprises ribs for reinforcing the tongue element to resist unintentional breaking of the frangible region. More preferably, the applicator tip comprises a semi-permeable or non-permeable cover disposed around the frangible region to control the speed and direction of the dispersion of the fluid in the absorbent member.

In another embodiment, the dispensing applicator comprises a mounting body which has a stem piece extending from a mounting body top part, and a lower body part which carries at an underside of the latter, an absorbent applicator. An elongated fluid container having a first end that is attachable at a second opposite end thereof, and with a snap fit, in the stem piece. Optionally, threading of the first end of the fluid container may be used to secure to the stem piece. The container includes a frangible region remote from said first end, and a rigid tongue element extends longitudinally from the frangible region, a tip end of the tongue element defining the container's opposite second end.

A fracture anvil is preferably disposed in the stem piece. To fracture the container frangible region in order to release fluid therefrom and into the absorbent applicator, a relative movement between the container, i.e., the tongue element thereof, and the fracture anvil is effected. This is done with the tongue element in contact with the fracture anvil. The contact and relative movement produce the rupture of the frangible region, and, more specifically, at the joinder location of the tongue element and frangible region.

In one form, the fracture anvil is a cylindrical body having a cruciform passage extending therethrough and which receives the flat blade-like tongue element. In a second form, the fracture anvil is a cylindrical body having a partial or one-half cruciform passage extending therethrough and which receives the flat blade-like tongue element. By effecting a relative rotation between the fracture anvil and the container, the fracture of the frangible region results. Optionally, the cruciform passage may extend completely through the fracture anvil, or may only extend partially through the fracture anvil.

In another form, the fracture anvil is a cylindrical body having a partial cruciform, partial semi-circular passage (e.g., see FIG. 42A) extending therethrough and which receives the flat blade-like tongue element. By effecting a relative rotation between the fracture anvil and the container, the partial fracture of the frangible region results. Optionally, the partial cruciform, partial semi-circular passage may extend completely through the fracture anvil, or may only extend partially through the fracture anvil.

In still another form, the fracture anvil is a truncated cylinder received in the stem piece. By urging the container axially into the stem piece and against an inclined end face of the fracture anvil, the tongue element is deflected laterally from its normal disposition to cause the rupture at the joinder location thereof with the remainder frangible region. With the joinder structure ruptured, the fluid contents release from the container. Flow gutters or channels are defined in the fracture anvil to insure free contents flow from the container past or through the fracture anvil to the absorbent applicator. The arrangement of the tongue element and its structure is designed such as to allow retention of at least one ribbon residue material connecting the tongue element to the frangible region precluding passing of the tongue element into a contents flow channel wherein it could impede or block flow to the absorbent applicator.

A further feature provides a snap fit cap fitted on an opposite contents filling end of the container opposite the tongue member end, and provided with a seal that excludes any possible and contaminating air presence in the contents at the container end. Optionally, the cap may be screwed on or permanently affixed with glue or some other adhesive.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention. For a more complete understanding of the present invention, reference is now made to the following drawings in which:

FIG. 2 is a side cross-sectional view of the dispensing applicator of FIG. 1;

FIG. 5B is a diagrammatic view illustrating two positions of the dispensing applicator of FIG. 5A;

FIG. 14 is a top plan view of the fluid source container, the container being closed at one end, an attachment body being located remote from said container at one end, a frangible length region including a tongue element extending longitudinally from said attachment body;

FIG. 15 is an exploded perspective view of the applicator portion in the circle area 15 of FIG. 14, the tongue element being separated a distance from the attachment body frangible region so that the fluid container contents outflow apertures produced when the tongue element is fractured from the frangible length region can be seen;

FIG. 16 is a perspective view of an alternate embodiment of a fracture anvil shown in the circle area 16 in FIG. 13 of a fracture anvil removably inserted in an applicator mounting block part of the applicator head, the fracture anvil having a cruciform passage for reception of the fluid source container tongue element, the fracture anvil being employed to effect fracture of the frangible region-tongue element joinder on a relative rotatable movement between said container and said fracture anvil;

FIG. 17 is a side cross-sectional view of the fracture anvil taken along the line 17-17 in FIG. 16;

FIG. 18 is an exploded left bottom side perspective view of the mounting block which receives an absorbent applicator at a block bottom side;

FIG. 19 is a left side view partly in section, partly in cross-section, of the mounting block, the absorbent applicator being affixed at the block bottom side, and an absorbent swab member being affixed to a block front side adjacent to said bottom side, the fluid source container being depicted in position just before the tongue carrying end thereof is inserted into the mounting block;

FIG. 20 is a partial cross-sectional view of an upper inlet part of the mounting block stem piece indicated in the circle 20 portion in FIG. 19, there being an annular slot inside and adjacent entry to the upper inlet, said slot defining a detent for retaining a flange on the container to effect snap fit of the container to the applicator mounting body.

FIG. 21 is a left side view similar to FIG. 19 showing the mounting block with the tongue element positioned in the cruciform passage of the fracture anvil in pre-fracture condition, the container being snap fitted to the mounting block;

FIG. 22 is a cross-section view taken on the line 22-22 in FIG. 21;

FIG. 23 is a view similar to FIG. 21 but showing the post fracture position of the fracture anvil, which has been rotated approximately ninety degrees from the position it occupied in FIG. 21;

FIG. 24 is a cross-section view taken on the line 24-24 in FIG. 23;

FIG. 43 is an exploded left front side perspective view of another embodiment of a dispensing applicator wherein a fluid containing source is receivably attachable to an applicator mounting body stem piece in snap fit connection therewith, initiation of fluid flow being effected with a relative rotational movement between the fluid source container and a fracture anvil in the mounting body;

FIG. 44 is a cross-section view taken along the line 44-44 in FIG. 43 showing relative position of the tongue member within the partial cruciform, partial semi-circular passage of the fracture anvil;

FIG. 54A is an elevated perspective view of still another alternative embodiment of an assembled dispensing applicator wherein a fluid containing source is receivably attachable to an applicator mounting body stem piece in snap fit connection therewith, initiation of fluid flow being effected with a relative downward movement between the fluid source container and a fracture member in the mounting body;

FIG. 54B is an exploded left front side perspective view of the dispensing applicator shown in FIG. 54A wherein a fluid containing source is receivably attachable to an applicator mounting body stem piece in snap fit connection therewith, initiation of fluid flow being effected with a relative downward movement between the fluid source container and a fracture member in the mounting body;

FIG. 59 shows a perspective view of the dispensing applicator according to another embodiment of the present invention;

FIG. 60 shows a partial exploded perspective view of the dispensing applicator shown in FIG. 59;

FIG. 61 shows a side elevation plan view of the dispensing applicator shown in FIG. 59, without the applicator sponge;

FIG. 62 shows a top plan view of the dispensing applicator shown in FIG. 61;

FIG. 63 shows a front cross-sectional view of the dispensing applicator shown in FIG. 61 taken along line 63-63;

FIG. 64 shows a partial exploded perspective view of the dispensing applicator similar to the one shown in FIG. 59, but without the flat grip region on the tube handle and an alternative embodiment for the distal end of the handle;

FIG. 65 shows a partial cross-sectional view of the dispensing applicator shown in FIG. 64 taken along the line 65-65;

FIGS. 66A and 66B shows a partial perspective view of the dispensing applicator according to an alternative embodiment of the present invention further depicting a second alternative set of applicator head fins;

FIGS. 67A and 67B shows a partial perspective view of the dispensing applicator according to an alternative embodiment of the present invention further depicting a second alternative set of applicator head fins; and FIGS. 68A and 68B shows a partial perspective view of the dispensing applicator according to an alternative embodiment of the present invention further depicting a third alternative set of applicator head fins.

DETAILED DESCRIPTION OF THE PREFERRED EMBODIMENTS

Figure 1:
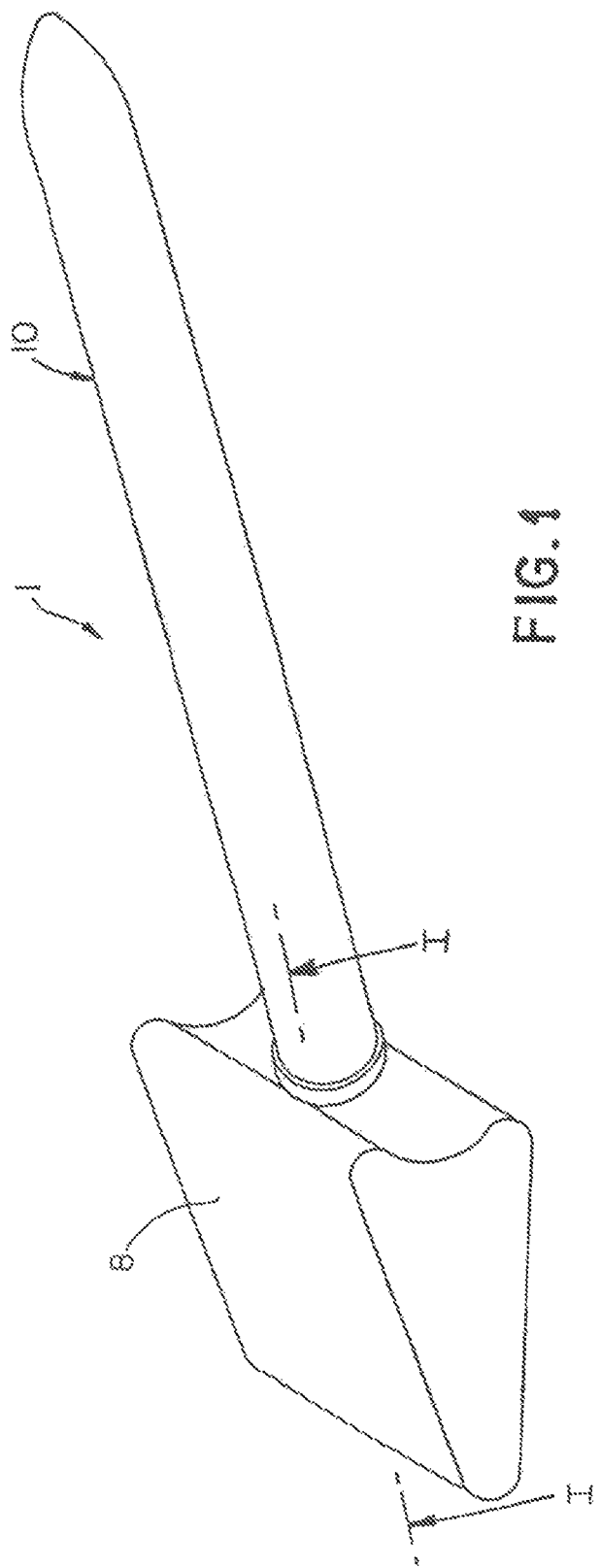
FIG. 1 is a perspective view of a dispensing applicator according to the present invention.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

Referring now to the drawings, FIGS. 1 and 2 in particular, illustrate a dispensing applicator according to a first embodiment of the dispensing applicator according to the present invention generally indicated as reference numeral 1. Dispensing applicator 1 comprises an absorbent applicator member 8, a fluid source 10, and an applicator tip 15. Absorbent member 8 may be of any suitable shape, such as cubic, cylindrical, conical, or wedge-like, and may comprise any suitable absorbent material, such as cotton or sponge. Fluid source 10, or handle, may have any suitable shape. As shown in FIG. 1, fluid source 10 is preferably a hollow, generally cylindrical body. The end of fluid source body located adjacent to absorbent member 8 is preferably sealed thereto at a joint or seam 30, such as by heat sealing, to enclose the fluid substance contained within fluid source body 10. Applicator tip 15 comprises an attachment member 17 and tongue member 18 joined thereto by a tapered frangible region or juncture 19.

Tongue member 18 is preferably a flat and broad shape that extends a distance into absorbent member 8, such that tongue member 18 is longer than it is wide (see FIGS. 4A to 4D). It should be noted that the attachment member 17 is relatively thick adjacent the fluid source body 10, and tapers toward frangible juncture 19. Absorbent member 8 is preferably connected to attachment member 17 and/or fluid source body 10.

The manner of utilizing dispensing applicator 1 will be self-evident, and simply involves holding the dispensing applicator 1 with the absorbent application member 8 against an application surface. Dispensing applicator 1 is held such that tongue member 18 is at an acute angle (i.e., substantially parallel) to the application surface. Sufficient downward pressure of tongue member 18 against the application surface will deflect tongue member 18 from the central axis c (see FIGS. 2, 4A, 5A) of the fluid source body 10. At a pre-determined amount of deflection, the frangible juncture 19 will fracture or break proximate the intersection thereof but will not separate. Fracture of the frangible juncture 19 will desirably be achieved by the application of approximately 0.25 to 5 pounds of force of tongue member 18 against the application surface and will cause opening for fluid flow proximate junctures or apertures 12 as will be discussed more fully below.

Referring still to FIG. 1, a dip mold process may be used to make source body 10, applicator tip 15, or both. The dip molding process begins with preheating of a male mold made from a material having relatively high heat capacity and coefficient of thermal conductivity. This heated mold is then placed in a fluidized bed of meltable particulate resinous material for a time needed to provide a coating of a desired thickness. The mold with melted resinous material is then removed from the fluidized bed, heated a second time and cooled. Finally the tube component is stripped from the mold.

As noted above, it is important for the proper functioning of the applicator that the tube be fabricated from a material that is sufficiently rigid to enable manual fracture of the frangible end portion. If the material is too flexible, deflection of the stem will not produce the desired result. On the other hand, if the material is excessively rigid and brittle, the possibility of an inadvertent fracture will exist, and compression of the body portion to promote flow would be precluded due to the likelihood of cracking, or simply because excess force is required. A variety of synthetic resinous materials may be utilized, the selection of which will be evident to those skilled in the art. The resin must have a sufficiently low melt viscosity to permit coverage of all mold surfaces, and it must produce a nonporous and pinhole-free structure. The polymer will normally be a thermoplastic, and exemplary materials include polypropylene, high density polyethylene, rigid polyvinyl chloride and nylon.

The tongue member of the applicator tip will preferably be elongated to facilitate attachment thereof to the absorbent member 8. However, it is not essential that the tongue member 18 be of any specific shape and, for example, may be rectangular or cylindrical. Regardless of the shape of tongue member 18, it is essential that suitable reinforcing ribs, as described hereinabove, be included to prevent unintentional breaking or separation of frangible portion 19. Moreover, the shape of tongue member 18 will dictate the shape of the orifice formed in applicator tip 15 where the tongue member 18 is fractured for fluid release. Accordingly, the flow rate and overall amount of fluid applied to an application surface by dispensing applicator 1 is a function of several factors, including the shape and strength of tongue member 18 (and the resulting orifice), the porosity of absorbent member 8, the density of the fluid, and the force employed by the user when breaking frangible portion 19 and pressing absorbent member 8 against the application surface. Determining the optimal flow rate for a given application is well within the ability of one skilled in the art and, therefore, will not be elaborated upon herein.

As stated above, the porous member may be made of any suitable material(s), most notably open cell, soft, and pliant sponge-like foam, that may be, for example, a polyurethane composition. The choice of material will depend largely upon the particular application and the characteristics of tongue member 18 and the fluid held in source body 10.

In its normal form, source body 10 will be of circular cross-section. However, other shapes are also believed to be feasible. The source body 10 may have a square, triangular, or rectangular cross-section, and the shape may indeed be asymmetrical in cross section and of dissimilar shapes at different points along its length. It will be appreciated therefore that, as used herein the term "diameter" is to be construed in a broad sense, so as to be applicable to non-circular elements corresponding to those shown, and to refer to the maximum cross-sectional dimension of the element. Although normally completely hollow, the source body 10 may include appropriate reinforcement elements, such as internal support pillars, to provide adequate overall strength and rigidity, while permitting the source body 10 to have a thinner than would otherwise be possible. Likewise, source body 10 may include a solid portion, for example, to be gripped while breaking frangible portion 19, so that source body 10 will not be prematurely compressed or squeezed, which might result in too much fluid flowing too quickly into absorbent member 8.

Figure 3C:
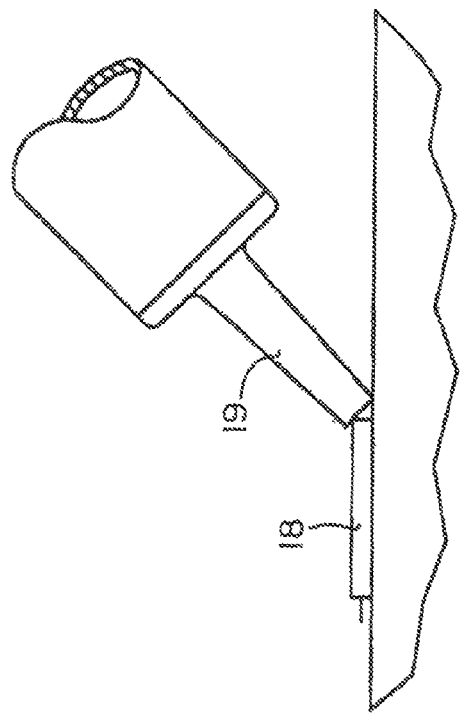
FIG. 3C is a top plan view of the applicator tip of FIG. 3B wherein apertures are formed in the broken frangible region.
Figure 3A:
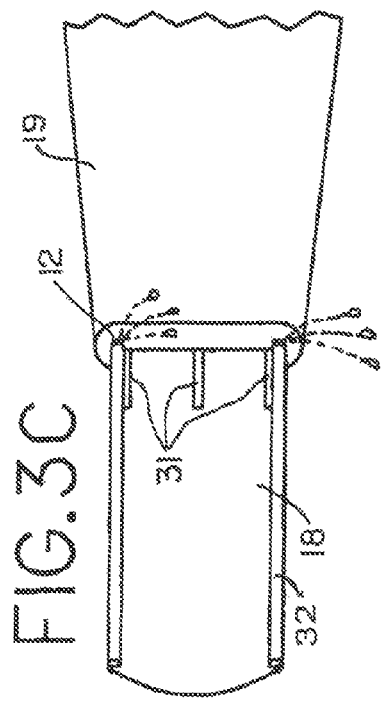
FIG. 3A is a top plan view of a preferred applicator tip for the dispensing applicator of FIG. 1.
Figure 3B:
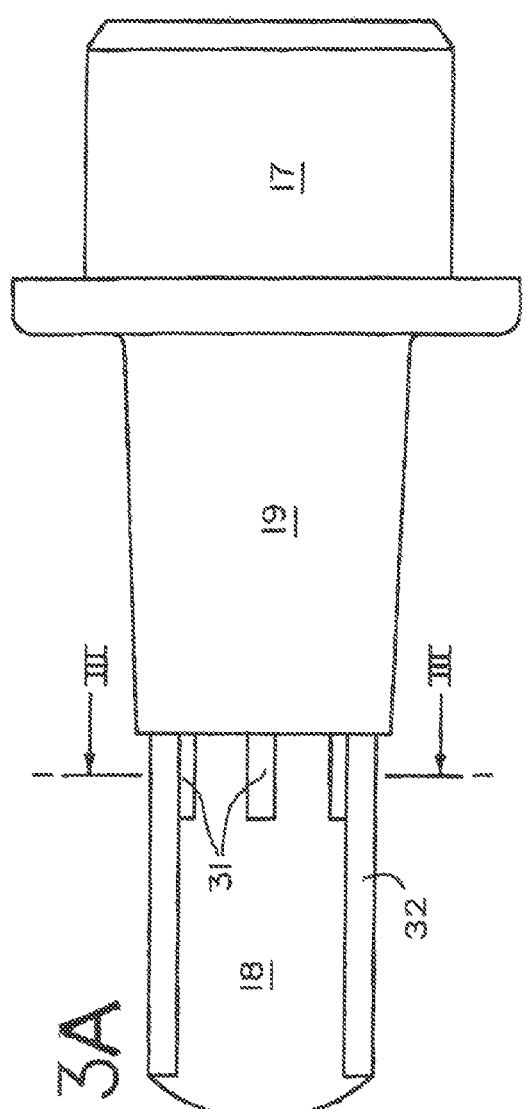
FIG. 3B is a side of the applicator tip of FIG. 3A wherein the frangible region is broken.

As shown in FIGS. 3B and 3C, breaking frangible juncture 19 will result in the formation of one or more apertures 12 through which fluid from source body 10 may flow into absorbent member 8 (not shown, but fluid flow is shown from apertures 12), such that tongue portion 18 may remain flexibly fixed to frangible juncture member 19 and is preferably prohibited from separation. In other words, fracture of the region proximate apertures is required, but tongue portion 18 remains flexibly joined along a hinge line and is strengthened by rib members 31, as will be discussed.

In its most preferable form, all portions of the source body 10 will have a wall thickness that is substantially uniform at a value of about 0.005 inch to about 0.025 inch (about 0.127 mm to about 0.635 mm), but may become thinner proximate regions 12 to urge ready fracture. The source body 10 is preferably made of polypropylene having a density of 0.897 g/cm2 and a flexural modulus of about 150 Kpsi (about 1035 MPa), as determined by ASTM method 790B. The source body 10 is preferably about 6 inches to about 10 inches in overall length, and about 0.25 to about 1.0 inches in diameter, so as to be convenient to grasp and still contain sufficient fluid for a single application.

The applicator tip 15 is about 1 to 3 inches long, and about 0.325 inches in diameter. The frangible juncture 19 will preferably have a thickness of about 0.0005 inch to about 0.002 inch (about 0.013 mm to about 0.050 mm). The one or more apertures 12, which are produced by the fracture of frangible juncture 19, but not the separation of tongue member 18, may be of any suitable size, but preferably have a width and height that is substantially correlated to the width and thickness of large ribs 31, 32 (see FIG. 3).

Referring to FIGS. 3A and 3C, tongue member 18 preferably comprises a plurality of reinforcing ribs 31, 32. Due to the reinforcing ribs and the resultant rigidity of tongue member 18, there will be reduced flex along the length of tongue 18, and an applied force on tongue member 18 will be effectively entirely transferred to and concentrated at frangible juncture 19 proximate apertures 12. The result will be the reliable fracturing of frangible juncture 19 proximate apertures 12, which fracturing results in the formation of one or more apertures 12 of suitable size on the same side as the force application to permit the fluid within the fluid source body 10 to be discharged therefrom and distributed across a predetermined area of absorbent application member 8 (FIG. 1). As noted above, it will generally be desirable for the material forming fluid source body 10 to be sufficiently thin to permit some compression of fluid source body 10, so as to enable discharge of a liquid therein at a faster rate than would otherwise occur, and/or to promote the flow of the fluid, especially if the fluid is relatively viscous. While in a first use apertures 12 may only fracture along a portion of the aperture directing fluid flow along one side (the force application side) if force is directed in the opposite direction, apertures 12 will fracture along their remaining region, retaining tongue member 18 only by the flexible hinge between apertures 12 and strengthening ribs 31.

Figures 4A, 4B:
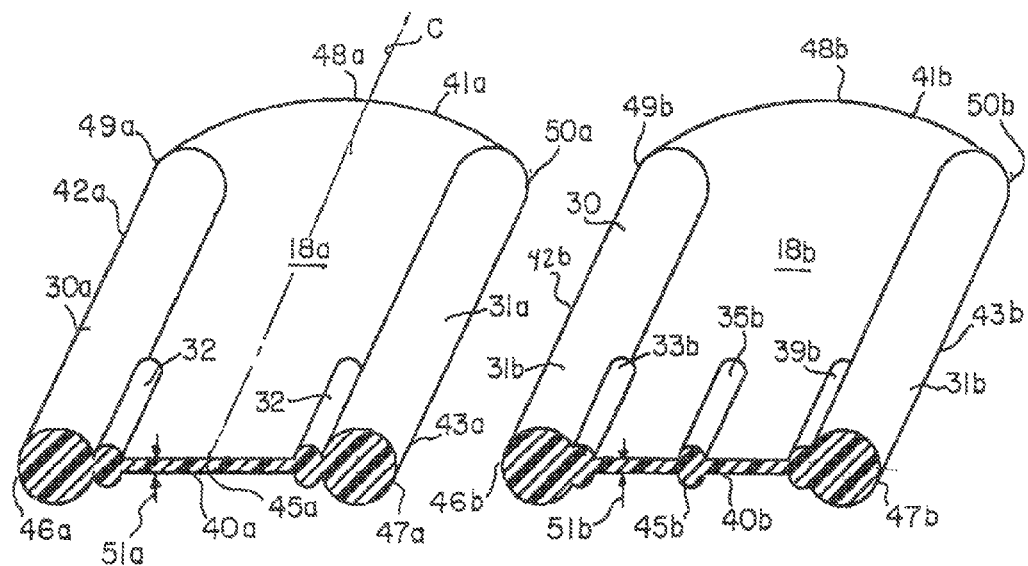
FIG. 4A is a perspective view of a first preferred tongue member for an applicator tip for the dispensing applicator of FIG. 1.
FIG. 4B is a perspective view of a second preferred tongue member for an applicator tip for the dispensing applicator of FIG. 1.

FIG. 4A illustrates a first arrangement of ribs for a tongue 18a. As shown, tongue 18a is rectilinear in shape with a bottom edge 40a, a top edge 41a, and side edges 42a, 43a. Bottom edge 40a is substantially linear with a central point 45a and corners 46a, 47a at which the proximate ends of respective side edge 42a, 43a meet. Top edge 41a is curvilinear with an apex 48a and corners 49a, 50a at which the distal ends of respect side edges 42a, 43a terminate. Central point 45a and apex 48a lie along central axis c. The distance between central point 45a and apex 48a is the length of tongue 18a, while the distance between corners 49a, 50a is the width of tongue 18a. The thickness 51a of tongue 18a is the distance between the top and bottom surfaces thereof. Side edges 42a, 43a each have a respective large rib 31a, 30a extending along the entire length thereof. It is notable that tongue 18a extends a distance beyond the length of the large ribs 31a, 30a to apex 48a, whereby top edge 41a is not reinforced. Ribs 31a, 30a are each about 3 times the thickness of tongue 18a and about ⅕th the width of tongue 18a. Small ribs 32 are disposed directly adjacent to their respective large rib 31a, 30a on the side thereof that is proximate to central axis c. Each small rib 32 extends from bottom edge 40a for a distance that is about 3/10th the length of the large ribs 31a, 32a. Each small rib 32 is about 2 times the thickness of tongue 18a and about 1/10th the width of tongue 18a.

FIG. 4B illustrates a second arrangement of ribs for a tongue 18b. As shown, tongue 18b is rectilinear in shape with a bottom edge 40b, a top edge 41b, and side edges 42b, 43b. Bottom edge 40b is substantially linear with a central point 45b and corners 46b, 47b at which the proximate ends of respective side edge 42b, 43b meet. Top edge 41b is curvilinear with an apex 48b and corners 49b, 50b at which the distal ends of respect side edges 42b, 43b terminate. Central point 45b and apex 48b lie along central axis c (see FIGS. 2, 4A). The distance between central point 45b and apex 48b is the length of tongue 18b, while the distance between corners 49b, 50b is the width of tongue 18b. The thickness 51b of tongue 18b is the distance between the top and bottom surfaces thereof. Side edges 42b, 43b each has a respective large rib 31b, 32b extending along the entire length thereof. Large ribs 31b are each about 3 times the thickness of tongue 18b and about ⅕th the width of tongue 18b. Small half-ribs 33b, 34b are disposed directly adjacent to their respective large ribs 31b on the sides thereof that are proximate to central axis c. A small rib 35b is disposed along central axis c. Each small half-rib 33b, 34b extends from bottom edge 40b a distance that is about 3/10 the length of the large ribs 31b. Each small half-rib 33b, 34b is about 2 times the thickness of tongue 18b and about 1/20th the width of tongue 18b. The small rib 35b extends from bottom edge 40b a distance that is about 3/10 the length of the large ribs 31b. The small rib 35b is about 2 times the thickness of tongue 18b and about 1/10th the width of tongue 18b.

Figures 4C, 4D:
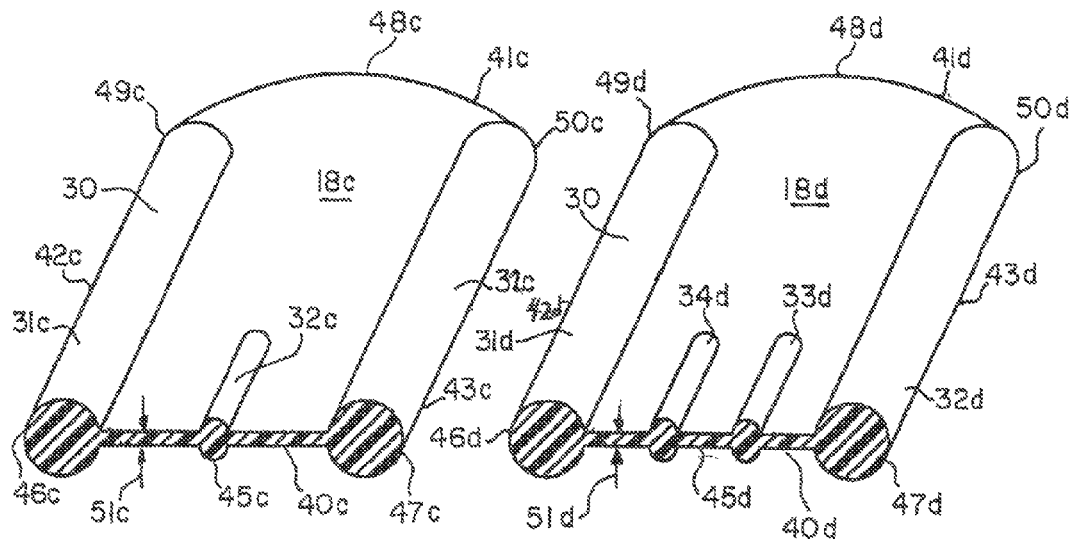
FIG. 4C is a perspective view of a third preferred tongue member for an applicator tip for the dispensing applicator of FIG. 1.
FIG. 4D is a perspective view of a fourth preferred tongue member for an applicator tip for the dispensing applicator of FIG. 1.

FIG. 4C illustrates a third arrangement of ribs for a tongue 18c. As shown, tongue 18c is rectilinear in shape with a bottom edge 40c, a top edge 41c, and side edges 42c, 43c. Bottom edge 40c is substantially linear with a central point 45c and corners 46c, 47c at which the proximate ends of respective side edge 42c, 43c meet. Top edge 41c is curvilinear with an apex 48c and corners 49c, 50c at which the distal ends of respect side edges 42c, 43c terminate. Central point 45c and apex 48c lie along central axis c (see FIGS. 2, 4A). The distance between central point 45c and apex 48c is the length of tongue 18c, while the distance between corners 49c, 50c is the width of tongue 18c. The thickness 51c of tongue 18c is the distance between the top and bottom surfaces thereof. Side edges 42c, 43c each has a respective large rib 31c, 32c extending along the entire length thereof. Large ribs 31c, 32c are each about 3 times the thickness of tongue 18c and about ⅕th the width of tongue 18c. A small rib 35c is disposed along central axis c. The small rib 35c extends from bottom edge 40c a distance that is about 3/10 the length of the large ribs 31. The small rib 35c is about 2 times the thickness of tongue 18c and about 1/10th the width of tongue 18c.

FIG. 4D illustrates a fourth arrangement of ribs for a tongue 18d. As shown, tongue 18d is rectilinear in shape with a bottom edge 40d, a top edge 41d, and side edges 42d, 43d. Bottom edge 40d is substantially linear with a central point 45d and corners 46d, 47d at which the proximate ends of respective side edge 42d, 43d meet. Top edge 41d is curvilinear with an apex 48d and corners 49d, 50d at which the distal ends of respect side edges 42d, 43d terminate. Central point 45d and apex 48d both lie along central axis c (see FIGS. 2, 4A). The distance between central point 45d and apex 48d is the length of tongue 18d, while the distance between corners 49d, 50d is the width of tongue 18d. The thickness 51d of tongue 18d is the distance between the top and bottom surfaces thereof. Side edges 42d, 43d each has a respective large rib 31d, 32d extending along the entire length thereof. Large ribs 31d, 32d are each about 3 times the thickness of tongue 18d and about ⅕th the width of tongue 18d. Spaced apart from each large rib 31d, 32d is a respective small rib 33d, 34d. The small ribs 33d, 34d are preferably, but not necessarily, spaced apart from each other and evenly spaced from central axis c. The small ribs 33d, 34d are closer to central axis c than to their respective large ribs 31d, 32d. The small ribs 33d, 34d extend from bottom edge 40b a distance that is about 3/10 the length of the large ribs 31d, 32d. The small ribs 33d, 34d are about 2 times the thickness of tongue 18b and about 1/10th the width of tongue 18b. Each small rib 33d, 34d is preferably spaced apart from the central axis c by a distance that is approximately equal to its respective width. The small ribs 33d, 34d are spaced apart from each other by a distance that is approximately equal to 2 times the width of either small rib 33d or 34d. Each small rib 33d, 34d is preferably spaced apart from its respective large rib 31d, 32d by a distance that is approximately equal to 2 times its respective width, but other distances may be utilized.

Figure 5A:
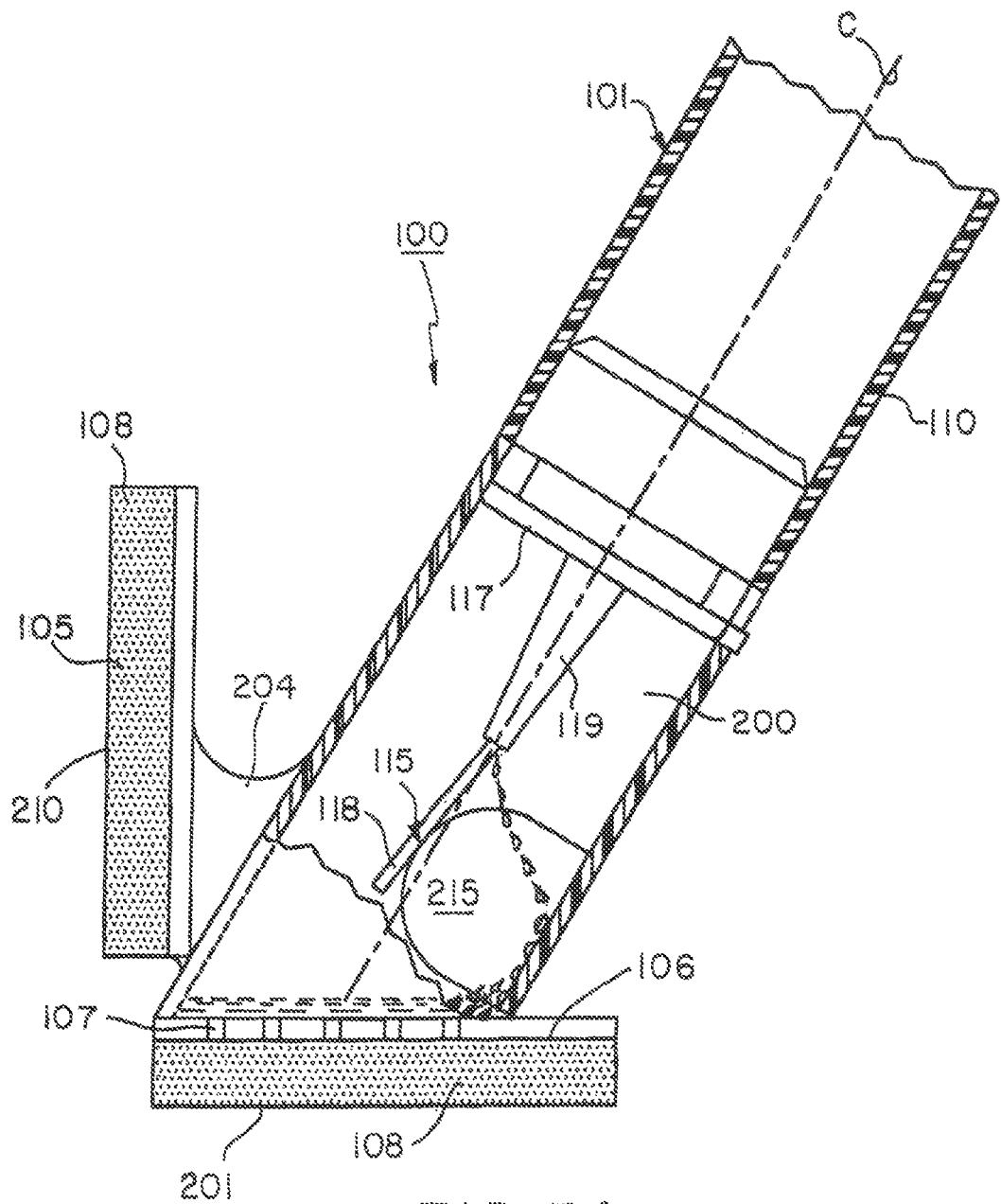
FIG. 5A is a side cross-sectional view of a dispensing applicator constructed in accordance with a further embodiment of the invention.

FIGS. 5A and 5B illustrate a second dispensing applicator 100 according to the present invention. Dispensing applicator 100 comprises an applicator head 108, a source of fluid, which is shown as a hollow, generally cylindrical body 110, and an applicator tip 115, which has an attachment member 117 and tongue member 118 joined thereto by a tapered frangible juncture member 119 having fracture sites as noted above at 12 (see FIG. 3C). Fluid source body 110 and applicator tip 115 are respectively identical in form and function to fluid source body 10 and applicator tip 15 described hereinabove in reference to FIGS. 1 through 4D.

In addition, dispensing applicator member 100 is provided with an absorbent swab member 201, and an inwardly projecting ridge-shaped member 215 provided within body 110. A portion of body 110 is adapted to hold and/or support absorbent applicator member 105. As shown, absorbent applicator member 105 is held and supported on a surface 106. Surface 106 is provided with at least one aperture 107, such that the fluid may flow from the interior of body 110 into absorbent applicator member 105, as discussed in further detail herein below. Furthermore, a portion of body 110 is adapted to hold and/or support absorbent swab member 210.

As shown, absorbent swab member 210 is held and supported on a surface 203 that is connected to body 110 by a stock member 204. Absorbent swab member 210 is preferably not in fluid communication with the interior of body 110. Outer surface 201 of absorbent applicator member 105 is oriented relative to body 200 such that, when absorbent applicator member 105 is substantially parallel to an application surface (i.e., in contact with the application surface), the central axis c of body 110 forms an angle of about 45° with the application surface, which angle provides a comfortable grip for the user and facilitates the flow of fluid through the interior of body 110 into absorbent application member 105. Similarly, absorbent applicator member 105 of absorbent swab member 210 is oriented relative to body 200, such that, when absorbent swab member 210 is substantially parallel to an application surface (i.e., in contact with the application surface), the central axis c of body 200 forms an angle of about 30° with the application surface, which angle provides a comfortable grip for the user and allows the user to spread the applied fluid over a relatively large area with relatively less arm movement and/or extension.

The manner of utilizing dispensing applicator 100 involves holding the dispensing applicator 100 with the absorbent application member 105 against an application surface. Downward pressure of applicator 100 against the application surface will displace head 108 upwardly and force ridge-shaped member 215 into contact with tongue member 118. Sufficient upward pressure of ridge-shaped member 215 against tongue member 118 will upwardly deflect the tongue member 118 from the central axis c of the fluid source body 110. At a predetermined amount of deflection, the frangible juncture 119 will fracture or break at apertures 12 (see FIG. 3C), but not along the entire hinge region or at strengthening ribs (not shown) preventing unintended separation. Fracture of the frangible juncture 119 will desirably be achieved by the application of approximately 0.25 to 5 pounds of downward force of applicator 100 against the application surface. Breaking frangible juncture 119 will result fluid from fluid source body 110 flowing into head 108 via apertures 12 (not shown, but noted in FIGS. 3A-3C). Comparable to breaking frangible region 19 of applicator tip 15, as discussed herein above in reference to FIGS. 3A to 3C, breaking frangible region 119 of applicator tip 115 results in the formation of one or more apertures in applicator tip 115 through which fluid from source body 110 may flow into head 108 without the unintended separation of the tip member 115. Thus, in general, applicator tip 15 is comparable in form and structure to applicator tip 115.

Absorbent swab member 210 may be employed for a variety of purposes. Swab 210 may be used to spread a fluid over the application surface after the application member 105 initially applies the fluid. Using swab 210 in this way would be particularly advantageous if the amount of fluid that is desired to cover a relatively large surface area has been inadvertently applied to a relatively small area, which may occur if application member 105 becomes over-saturated with fluid and can no longer effectively regulate the flow rate and amount of fluid being applied. Moreover, swab member 210 may be used to soak up fluid on the application surface, for example, when an excess of fluid has been applied or the fluid has been applied over the wrong area.

As stated above, absorbent swab member 210 is preferably not in fluid communication with the interior of body 200. However, a possible use for swab 210 is applying fluid to a second surface area that is separate and apart from the surface area over which used absorbent application member 105. In the critical interest of avoiding cross-contamination, it is desirable to use the application member 105 over only a single contiguous surface area that should be relatively limited (e.g., the upper front of the torso, instead of the entire front of the torso). Accordingly, after an initial application, any additional fluid in a given dispensing applicator may go wastefully unutilized. Therefore, in another embodiment of absorbent applicator head 108, there is provided at least one aperture (not shown) in surface 203, such that fluid may flow from the interior of body 200 into absorbent swab member 210.

Head 108 may be detachable from fluid body 110. Fluid body 110 may contain an amount of fluid that is greater than is necessary for a given application. Accordingly, after an initial application, any additional fluid in a given dispensing applicator may go wastefully unutilized. Therefore, in another embodiment of applicator 100, fluid body 110 is removably attached to head 108 so that head 108 may be disposed of separately from fluid body 110. If fluid body 110 contains residual fluid after an initial application, other absorbent head may be attached to fluid body 110, thereby allowing the residual fluid to be applied to another application surface.

Figure 6:
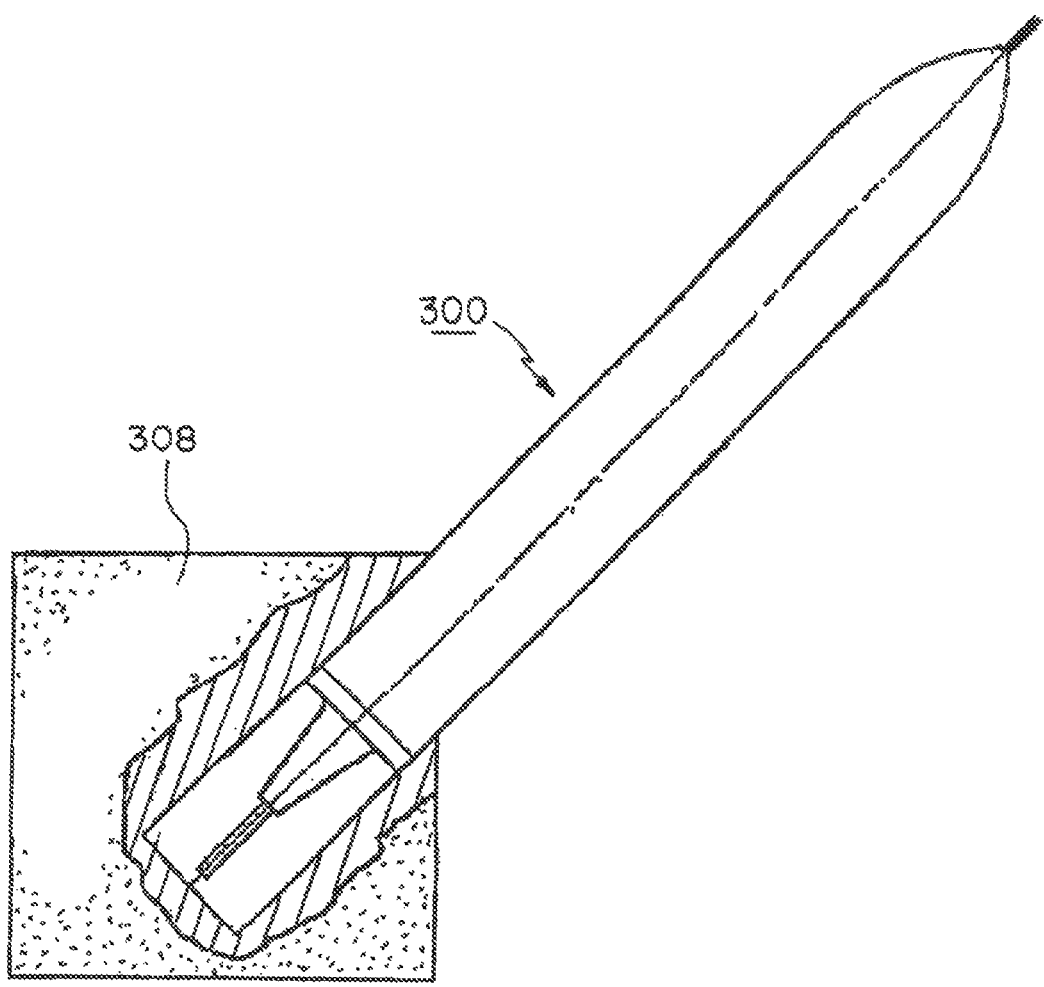
FIG. 6 is a side cross-sectional view of a dispensing applicator structured in accordance with a further embodiment of the present invention and showing a side cross-sectional view of the applicator tip.

Referring to FIG. 6, as stated above, it is desirous to avoid cross-contamination by using a given absorbent applicator over only a single contiguous, relatively limited, surface area. Yet, using a given absorbent application in such a manner will often result in an amount of fluid therein being wasted. Accordingly, a dispensing applicator according to the present invention, generally indicated as reference numeral 300, may be provided with a relatively larger, multi-sided absorbent applicator member 308, such that different sides thereof may be used on different surface areas.

Figure 7:
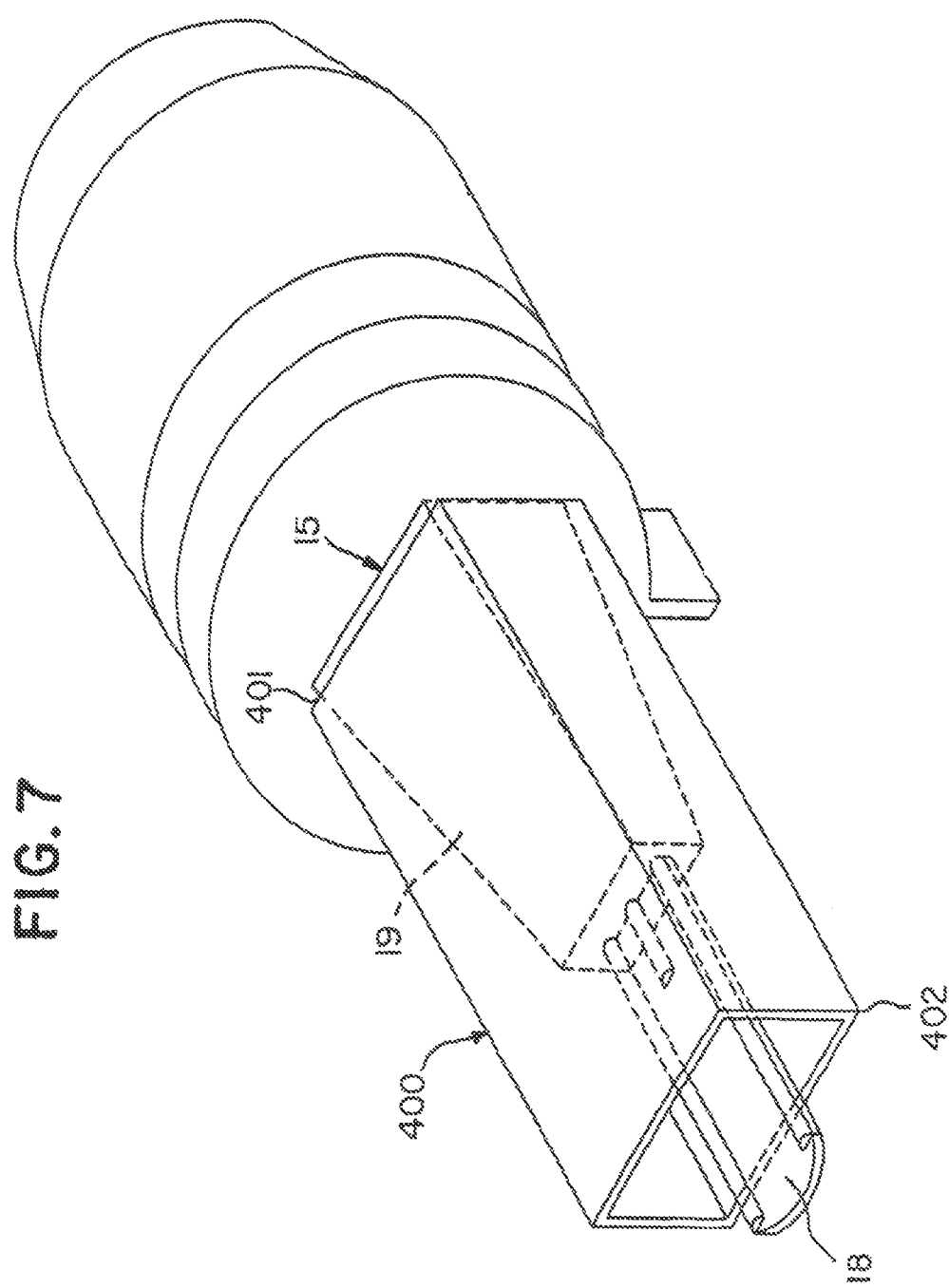
FIG. 7 is a perspective detail view of an applicator tip for use in a dispensing applicator according to the present invention having a semi-cover surrounding the frangible portion to control the speed and direction of the dispersion of the fluid into the absorbent member.

Referring to FIG. 7, there is shown an applicator tip having a semi-permeable or non-permeable cover 400 substantially surrounding frangible juncture 19. The purpose of cover 440 is to control the speed and direction of the dispersion of fluid in a surrounding absorbent member (not shown). Preferably, a rearward edge 401 of cover 400 will be attached to applicator tip 15. More preferably, rearward edge 401 will be fully sealed around applicator tip 15 without gaps or holes so that fluid may not flow rearward under edge 401. If cover 400 is semi-permeable adjacent to rearward edge 401, fluid may flow rearward through cover 400, but preferably will not flow rearward under edge 401 given the more preferable fully sealed attachment thereof to applicator tip 15. In contrast, a forward or distal edge 402 of cover 400 is preferably free and unattached to applicator tip 15 so that fluid may flow forward under cover 400 substantially without being impeded thereby.

Preferably, cover 400 is formed as a seamless, unitary cylindrical sleeve (e.g., having a circular, square, or rectangular cross-section). Nonetheless, cover 400 may be of any suitable shape and construction. Depending upon its intended function, cover 400 may be semi-permeable or impermeable to fluid. Cover 400 may be made of various materials, including natural and/or synthetic rubbers, thermoplastics (e.g., polyethylene), cellulosic materials or similar fibers (i.e., natural polymeric fibers), and metallic materials. Cover 400 may be a contiguous sheet, a mesh, a felt, or another suitable form, with or without reinforcing fibers and/or seams (i.e., "rip-stop" seams). Also preferably, cover 400 is pliable and flexible so that it does not impede deflection of tongue member 18. In other words, it is preferable that cover 400 does not hinder the breaking of frangible juncture 19.

However, surrounding frangible juncture 19 with a cover 400 having suitable thickness and/or stiffness will provide a level of reinforcement that prevents inadvertent breaking of frangible juncture 19. Accordingly, by employing a suitable thick and/or stiff cover 400, tongue member 18 may be provided without reinforcing ribs. Thus, employing cover 400 to reinforce frangible juncture 19 will advantageously simplify production of application tip 15, since tongue member 18 may be molded as a simple flat extension.

Figure 8:
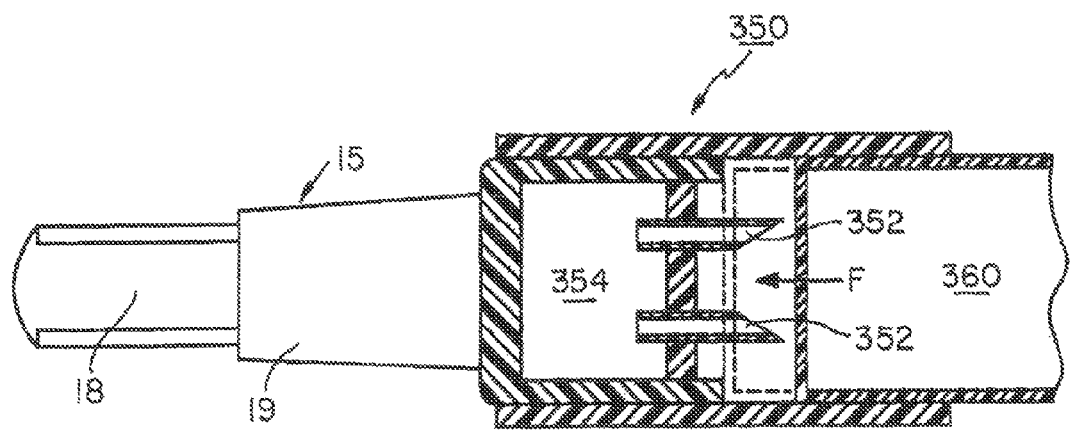
FIG. 8 is a top cross-sectional view of a further aspect of an embodiment of an applicator according to the present invention.

Controlling a rate of dispensing fluid is critical because a) over saturation of the absorbent member reduces the collecting capability of this member, and b) back flow of the delivered fluid from the distal end towards the proximal end of the absorbent member interferes with the physician's work. Accordingly, FIG. 8 illustrates a further embodiment of the invention directed to a dispensing applicator 350 which is configured to prevent fluid from uncontrollably entering an attachment member 354 that is coupled to tip 15. At least one, but preferably a multiplicity of capillary vessels 352 is provided within the attachment member. Being in fluid communication with a source body 360, vessels 352, by virtue of their cross-section, meter an amount of fluid penetrating into the absorbent member (not shown). Thus, a combination of the openings, which are formed as a result of breaking frangible region 19 and vessels 352, effectively limits oversaturation of the absorbent member.

Figure 9:
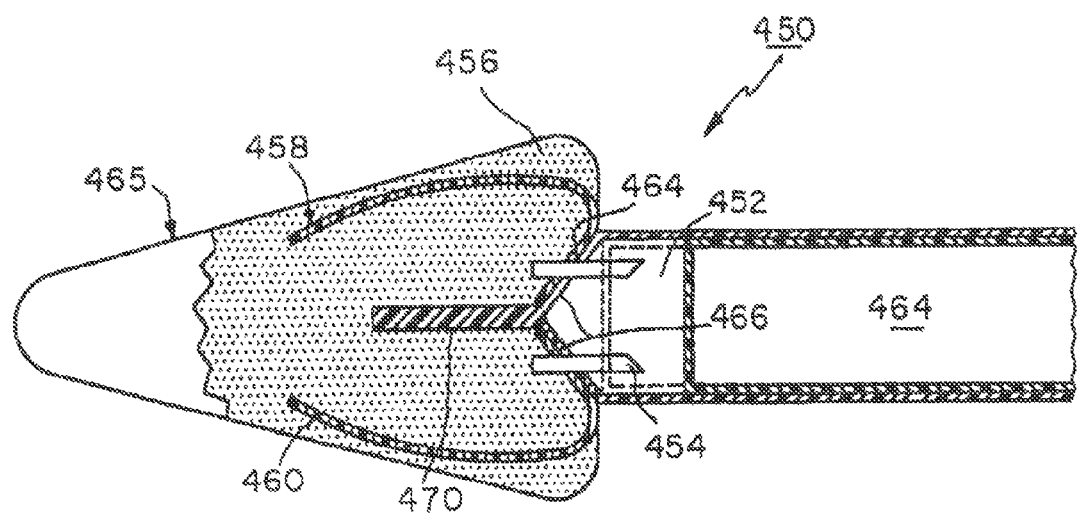
FIG. 9 is a side cross-sectional view of another aspect of an embodiment of the dispensing applicator configured with a collecting and guiding means for minimizing unintended evacuation of fluid via a proximal end of a fluid absorbent member enabling a preferred directional fluid flow.

Still another embodiment of a dispensing applicator 450 is illustrated in FIG. 9. As shown, applicator 450 does not have a frangible structure or region. Instead, an attachment member 452 is provided with at least one or more capillary vessels 454 controllably traversed by fluid from fluid source 464. Vessels 454 project into an applicator tip 465 while penetrating a proximal end of an absorbent member 456. The cross-section of the vessels is selected to provide a metered delivery of fluid.

However, absorbent member 456 can still accumulate an excessive amount of fluid, which will eventually result in a backflow towards the proximal end of the absorbent member and subsequent voluntary evacuation of fluid via this end. To limit or minimize such a possibility, applicator 450 has a flow limiting component or cover 458. Formed within absorbent member 456 and, preferably, sealed to the proximal end thereof, cover 458 is able to collect fluid flowing towards the proximal end of absorbent member 456 and, thus, prevents uncontrollable evacuation of accumulated fluid.

As illustrated, cover 458 is provided with a body having a pair of concave sides 460 whose free or distal ends are spaced from one another at a distance that defines an open exit/entrance for fluid. The bottom portions 464 of cover 458 extend complementary to converging flanks 466 of attachment member 452. Stability of an applicator tip 465 is added by providing the distal end of attachment member 452 with a rib 470. Note that cover 458 does not completely prevent backflow of fluid leaving a space within the absorbent member which is sufficient to amply, but not excessively, wet the surfaces of this member.

Figure 10A:
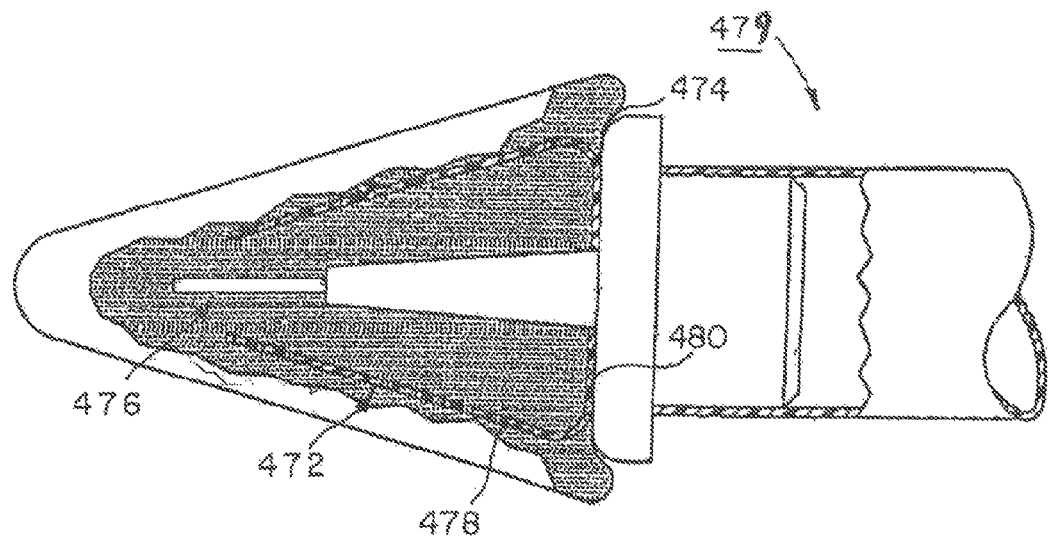
FIG. 10A is a side sectional view of still another embodiment of the present invention.
Figure 10B:
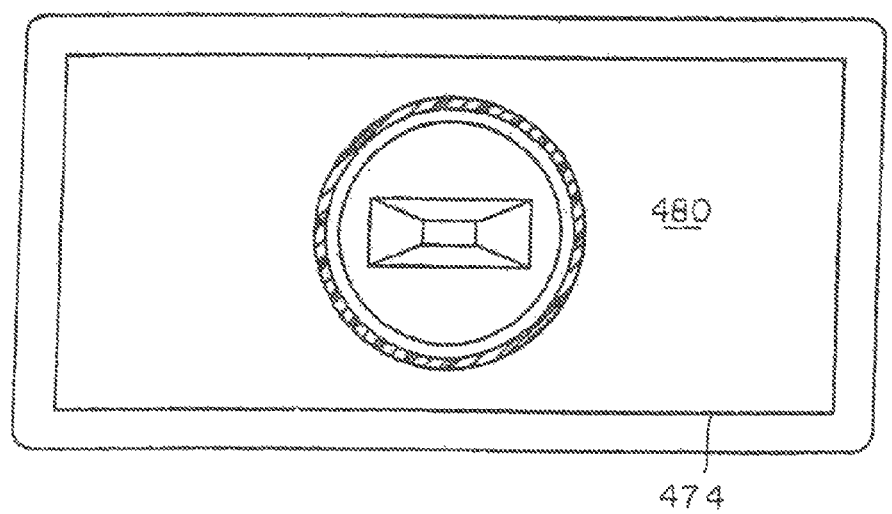
FIG. 10B is a rear sectional view of the embodiment shown in FIG. 10A.

A further embodiment of dispensing applicator 479 is illustrated in FIGS. 10A and 10B. Applicator 479 has a frangible region 19 structured substantially similar to the like configured regions which are discussed in detail above. To prevent uncontrollable evacuation of fluid via a proximal end 474 of an absorbent member 476, applicator 479 has a cover 472 functioning similarly to cover 458 of FIG. 9. However, cover 472 is configured with a pair of rectilinear flanks 478 and a bottom portion 480 that extends parallel to a flat distal end of attachment member 17. Cover 472 may also be cone-like. The applicator 479 is formed by inserting cover 472 into and sealing it to the interior of absorbent member 476. The bottom portion 480 lies preferably flush with the proximal end of the absorbent member and is sealingly attached to frangible region 19.

Figure 11A:
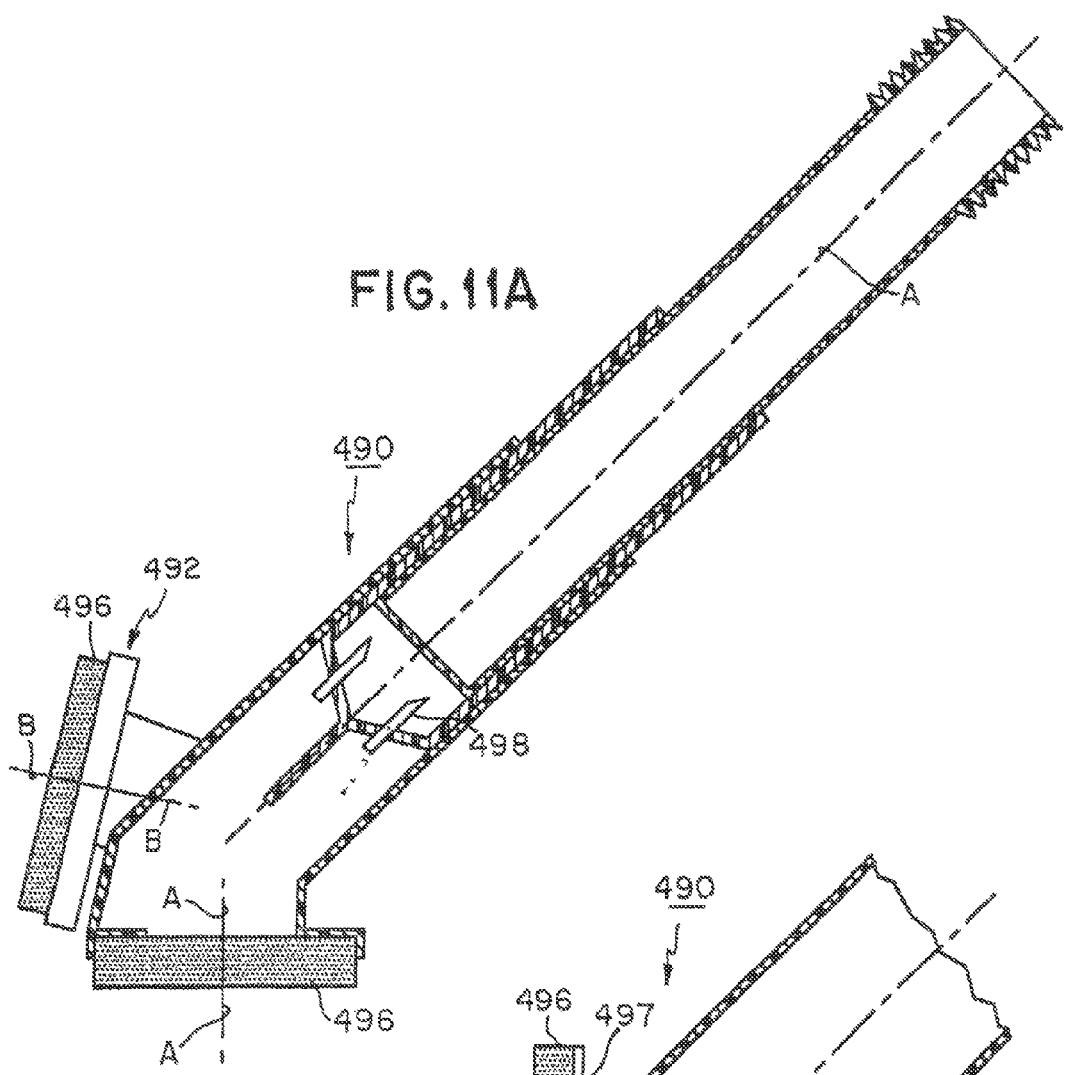
FIG. 11A is a side cross-sectional view of another dispensing applicator according to the present invention.
Figure 11B:
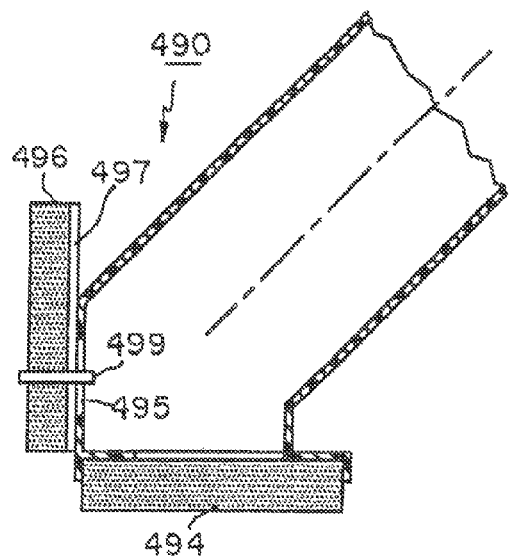
FIG. 11B is a side cross-sectional view of a further aspect of an embodiment of the dispensing applicator according to the present invention.
Figures 12, 13:
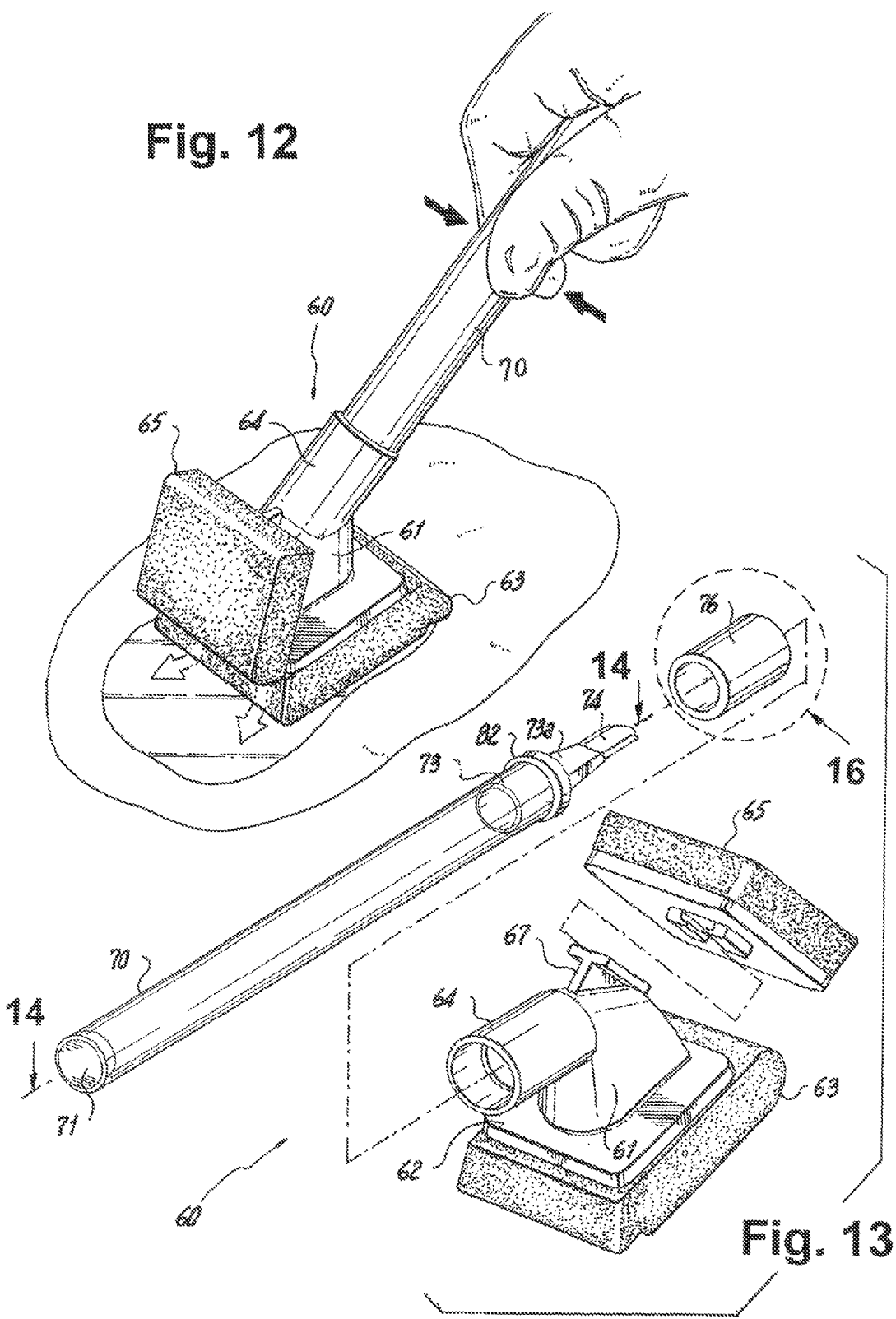
FIG. 12 is a left front side perspective view of another embodiment of dispensing applicator wherein a fluid containing source is receivably attachable to an applicator mounting body stem piece in snap fit connection therewith, initiation of fluid flow being effected with a relative rotational movement between the fluid source container and a fracture anvil in the mounting body.
FIG. 13 is a right side exploded view of the dispensing applicator shown in FIG. 12.

Embodiments of a dispensing applicator 490 illustrated in FIGS. 11A and 11B are conceptually close to the embodiment illustrated in FIGS. 5A and 5B and include an applicator head 492 which is formed with an absorbent member 494 and a swab member 496. The absorbent and swab members have a center axes A-A and B-B, respectively, which intersect one another forming an angle of about 80-100o.

The difference between the embodiment of FIGS. 5A and 5B and the one in FIGS. 11A and 11B includes utilization of one or more capillary vessels 498 provided instead of the frangible region. While, swab member 496 of FIG. 11A is prevented from fluid communication with an interior of a fluid source body, swab member 496 of FIG. 11B is traversed by a capillary tube 499 and has an inner surface 497 in fluid communication with the interior via an opening 495, for the reasons explained above in reference to FIGS. 5A and 5B.

Another embodiment of the dispenser is depicted in FIGS. 12-27. With reference to those Figures, dispensing applicator 60 comprises a mounting block 66 having a base piece 61, a bottom side skirt part 62 to which is affixed an absorbent sponge type applicator 63, and a tem piece 64 upstanding from base piece 61. An absorbent swab 65 is carried at an adjacent side of the mounting block 66, for which purpose the mounting block 66 includes a mounting bracket 67 (depicted to advantage in FIG. 18) receptive of a skirt piece 68 to which swab 65 is affixed. Stem piece 64 is preferably a tubular component and its interior space is in communication with the interior space 69 of base piece 61 (see FIG. 21), the last mentioned space outletting to absorbent applicator 63 so that a flow course in the mounting block 66 has inlet in the stem piece 64 and outlet at applicator 63. An elongated fluid container 70 is attachable to the mounting block, an end of the container being received in stem piece 64.

Referring in more detail to FIGS. 12-17, container 70 which is of tubular configuration is capped at a first end as at 71. At a distal opposite end length, an attachment number 72 has a length portion, as at 73, received inside the container; and, the length portion is affixed to the container as, for example, by heat sealing. The length portion has a flange 80 thereon and a continuing length portion 73a constituting a frangible section, this section transitions into a tongue element, 74. The juncture of the tongue element 74 and the continuing length portion 73a defines a weakened joinder location at which the fracture and at least partial separation of the tongue element from the frangible section will occur, enabling outletting of fluid from container 70.

As shown in FIGS. 16 and 17, depicted is one embodiment of a fracture anvil 76. The fracture anvil has a cruciform passage 77 extending therethrough, as well as a number of fluid pass-through passages 78 for enabling fluid released on fracture to flow toward absorbent applicator 63. When the second opposite end of the container 70 is inserted into the stem piece 64, the tongue element is aligned such that it will enter and locate in the cross passage part 77a of cruciform passage 77, the fracture anvil having been inserted in the bore 72 of the stem piece. The second opposite end of the container 70 is snap fit connected to the stem piece 64. The arrangement is such that with flange 80 received in annular internal groove or slot 154 in the stem piece (see FIG. 21), the tongue element 74 is properly positioned in cross passage part 77a for effecting fracture.

External dimensioning of the annular flange 80 and internal groove 154 is such that the container 70 can be rotated relative to the fracture anvil while the fracture anvil is held. This approximately ninety degree rotation of the container is effective to twist the tongue element 74 at the weakened joinder location with length portion 73a, fracturing it and effecting at least partial separation from length portion 73a. With this fracture, fluid releases from the container into the mounting block through course. FIGS. 21-22 and FIGS. 23-24 show, respectively, pre and post-fracture orientations of length portion 73a.

Figure 25:
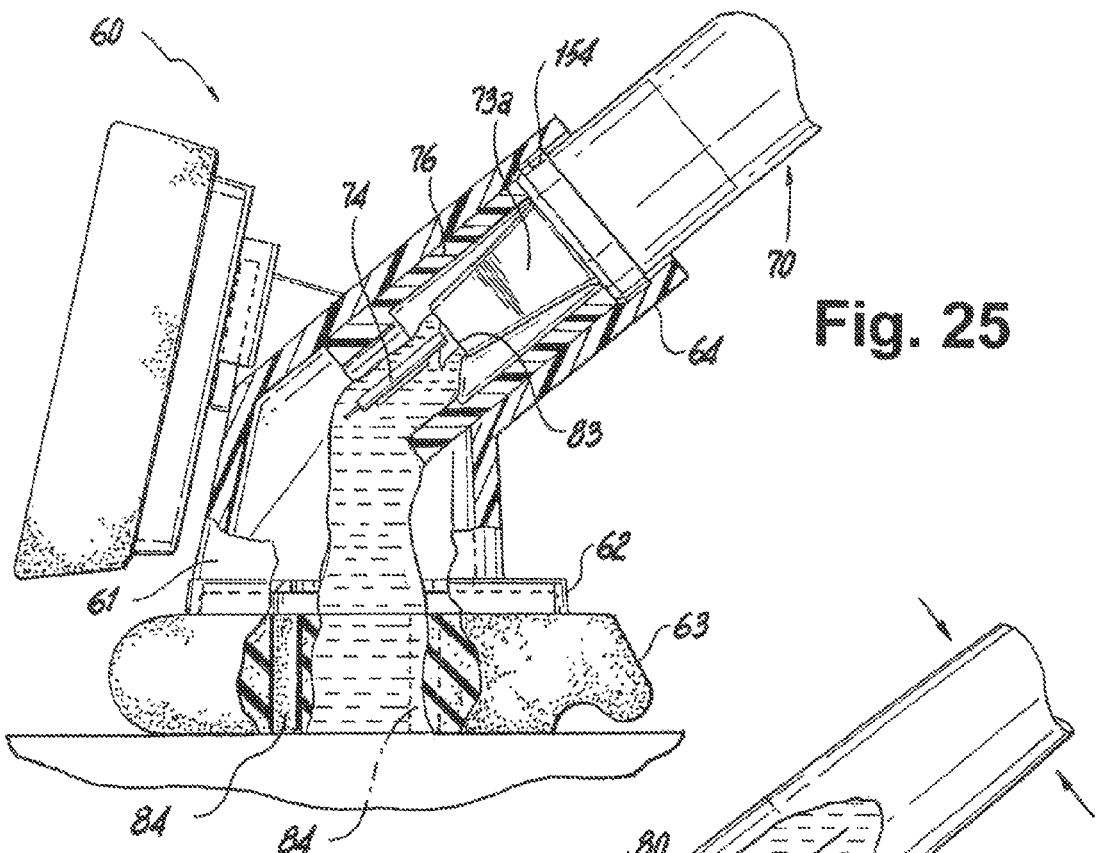
FIG. 25 is a view similar to FIG. 23 except it is more broken away to depict how on occurrence of fracture of the frangible piece fluid starts to flow from the apertures at the fracture point and disperses through the absorbent applicator.
Figure 26:
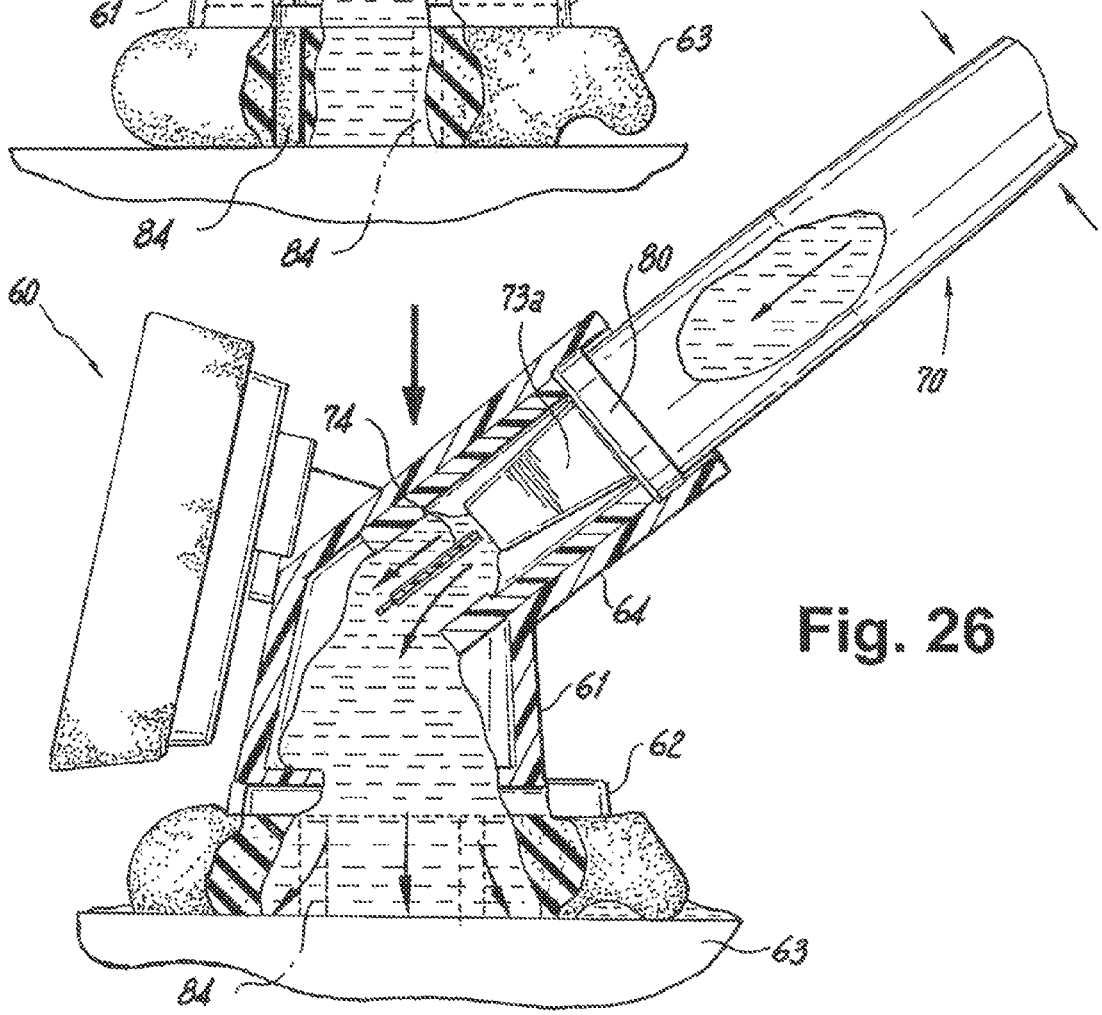
FIG. 26 is a view similar to FIG. 25 but showing a more profuse flow of fluid occurring following fracturing of the frangible piece.
Figure 27:
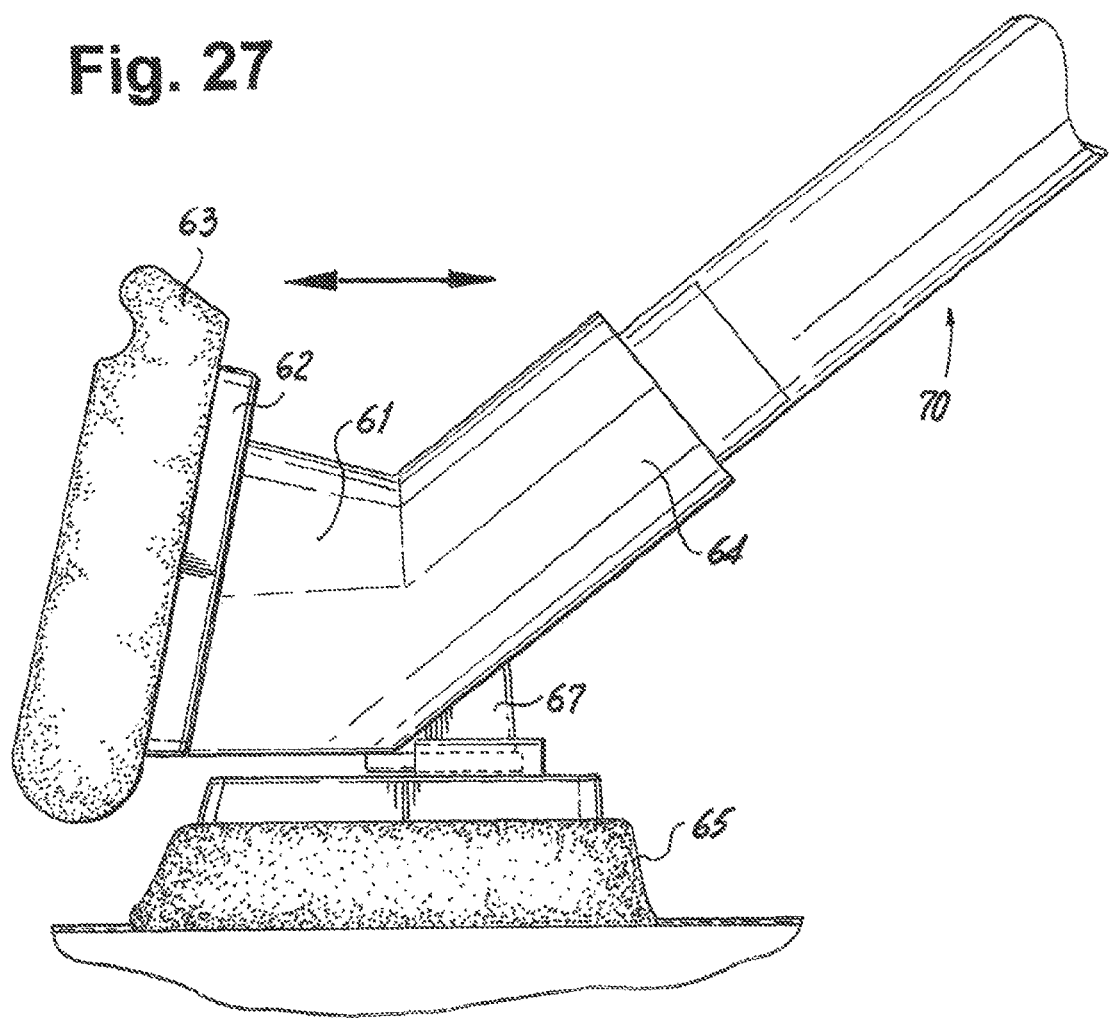
FIG. 27 is a left side view of the applicator dispenser depicting the orientation of the mounting block to present an absorbent swab to a position for use thereof.
Figure 28:
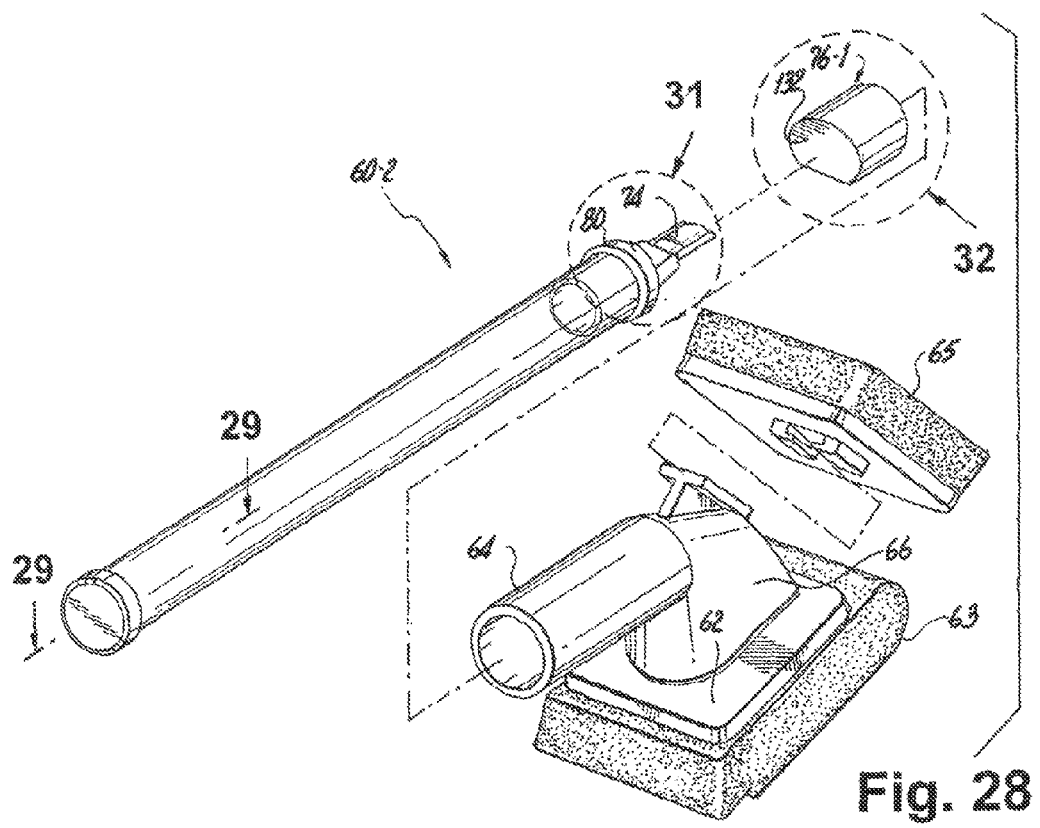
FIG. 28 is a right side exploded perspective view of another embodiment of a dispenser employing a fracture anvil for fracturing the tongue element at its joinder point with the frangible length thereby to initiate release of the container contents into the absorbent applicator.
Figures 32, 33, 34:
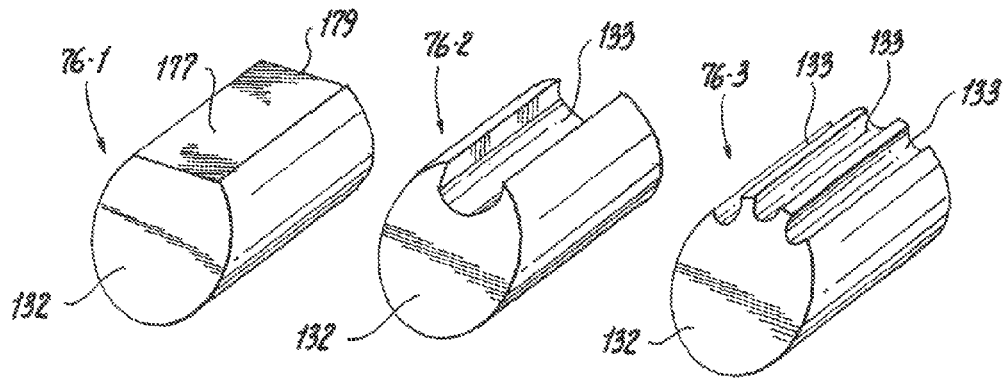
FIG. 32 is a perspective view of a fracture anvil shown in circle 32 of FIG. 28, depicting detail of a first form of truncated cylindrical fracture anvil wherein a flat chord face is formed in the anvil cylindrical periphery to define with an inner encircling wall face of the stem piece, a flow channel in the mounting block through which the fluid contents communicate from the ruptured container to the absorbent applicator.
FIG. 33 is a perspective view of a second form of fracture anvil is provided with a gutter-like fluid contents flow channel at its cylindrical periphery.
FIG. 34 is a perspective view of a third form of fracture anvil wherein its periphery is provided with plural gutter-like fluid contents flow channels at its cylindrical periphery.
Figure 35:
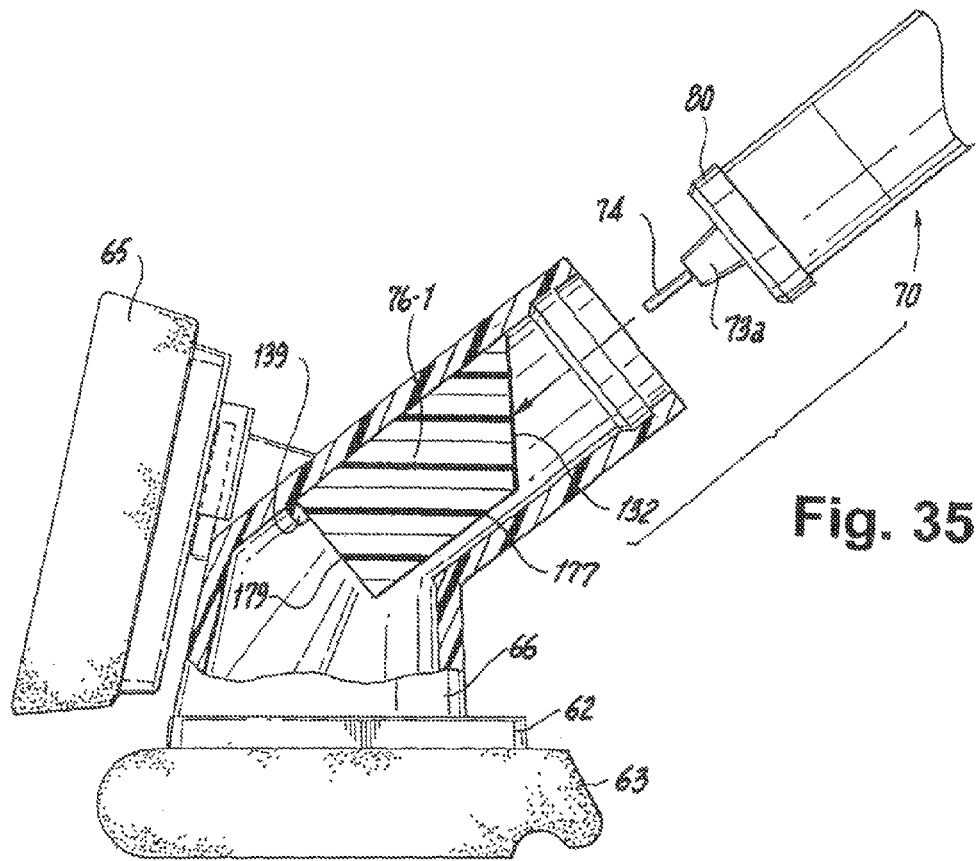
FIGS. 35-37 are side views partly in sections of the applicator showing the urging direction travel of the container to engage the tongue element against the inclined end fracture face of the fracture anvil to effect fracture of the tongue element at its joinder to the frangible section, the moved fractured position of the tongue element being depicted in dashed lines, and the release of fluid flow about the securely retained but fractured section.

Looking at FIG. 25, shown is how fluid outlets the container in streams from apertures 83 at the fracture site of tongue element 74 and length portion 73a, the apertures 83 being shown in FIG. 15 as well. Likewise, FIG. 26 shows the pattern of fluid flow to and distributed throughout the absorbent applicator 63, which distribution is promoted by the passages 84 formed in the applicator 63. In FIG. 27 illustrated is the orientation of the dispenser 60 when, e.g., it is desired to swab a large patient area, spreading out the quantity of fluid applied to the patient with absorbent swab 65. And, in FIG. 28 depicted is an embodiment of dispensing applicator 60-2, which is identical with the FIG. 13 applicator 60 except wherein fracture anvil 76-1 is embodied as a truncated cylinder. The anvil 76-1 shown in more detail in FIGS. 32 and 35 is provided with a flat inclined top face 132, and with a flat chord face 177 at the cylindrical periphery thereof and extending between top face 132 and a bottom face 179. With the anvil 76-1 received in stem piece 64 as shown in FIGS. 35-37, flat chord face 177 is disposed spaced from the cylindrical inner surface of the stem piece 64 and therewith defines a flow channel along which fluid contents of container 70 can flow from interior space 99 of the stem piece 64 to the interior space 69 of base piece 61.

Figure 31:
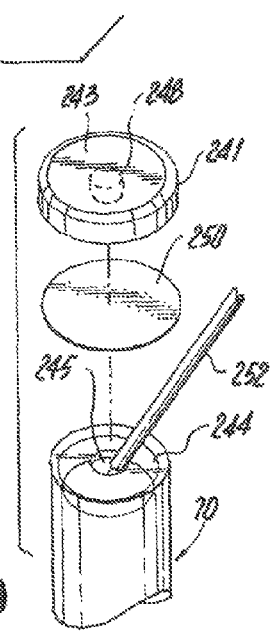
FIG. 31 is a fragmentary perspective view of the applicator tongue element carrying end in circle portion 31 of FIG. 28, depicting the tongue element as fractured separated from the frangible section solely for the purpose of illustrating the apertures from which container fluid contents issue therefrom into the absorbent applicator, it being understood that in the embodiment where the tongue element is fractured with urging against a fracture anvil, it is preferable that the tongue element on fracturing, have retained structure by which it remains attached to the frangible length while still allowing meaningful fluid contents flow.
Figure 36:
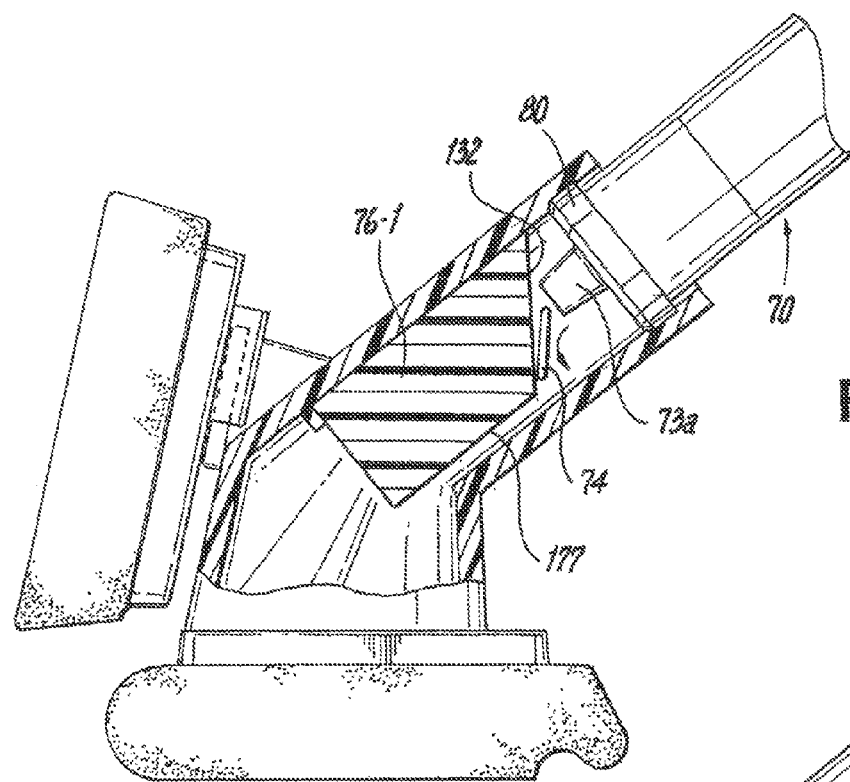
Figure 37:
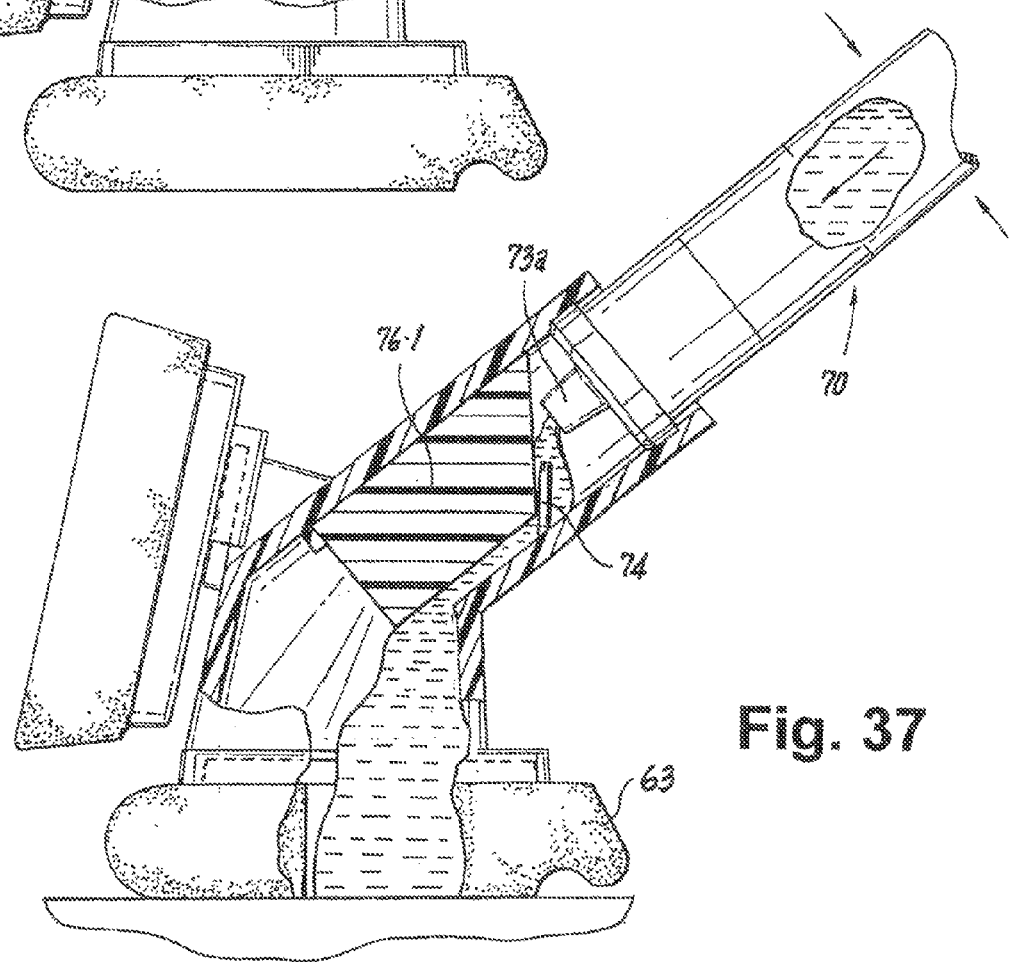

Referring to FIGS. 35-37, explanation of fracturing for fluid flow (but not separation) of the frangible weakened joint at which the tongue element 74 is connected to the frangible length part 73a is now given. The circular inner surface of the stem piece 64 is shouldered or provided with a stop as at 139 to hold the fracture anvil 76-1 (FIG. 32) in stopped position so it cannot move lower in the stem piece passage. When the applicator is to be used, a fluid container 70 will be inserted into the stem piece 64, tongue element 74 first. The tip end of the tongue element 74 will in course of insertion travel strike against the inclined top face 132 of the fracture anvil 76-1 in consequence of which the tongue element 64 will be laterally displaced from the full line position thereof in FIG. 35 to the position as shown in FIGS. 36 and 37. That displacement effects rupture (but not separation) of the tongue element at its joinder location with the frangible region and container fluid contents are released through orifices 83 (FIG. 15) into the stem piece interior space. It is specifically noted, that in FIG. 31 the separation is shown only for purposes of visualizing the openings accessed by fracture of the frangible regions, and it will be recognized that the inner joining region of tongue member 74 remains firmly and securely attached to head member 80, and is merely displaced allowing a fluid-flow access to the openings noted. Thus, FIG. 31 is for illustrative purposes only and does not reflect a separation.

Additional fracture anvil embodiments are shown in FIGS. 33 and 34. In these embodiments, the truncated cylinder anvils 76-2 and 76-3, unlike fracture anvil 76-1, retain their outer surface cylindrical envelopes. Like fracture anvil 76-1, these anvils 76-2 and 76-3 each lave an inclined flat top face 132 and a flat bottom face 179. To provide flow from the inclined top face to the flat bottom face side of the fracture anvils, gutter-like flow channels 133 are formed in the cylindrical periphery of each anvil, these flow channels 133 extending from the inclined top face 132 to the flat bottom face 179. Fracture anvil 76-2 has one flow channel or relatively large cross section area, whereas, fracture anvil 76-3 has plural, i.e., three flow-channels each of smaller cross section area but in total about the same as the cross section area of fracture anvil 76-2. The flow channels 133 juxtapose with the inner encircling periphery of the stem piece and provide ample artery volume to insure proper fluid flow to the absorbent applicator 63

An important consideration in the dispensing applicator is (a) complete filling of container 70 during manufacture to ensure maximum supply and (b) avoidance of contamination of the fluid contents in the container 70 both as to at initial filling of disinfectant and medicaments therein and as to post filling handling and storage until need to use. It will be recognized by those of skill in the art, that achieving (a) will eliminate air pockets prior to use that will impact contamination in (b). In this regard and with continuing reference to FIGS. 29 and 30, the container 70 of dispensing applicator 60-2 is provided at its first or filling end with a capping assembly 240 (as shown) that includes a closure cap 241 having a central disc part 243 and an axially directed peripheral skirt 242 encircling the outer surface of the container 70 at its first end. The first end tip part of container 70 has a radially inwardly directed annular flange 244 defining a central opening 245 (See FIG. 30) in the container tip end. A boss 248 projects axially from the inner face of central disc part 243 and with the cap in place on the container first end, the boss 248 will locate a distance through central opening 245 upon assembly. The capping assembly also includes a, e.g., foil material gasket 250 constructed from a suitable material which is used to intervene the inner side of the closure cap 241 and the first end face, i.e., the annular flange 244 outer face of the container 70.

Figures 29, 30:
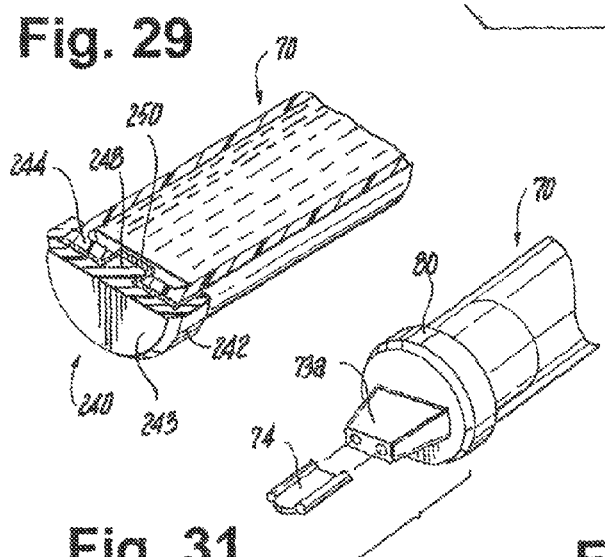
FIG. 29 is a perspective view of a fragmentary length portion of the container in half section taken on line 29-29 in FIG. 28 depicting the manner of the capping of the container contents filling end.
FIG. 30 is an exploded fragmentary perspective view of several components embodied in the capped end structure of the container.

Turning to FIG. 30, shown is a manner of container filling. A filling line 252 (shown as a tube) in the sterile filling operation environment delivers disinfectant or medicament fluid as discussed herein of any suitable kind through central opening 245 into the container until there is overflow of fluid at which point the filling is terminated. Gasket 250 is then set on top of the outer face of flange 244, the gasket being of larger area expanse than flange 244 and makes liquid contact for sealing purposes. Further, gasket 250 is selected from materials which are liquid proof, stretchable or deformable to a certain degree so that when closure cap 241 is fitted over the first end of the container sandwiched between the closure cap inner face and the outer face of flange 244, an air tight joint seal of the container is effected without a bubble, since the gasket material will conform to the sandwiching structure in intimate contact therewith. FIG. 29 illustrates this clearly and employs a formed main tube body 70 having only smaller opening 245. It is also to be noted from FIG. 29 that fluid fills the first end of the container 70 and is in air excluding contact with the gasket, and the apparent fluid gap in FIG. 29 is employed only to show depth of the fluid and not the existence of an unfilled portion of the tube. This arrangement assures absence of any possible contaminants-containing air within the container. It is preferred that the closure cap 241 once in place be not removable from the container. This can be effected by sonic welding or other attachment means of the closure cap to the container and optionally of the foil closure itself. If it is thought expedient for any reason, the cap can be removably snap fitted to the container. For example, an annular groove in one of the structure inner skirt surface and outer surface of the container, and an annular bead on the other of said surfaces will allow removal the closure cap but only with deliberately intended such action.

Figure 38:
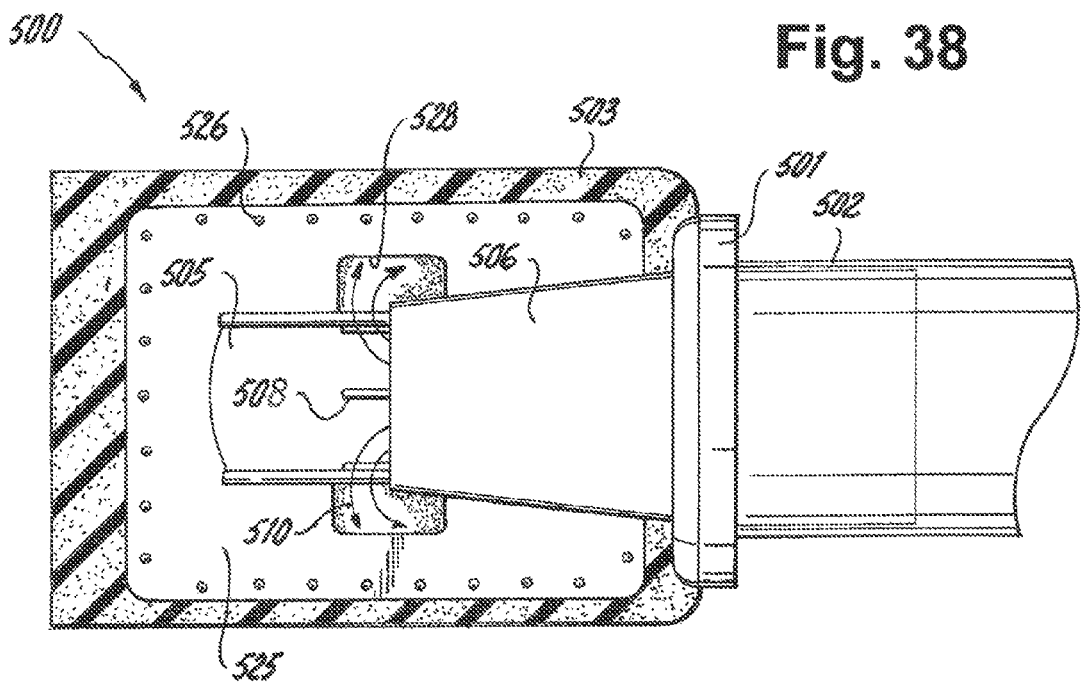
FIG. 38 shows a top cross-section view of an alternative construction of a dispenser system containing a head member secured to a dispensing fluid container and surrounded by a foam dispersing member.
Figure 39:
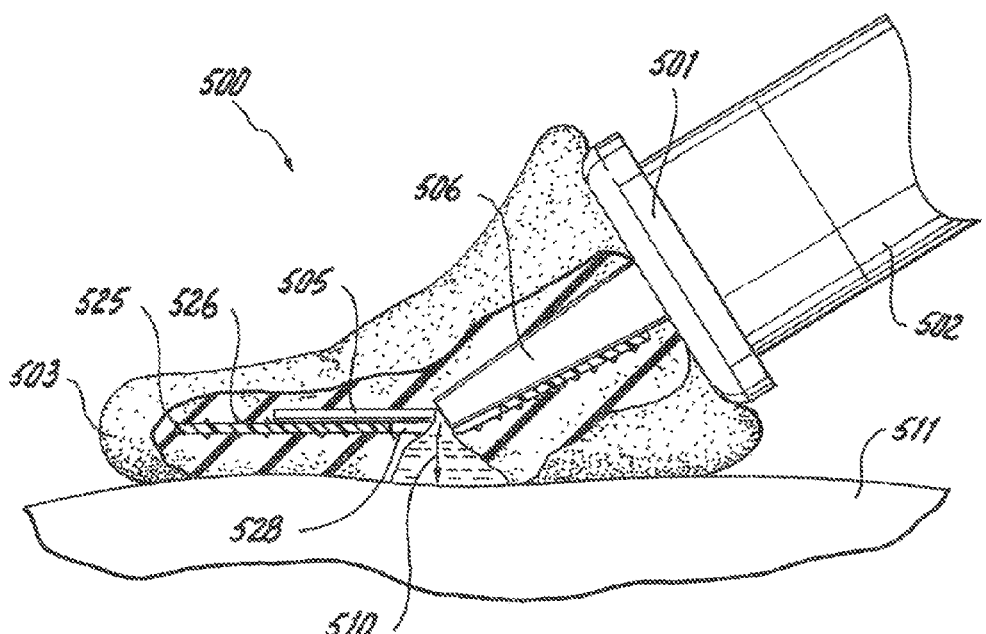
FIG. 39 shows a side of the dispenser system of FIG. 38 during use.
Figure 40:
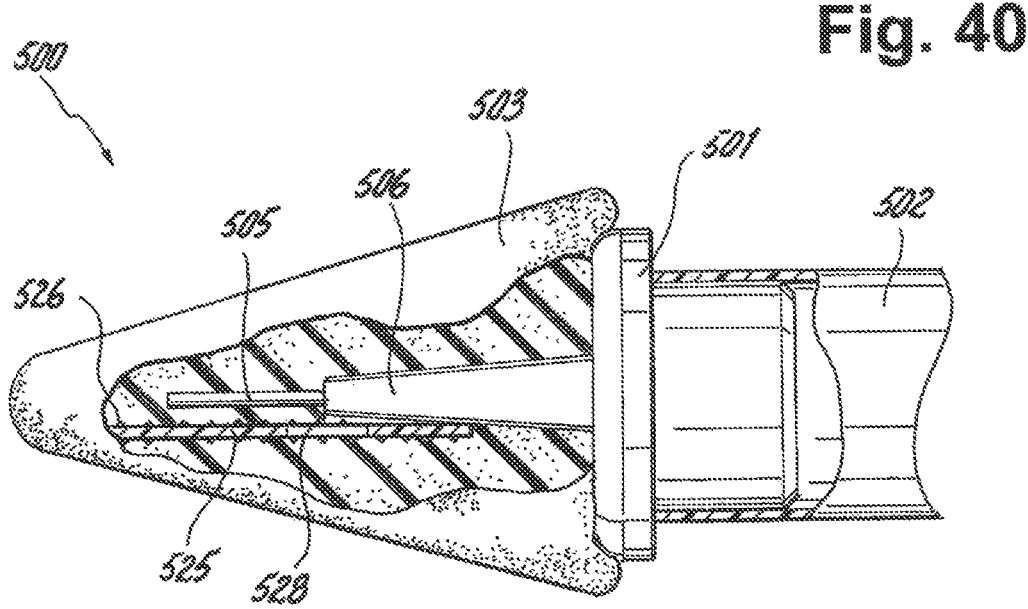
FIG. 40 shows a side partial cross-section view of the dispenser system of FIG. 38.
Figure 41A:
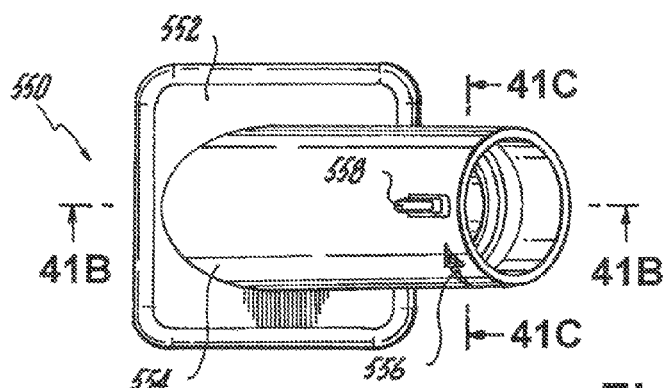
FIG. 41A is a top plan view of an alternative embodiment of a mounting block for a fluid dispensing applicator according to the invention which receives an absorbent applicator at a block bottom side.
Figure 41B:
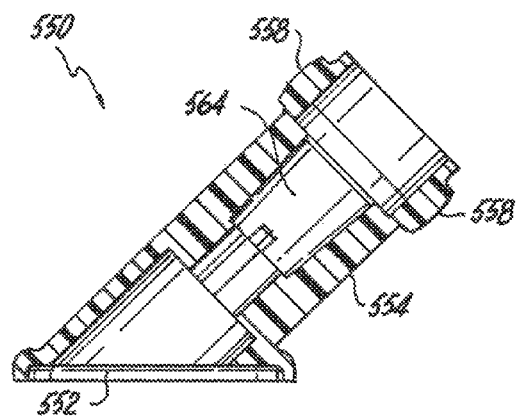
FIG. 41B is a cross-section view taken along the line 41B-41B in FIG. 41A.
Figure 41C:
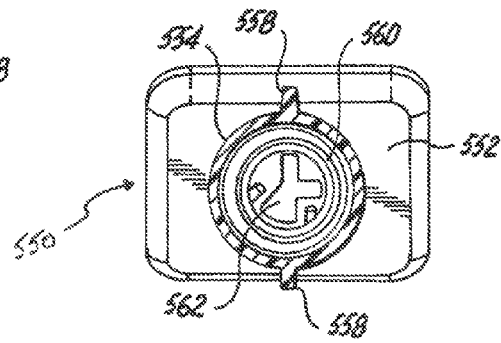
FIG. 41C is a cross-section view taken along the line 41C-41C in FIG. 41A.

Referring now additionally to FIGS. 38-40, an alternative construction is provided at a dispenser system 500 containing a head member 501 secured to a dispensing fluid container 502 and surrounded by a foam dispersing member 503 constructed in a manner previously discussed. As earlier noted, flow shields and flow control devices may be particularly useful in preventing unintended fluid release, fluid spill back during application (from buildup within foam dispersing member 503) etc. Similarly, a flexible tip or tongue member 505 is joined with reinforcing members 508 (shown in the first figure) joined to fracture member 506 on head member 501 so that the fracture about the stressed areas earlier noted (see for example FIG. 3C at 12, the discussion of FIG. 5A and the related discussions of flexible fracture upon movement of the tongue member while retaining and preventing separation of the tongue member) is directionally out the only side that fractures—that facing the application surface as seen by flows in FIG. 39. As a consequence, fluid flows 510 from the fracture or opening site may approach an application surface 511 upon actuation. What is additionally appreciated here, is that, dual surfaces of foam member 503 is substantially beneficial for the reasons noted above.

A flexible plastic card 525 is flexibly retained and fixed in foam applicator head 503 proximate fracture member 506 as shown. Card 525 is formed of a thin, flexible and fluid resistant (impermeable or semi-permeable) material (like a playing card), and includes preferably a plurality of peripheral protuberances or indentations 526 that engage the foam or sponge head to prevent lateral or longitudinal shifting relative to the fracture location for reasons that will be discussed. As will be appreciated, the protuberances 526, spikes, detents or other structures or chemical means (such as glue about the perimeter) may be employed to minimize or prohibit shifting of card shield 525 during manufacture or use applications. Preferably, card 525 includes a bounded opening or slot 528 that is approximately 0.25 inches to approximately 0.75 inches in height and sufficiently wide to span the full width of tongue member 505 and the connection with fracture member 506 so as to position itself as shown generally in FIG. 39.

As an adaptive embodiment the fluid exiting slot on the inferior side of the sponge extends almost the full width of card 525 for a speedy delivery of fluid while protecting the superior side of the sponge from unintended fluid dispersal or pooling. As noted earlier, during surgical preparation a sterile prep item may not be used again on the same patient following an initial removal as a consequence, the present embodiment minimizes loss or waste by preserving a second foam side or superior foam side for second use by the same applicator. As a consequence, as noted in FIG. 39 fluid flow is to the inferior portion of the sponge and directly applies to the contact surface and flows between the contact surface 511 and the surface of card 525 for distribution without penetrating card 525 to translate to the superior portion of the sponge. This action retains the superior side of the sponge in a substantially or completely dry condition for later sterile use (which may be achieved by merely flipping the applicator over to the superior side and proceeding as discussed above and demonstrated in the figures.

Another alternative embodiment of the dispensing applicator in accordance with the present invention is depicted in FIGS. 41-46. With reference thereto, FIGS. 41A-C show different views of the alternative embodiment of a mounting block 550 for a fluid dispensing applicator according to the invention which receives an absorbent applicator 548 at a block bottom side 552. In particular, as shown, the dispensing applicator comprises a mounting block 550 having a bottom or base piece 552, a bottom side skirt part to which is affixed an absorbent sponge type applicator (see FIG. 43), and a stem piece 554 upstanding from base piece 552. An absorbent swab may optionally be carried at an adjacent side of the mounting block 550 (see FIGS. 5A-B, 11A-B and 12-13), for which purpose the mounting block 550 includes a mounting bracket (e.g., similar to that shown in FIG. 18) receptive of a skirt piece to which the absorbent swab is affixed. Optionally, mounting block 550 may include projections 558 to aid in rotating mounting block 550 about the axis of stem piece 554 as indicated by arrow 556 to cause fracture of tongue 570 and fracture member 564 while tongue 570 is positioned within fracture anvil 560 (see FIG. 41C). Stem piece 554 is preferably a tubular component and its interior space is in communication with the interior space of base piece 552 (see FIG. 41B), which outlets to absorbent applicator 548 so that a flow course in the mounting block 550 has an inlet in the stem piece 554 and outlet at applicator 548. An elongated fluid container 574 (see FIG. 43) is attachable to the mounting block 550 with an end of the fluid container 574 being received in stem piece 554.

Referring in more detail to FIGS. 41A-C and 43-46, fluid container 574 which is preferably of a tubular configuration is capped at a first end 576 with and end cap assembly, which preferably comprises cap 584, thin film or gasket 582, and flange 578 preferably having an opening 580 therein. At a distal opposite end length, an attachment member 568 has a length portion received inside the fluid container 574, and the length portion being affixed to the fluid container 574 as, for example, by heat sealing or snap fit. The length portion optionally has a flange 572 thereon and a continuing length portion constituting a frangible section 564, which transitions into a tongue element 570. The juncture of the tongue element 570 and the continuing length portion 564 defines a weakened joinder location at which the fracture and partial separation of the tongue element 570 from the frangible section 564 will occur, enabling the outlet or flow of fluid from fluid container 574 into the interior space of the mounting block 550 and base piece 552.

Figure 42A:
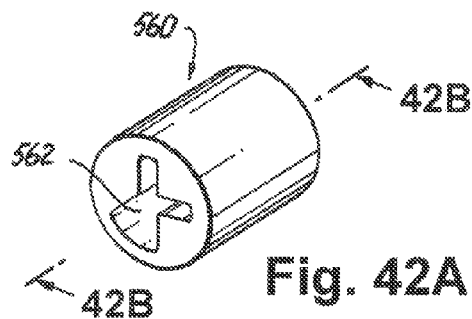
FIG. 42A is a perspective view of an alternate embodiment of a fracture anvil for being removably inserted in an applicator mounting block part of the applicator head, the fracture anvil having a partial cruciform, partial semi-circular passage for reception of the fluid source container tongue element, the fracture anvil being employed to effect partial fracture of the frangible region-tongue element joinder on a relative rotatable movement between said container and said fracture anvil.
Figure 42B:
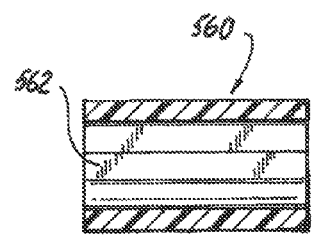
FIG. 42B is a cross-section view of the fracture anvil taken along the line 42B-42B in FIG. 42A.

Referring now to FIGS. 42A-B, shown is a perspective view of an alternate embodiment of a fracture anvil 560 for being removably inserted in an applicator mounting block 550 of the applicator head, the fracture anvil 560 having a partial cruciform, partial semi-circular passage 562 for reception of the fluid source container tongue element 570, the fracture anvil 560 being employed to effect partial fracture of the frangible region 564 and tongue element 570 joinder on a relative rotatable movement between the fluid container 574 and the fracture anvil 560. FIG. 42B shows a cross-section view of the fracture anvil 560 taken on the line 42B-42B of FIG. 42A showing that passage 562 preferably extends the full length of fracture anvil 560. Referring still to FIGS. 42A-B, depicted is yet another embodiment of a fracture anvil 560 for use with the dispensing applicator according to the invention. The fracture anvil 560 shown has a partial cruciform, partial semi-circular passage 562 extending therethrough, as well as a number of extension fluid pass-through passages for enabling fluid released upon fracture of the tongue 570 and flow toward absorbent applicator 548.

When the second opposite end of the container 574 is inserted into the stem piece 554, the tongue element 570 is aligned such that it will enter and locate in the vertical cross passage part of partial cruciform, partial semi-circular passage 562, the fracture anvil 560 having been inserted in the bore of the stem piece 554. The second opposite end of the container 574 is snap fit connected to the stem piece 554. The arrangement is such that with flange 572 received is annular internal groove in the stem piece 554 (see e.g., FIG. 21), the tongue element 570 is properly positioned in the vertical cross passage 562 part for effecting fracture thereof. External dimensioning of the annular flange and internal groove is such that the container 574 can be rotated relative to the fracture anvil 560 while the fracture anvil 560 is held in position. This approximately forty-five degree rotation (or even thirty to sixty degree rotation) of the container 574 is effective to twist part of the tongue element 570 at the weakened joinder location, fracturing a portion of the tongue 570 and effecting at least partial separation from fracture member 564 and thus attachment member 568. With this fracture, fluid releases from the container 574 into the mounting block 550 through course and to the absorbent applicator 548.

Referring specifically to FIG. 43, shown is an exploded left front side perspective view of still another embodiment of a dispensing applicator according to the invention wherein a fluid containing source 574 is receivably attachable to an applicator mounting body stem piece 554 in snap fit connection therewith. Initiation of fluid flow is then effectuated with a relative rotative movement, as indicated by arrow 556, between the fluid source container 574 and a fracture anvil 560 (see FIG. 44) in the stem piece 554 of mounting block 550. The first end 576 of fluid container 574 has a central opening or bore therethrough. A capping assembly (i.e., flange 578, foil gasket 580 and end cap 584) is releasably attached to the opening at end 576. The capping assembly preferably includes, e.g., foil material gasket 582 constructed from a suitable material which is used to intervene the inner side of the closure cap 584 and the annular flange 578. The annular flange 578 preferably has a bore or opening 580 therethrough for the ease in refilling the fluid container 574 with fluid without having to remove the flange from the end 576 of the fluid container 574. Gasket 582 is preferably set on top of the outer face of flange 578, the gasket preferably being of larger area expanse than flange 578 to make liquid contact and provide sufficient lateral sealing. Further, gasket 582 is preferably selected from materials which are liquid proof, stretchable or deformable to a certain degree so that when closure cap 584 is fitted over the first end 576 of the fluid container 574 sandwiched between the inner face of the closure cap 584 and the outer face of the flange 578, an air tight joint seal of the fluid container 574 is effected without forming a bubble, since the gasket material will preferably conform to the sandwiching structure in intimate contact therewith. As seen in FIG. 44, which is a cross-section view taken on the line 44-44 in FIG. 43 showing relative position of the tongue member 563 within the partial cruciform, partial semi-circular passage 562 of the fracture anvil 560, the fracture anvil 560 may have a number of fluid pass-through passages 561 for enabling additional fluid release upon fracture of the tongue 570 so as to flow toward absorbent applicator 548 on the base piece 552.

Figures 45, 46:
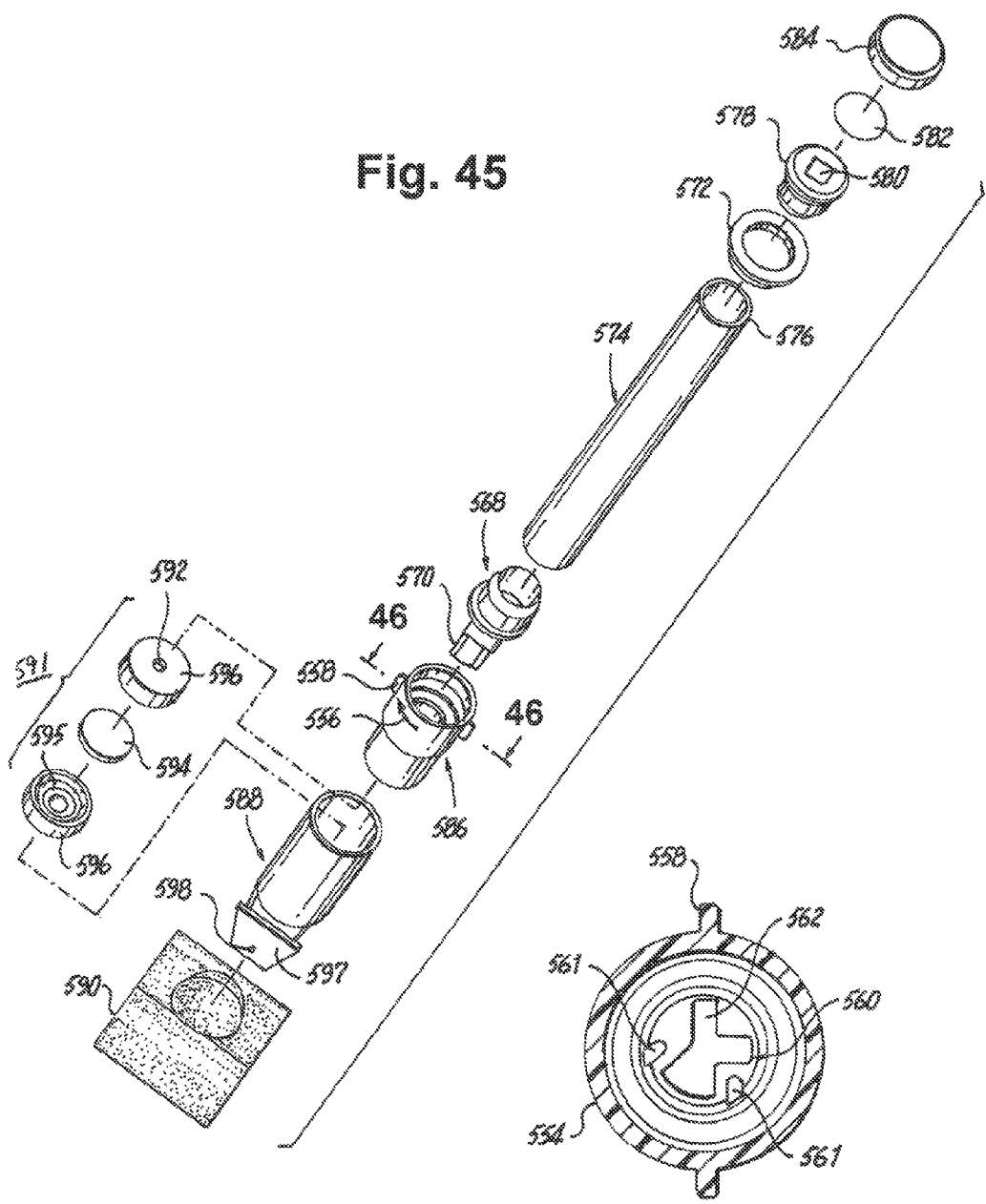
FIG. 45 is an exploded left bottom side perspective view of still another embodiment of a dispensing applicator wherein a fluid containing source is receivably attachable to an applicator mounting body stem piece in snap fit connection therewith, initiation of fluid flow being effected with a relative rotational movement between the fluid source container and a fracture anvil in the mounting body, and further showing a dye packet assembly having top and bottom diffusers and a dye tablet.
FIG. 46 is a cross-section view taken along the line 46-46 in FIG. 45 showing the partial cruciform, partial semi-circular passage of the fracture anvil therein.

Referring next to FIG. 45, shown is an exploded left front side perspective view of still another embodiment of a dispensing applicator according to the invention wherein a fluid containing source 574 is receivably attachable to an applicator mounting body 588 in snap fit connection therewith. Preferably, initiation of fluid flow is effected with a relative rotative movement 556 between the fluid source container 574 and a fracture anvil 560 (see FIG. 46) in the mounting body 588, and further showing a dye packet assembly 591 having top and bottom diffusers 596 each preferably with a spiral-like pathway 595 leading to openings 592 (for passage of the fluid) and a dye tablet 594. The embodiment of the dispensing applicator of FIG. 5 is similar with the applicator shown in FIG. 43 except wherein dye packet assembly 591 is provided in the mounting body 588.

Figure 47:
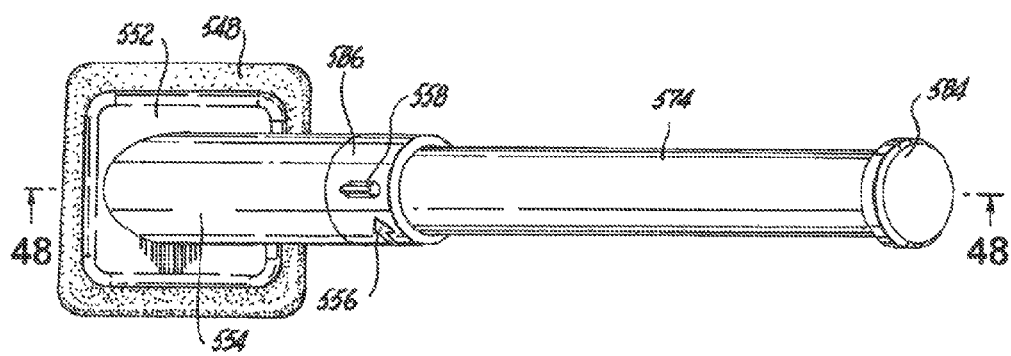
FIG. 47 is a top plan view of the assembled dispensing applicator shown in FIG. 45.
Figure 48:
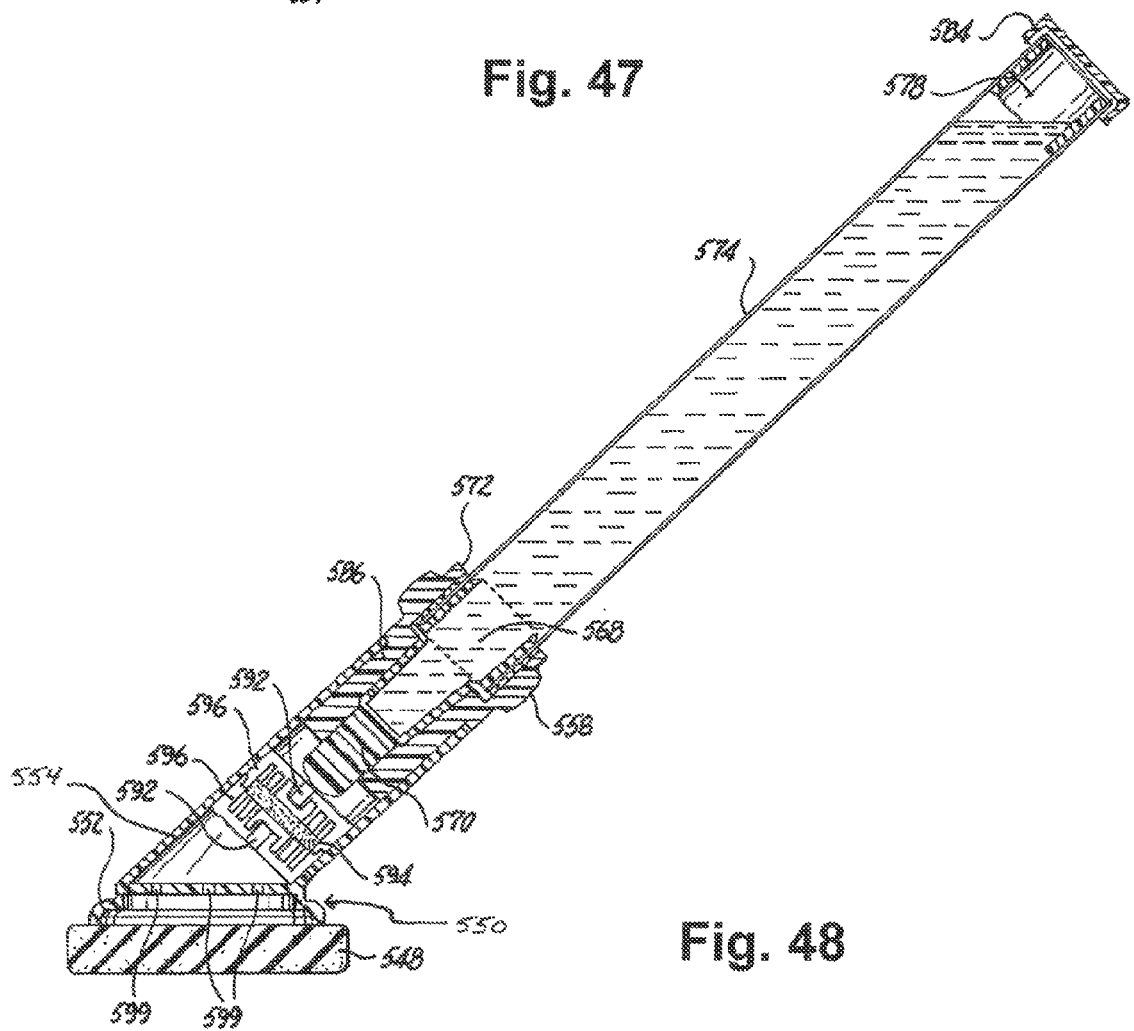
FIG. 48 is a cross-section view of the assembled fluid dispensing applicator taken along the line 48-48 in FIG. 47.

Turning to FIG. 46, shown is a cross-section view taken along the line 46-46 of the applicator of FIG. 45 showing the partial cruciform, partial semi-circular passage 562 of the fracture anvil 560. When assembled, as shown in FIG. 47, the assembled dispensing applicator of FIG. 45 is closed at one end with cap 584 and at the other end with the removable attachment of fluid source 574 into mounting block 550 through rotatable connector 586. As can be seen in FIG. 48, which shows a cross-section view of the assembled fluid dispensing applicator taken along the line 48-48 in FIG. 47, dispensing applicator comprises a mounting block 550 having a base piece 552 with an opening or plurality of openings 599 for passage of the fluid, a bottom side skirt part to which is affixed an absorbent sponge 548 and a stem piece 554. Optionally, (not shown here, but generally depicted in FIG. 12), an absorbent swab may be carried at an adjacent side of the mounting block, for which purpose the mounting block 550 includes a mounting bracket (depicted to advantage in FIG. 18) receptive of a skirt piece to which swab is affixed. Stem piece 554 is preferably a tubular component and its interior space is in communication with the interior space of base piece 552, which outlets to absorbent applicator 548 so that a flow course in the mounting block 550 has inlet in the stem piece 554 and outlet at absorbent applicator 548. The elongated fluid container 574 is attachable to the mounting block 550, an end of the container 574 being received in stem piece 554.

Figure 49A:
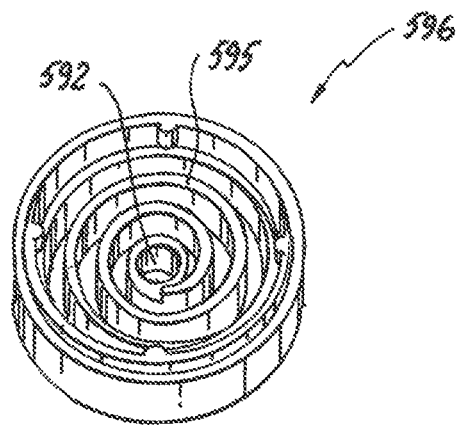
FIG. 49A is a top perspective view of a preferred embodiment of a diffuser element for the dye packet assembly showing the internal configuration thereof.
Figure 49B:
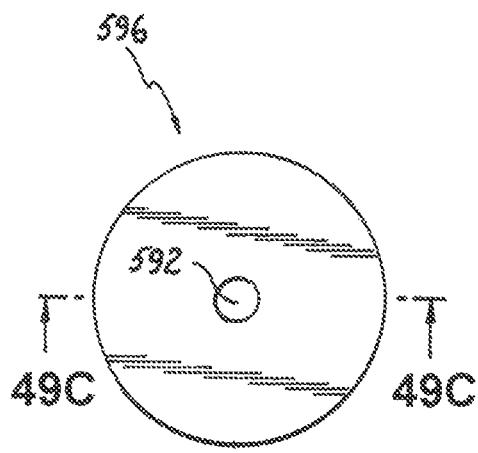
FIG. 49B is a bottom plan view of the diffuser element shown in FIG. 49A.
Figure 49C:
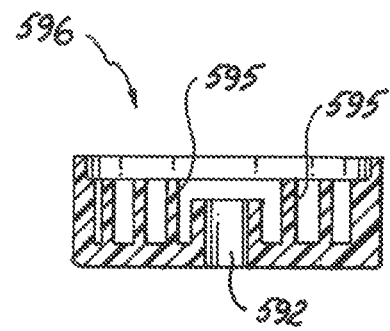
FIG. 49C is a cross-section view of the diffuser element taken along the line 49C-49C in FIG. 49B.

Referring next to FIGS. 49A-C, shown are, respectively, enlarged perspective, bottom and cross-section (taken along line 49C-49C of FIG. 49B) views of a preferred embodiment of a diffuser element 596 for the dye packet assembly 591. Preferably, assembly 591 has upper and lower diffusing elements 596 between which a compressed or impregnated dye tablet or disc 594 is positioned (see, e.g., FIG. 53). Each element 596 is preferably formed with an inner wall 595 preferably shaped or configured in a spiral configuration. As fluid flows into the assembly 591 through an opening 592 in the upper element 596 the fluid interacts with the packet, tablet or disc 594 to dissolve the disc into the fluid. Dye tablet or disc 594 is preferably a color dye to color the fluid so the doctor can see where the fluid (e.g., antiseptic) has been applied, but the tablet 594 may be any other necessary compound to be mixed with the fluid. After mixing of the fluid and the tablet 594, the colored fluid mixture flows through the spiral cavity of the lower element 596 out of the assembly 591 through a second opening 592 (or plurality of openings) in the lower element 596 such that it may flow toward dispensing head 600. Preferably, inner spiral wall 595 configured in each of the upper and lower elements 596 controls the speed and direction of the flow of the fluid mixture through assembly 591 from the source 606 to the dispensing head 600.

Figure 52:
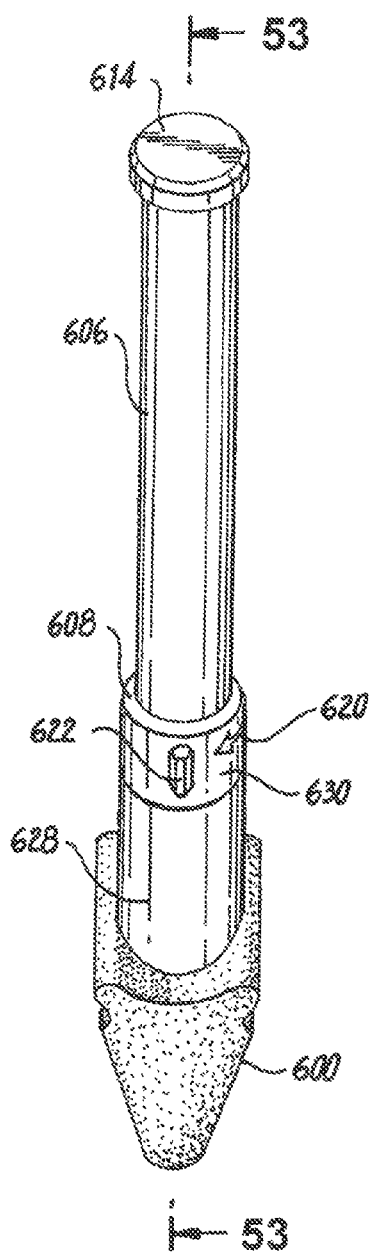
FIG. 52 is a side perspective view of the assembled dispensing applicator shown in FIG. 50.
Figure 53:
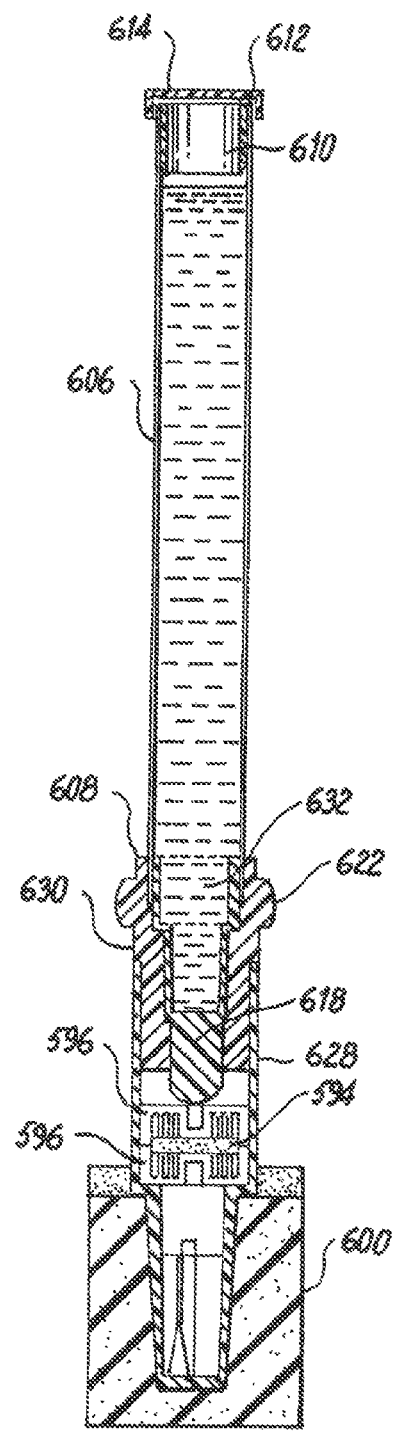
FIG. 53 is a cross-section view of the assembled fluid dispensing applicator taken along the line 53-53 in FIG. 52.

Turning next to FIGS. 50-53, shown are an exploded left front side perspective view and a cross-sectional view (taken along line 51-51 in FIG. 50), respectively, of still another embodiment of a dispensing applicator according to the invention wherein a fluid containing source 606 is receivably attachable to an applicator mounting body stem piece 604 in snap fit connection therewith. Initiation of fluid flow is effected with a relative rotative movement of mounting block 602 using, e.g., projection 622 (as indicated by arrow 620) between the fluid source container 606 and a fracture anvil 631 in the mounting body. Upon fracture of the tongue 618 from interaction with the fracture anvil 631, fluid is released from the source 606 through openings at the juncture of tongue 618 and stem piece 604 to allow fluid to flow into the inner cavity of the mounting block 602. From there, the fluid flows through opening 624 in the mounting block base plate 626 into or onto the dispensing head or sponge 600 for application to the desired surface. As seen in FIGS. 52-53, depicted are a side perspective view and a cross-section view taken along line 53-53 in FIG. 52, respectively, of the assembled fluid dispensing applicator shown in FIG. 50. Optionally, as seen in FIG. 53, a dye pack assembly 591 comprising upper and lower diffusing elements 596 between which a diffusing packet or disc 594 is positioned (see, e.g., FIG. 53) may be employed.

A capping assembly (i.e., flange 610, foil gasket 612 and end cap 614) is releasably attached to the opening. The capping assembly preferably includes, e.g., foil material gasket 612 constructed from a suitable material which is used to intervene the inner side of the closure cap 614 and the annular flange 610. A secondary flange 608 may optionally be used to provide added seal between the cap assembly and the container 606. The annular flange 610 preferably has a bore or opening 616 therethrough for the ease in refilling the fluid container 606 with fluid without having to remove the flange from the end of the fluid container 606. Gasket 612 is preferably set on top of the outer face of flange 610, the gasket 612 preferably being of larger area expanse than flange 610 to make liquid contact and provide sufficient lateral sealing. Further, gasket 612 is preferably selected from materials which are liquid proof, stretchable or deformable to a certain degree so that when closure cap 614 is fitted over the first end of the fluid container 606 sandwiched between the inner face of the closure cap 614 and the outer face of the flange 610, an air tight joint seal of the fluid container 606 is effected without forming a bubble, since the gasket material will preferably conform to the sandwiching structure in intimate contact therewith.

Figure 54C:
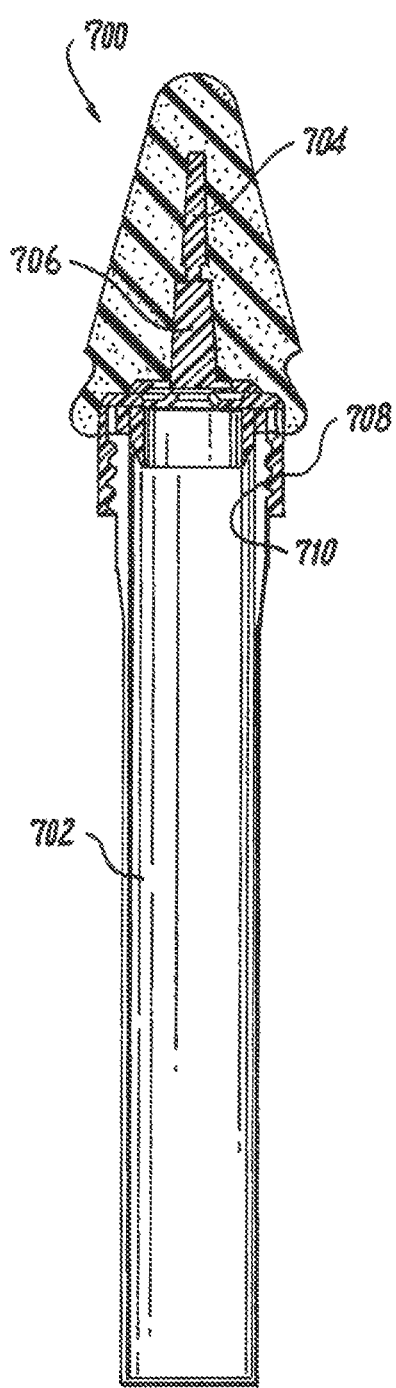
FIG. 54C is a side cross-section view of the assembled dispensing applicator of FIG. 54A taken along the line 54C-54C.
Figure 54D:
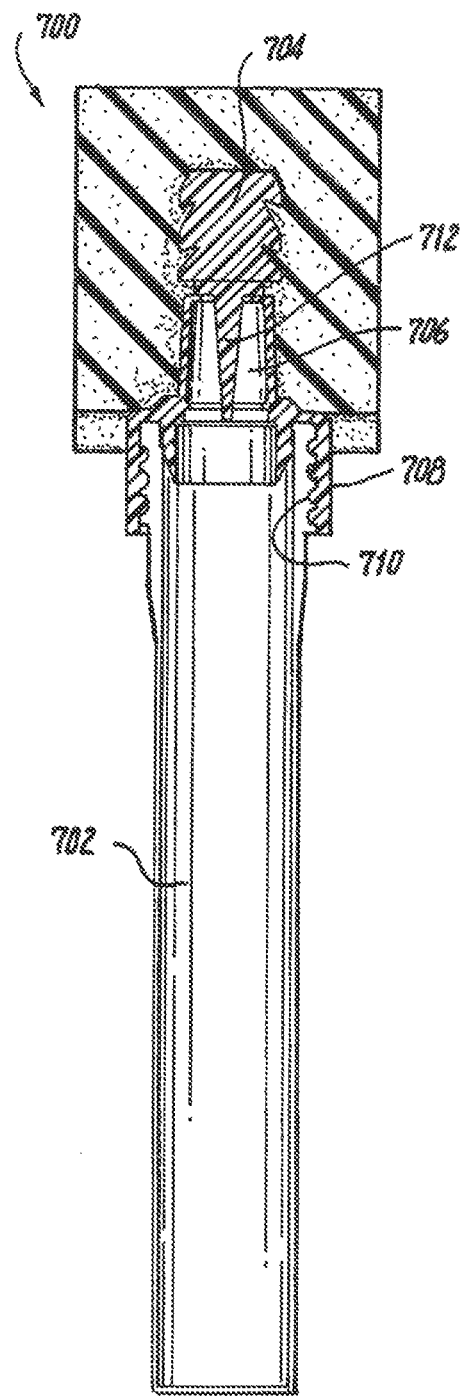
FIG. 54D is a front cross-section view of the assembled dispensing applicator of FIG. 54A taken along the line 54D-54D.

Turning now to FIGS. 54A-D, shown is still another alternative embodiment of an assembled dispensing applicator 701 wherein a fluid containing source 702 is receivably attachable to an applicator mounting body stem piece 714 in snap fit connection therewith. Preferably, initiation of fluid flow is effected with a relative downward movement between the fluid source container 702 and a fracture member 706 connected with the mounting body stem piece 714 such that a tongue member 704 snaps or fractures to allow fluid to flow therethrough. FIG. 54B shows an exploded left front side perspective view of the dispensing applicator shown in FIG. 54A wherein a fluid containing source 702 is receivably attachable to an applicator mounting body stem piece 714 in snap fit connection therewith. A securing ring or gasket 708 may be provided to secure stem piece 714 into or with source 702. Preferably tongue 704 has ribbed or jagged sides to engage with an inner surface of the sponge applicator 700 to secure it in place on the dispensing applicator. Looking at FIG. 54C, shown is a side cross-section view of the assembled dispensing applicator of FIG. 54A taken on the line 54C-54C, while FIG. 54D shows a front cross-section view of the assembled dispensing applicator of FIG. 54A taken on the line 54D-54D, both showing the internal connections and interfacing of the various components thereof.

Figure 55:
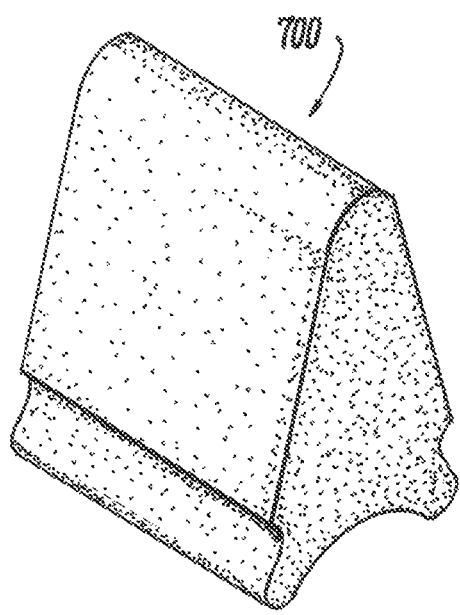
FIG. 55 is an elevated perspective view of an embodiment of a fluid dispersing head for use with the fluid dispensing applicator according to an alternative embodiment of the invention.
Figure 56A:
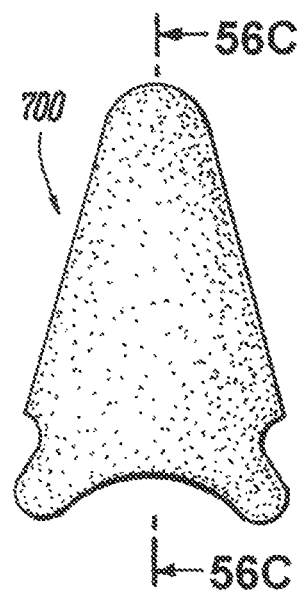
FIG. 56A is a side view of the fluid dispersing head of FIG. 55.
Figure 56B:
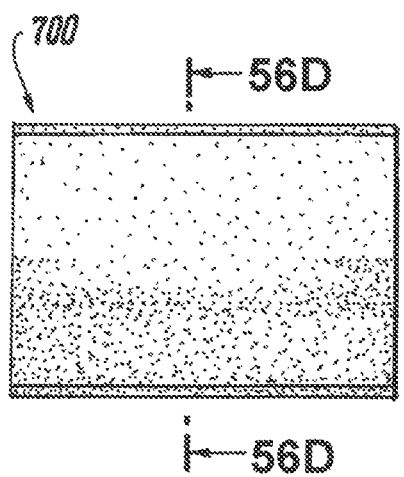
FIG. 56B is a top plan view of the fluid dispersing head of FIG. 55.
Figure 56C:
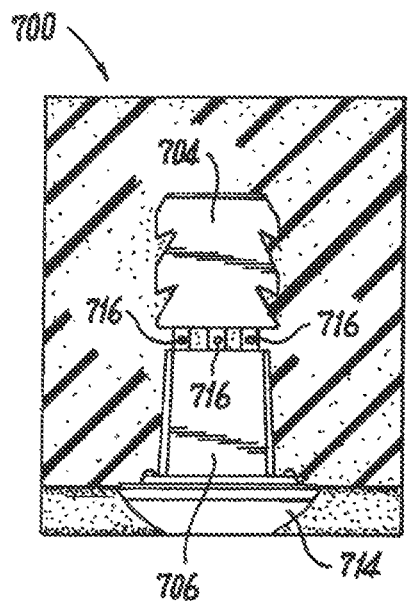
FIG. 56C is a front cross-section view of the fluid dispersing head of FIG. 55 taken along the line 56C-56C in FIG. 56A further showing the relative position of an applicator tip member and fracture member within the fluid dispersing head.
Figure 56D:
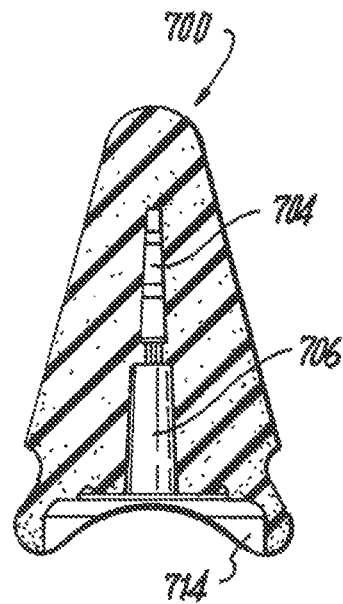
FIG. 56D is a left side cross-section view of the fluid dispersing head of FIG. 55 taken along the line 56D-56D in FIG. 56B further showing the relative position of an applicator tip member and fracture member within the fluid dispersing head.
Figure 57:
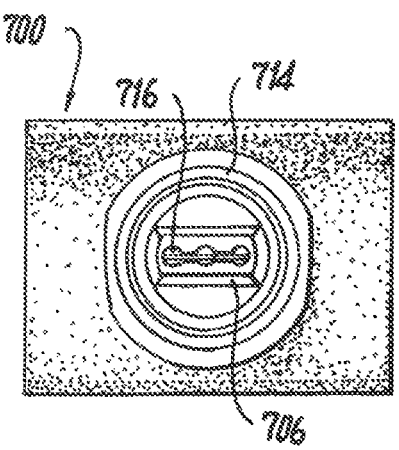
FIG. 57 is a bottom view of the fluid dispersing head of FIG. 55.

FIGS. 55-57 depict various views of an embodiment of a fluid dispersing head 700 for use with the fluid dispensing applicator according to the invention. In particular, FIGS. 56C-D and FIG. 57, which are cross-sectional views of the fluid dispersing head of FIG. 55 taken on the line 56C-56C in FIG. 56A and line 56D-56D in FIG. 56B, further show the relative position of an applicator tip member or tongue 704, stem piece 714, and fracture member 706 within the fluid dispersing head 700. Also a plurality of openings 716 within the interface between tongue 704 and fracture member 706 may be provided to allow fluid flow therethrough upon fracture.

Figure 50:
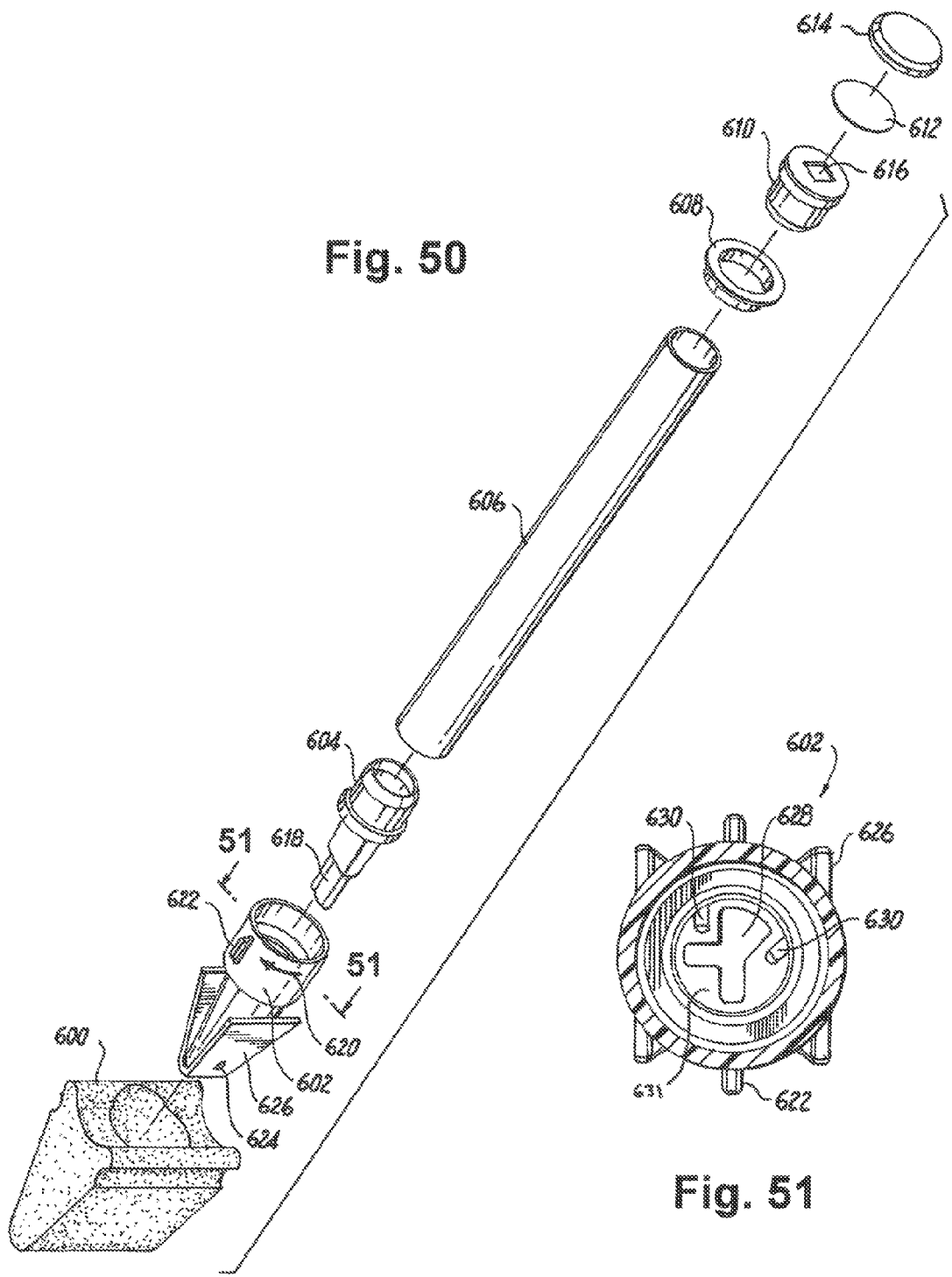
FIG. 50 is an exploded left front side perspective view of still another embodiment of a dispensing applicator wherein a fluid containing source is receivably attachable to an applicator mounting body stem piece in snap fit connection therewith, initiation of fluid flow being effected with a relative rotational movement between the fluid source container and a fracture anvil in the mounting body.
Figure 51:
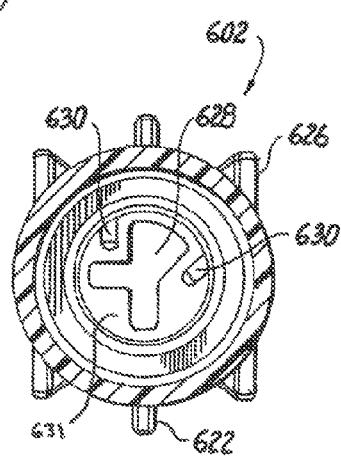
FIG. 51 is a cross-section view taken on the line 51-51 in FIG. 50 showing the partial cruciform, partial semi-circular passage of the fracture anvil.
Figure 58A:
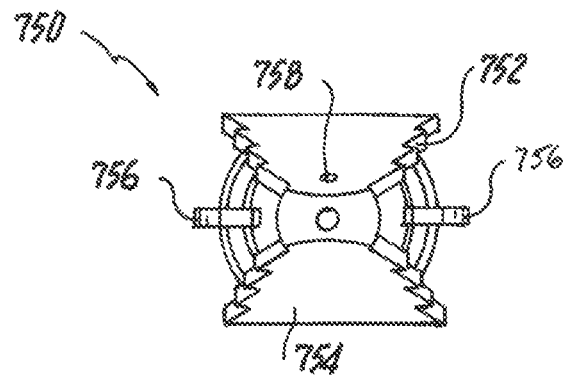
FIG. 58A is a top end plan view of an alternative embodiment of an applicator mounting block according to the invention having an opening on one side for the dispersing of fluid to only one side of a fluid dispensing head.
Figure 58B:
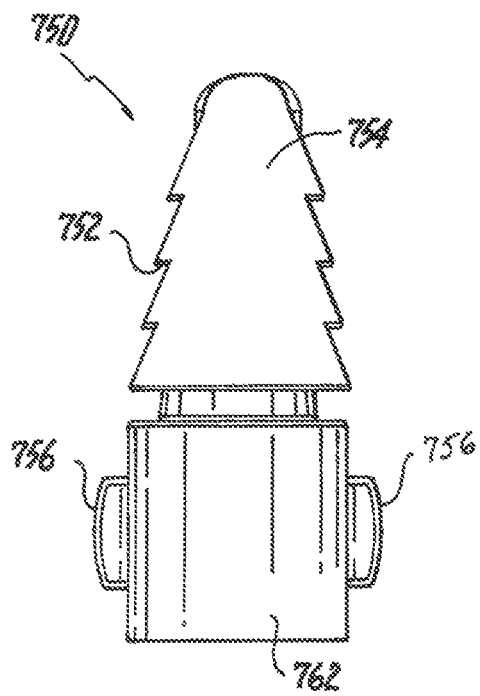
FIG. 58B is a first side view of the applicator mounting block of FIG. 58A showing no opening for dispersing fluid to the fluid dispersing head.
Figure 58C:
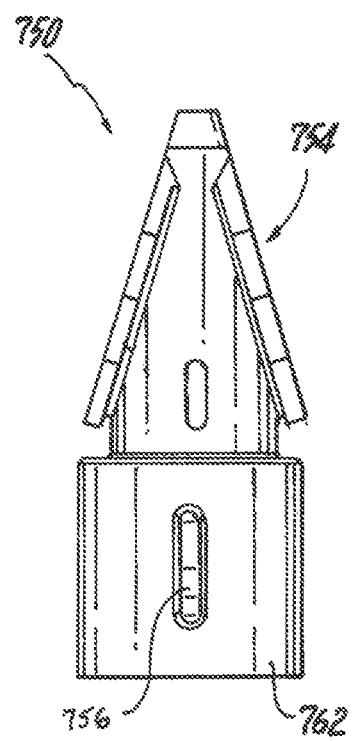
FIG. 58C is a second side view of the applicator mounting block of FIG. 58A.
Figure 58D:
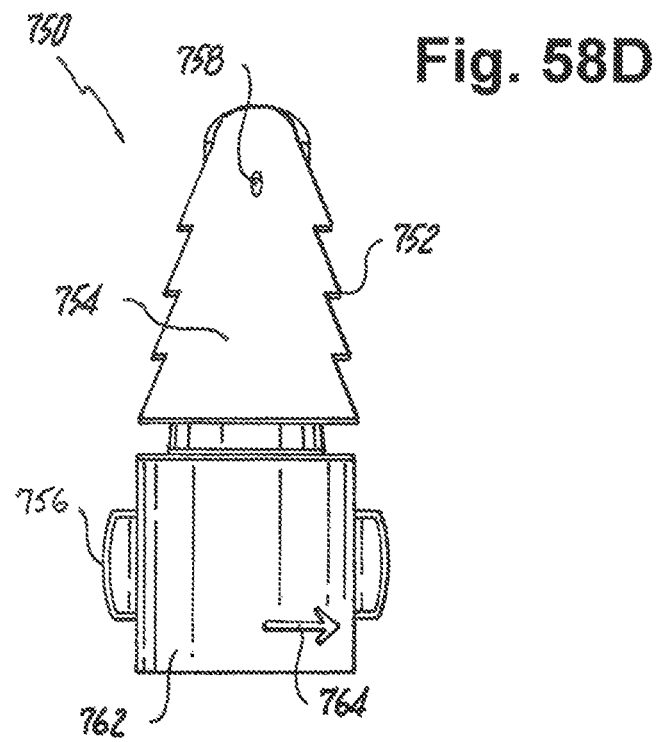
FIG. 58D is a third side view of the applicator mounting block of FIG. 58A showing the opening for dispersing of fluid to the fluid dispersing head.
Figure 58E:
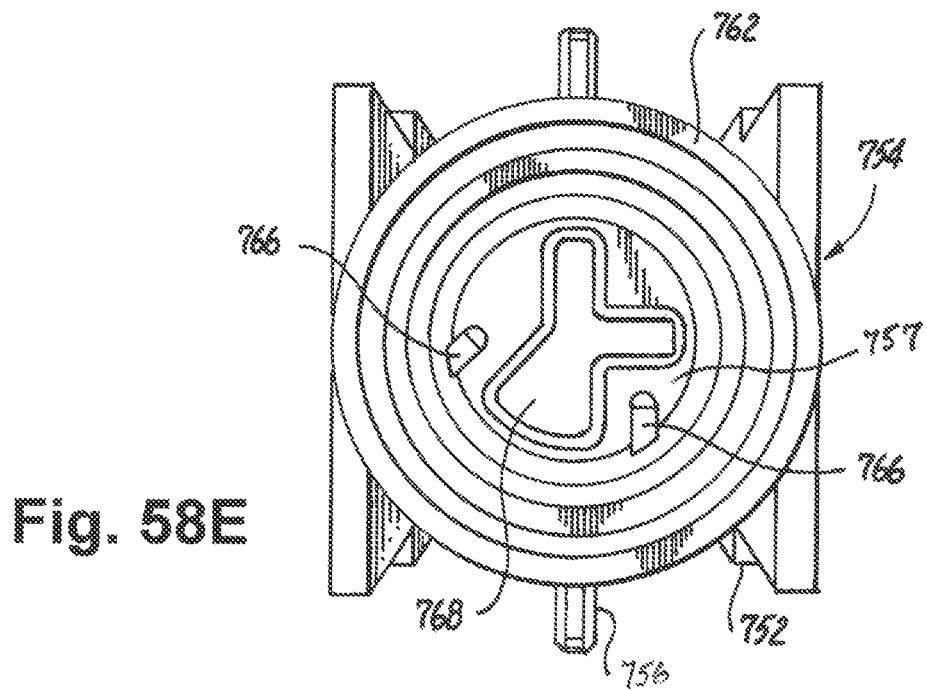
FIG. 58E is a bottom end view of the applicator mounting block of FIGS. 58A-D showing the partial cruciform, partial semi-circular passage of the fracture anvil.

Next, FIGS. 58A-E depict various views of an alternative embodiment of an applicator mounting block 750 according to the invention having an opening 758 (e.g., a plurality of openings may also be employed) on one side for the dispersing of fluid to only one side of a fluid dispensing head (see, e.g., FIG. 50). That is, FIG. 58B shows no opening 758 on base plate 754 of the mounting block 750 for dispersing fluid to the fluid dispersing head, while FIG. 58D, showing another side of the applicator mounting block 750, does depict an opening 758 for dispersing fluid to the fluid dispersing head. Of course, the opening 758 could be positioned on either or even both base plates 754 of the mounting block 750 of the applicator head. Additionally, mounting block 750 has a generally circular stem piece 762 extending at one end, with the stem piece 762 having one or more projections 756 used for rotating the stem piece 762, as indicated by arrow 764 in FIG. 58D, with respect to the fluid source handle (see e.g., FIG. 50) to effectuate fracture of the tongue element within the inner cavity of the mounting block 750 to allow the flow of fluid therethrough. As seen in FIGS. 58A-E the base plates 754 preferably comprise jagged or teeth-like side edges 752 design to engage an inner cavity or surface of an applicator sponge head to hold it in position without any additional adhesive. Referring to FIG. 58E, shown is a bottom end view of the applicator mounting block 750 of FIGS. 58A-D, which depicts the inclusion of a partial cruciform, partial semi-circular fracture anvil 757 discussed in detail above. Initiation of fluid flow is effected with a relative rotative movement of mounting block 750 using, e.g., projection 756 (as indicated by arrow 764 in FIG. 58D) between the fluid source container and a fracture anvil 757 in the mounting body. Upon fracture of the tongue from interaction with the fracture anvil 757, fluid is released from the source through openings at the juncture of tongue and stem piece 762 to allow fluid to flow into the inner cavity of the mounting block 750. From there, the fluid flows through opening 758 in the mounting block base plate 754 into or onto the dispensing head or sponge for application to the desired surface.

Turning next to FIGS. 59-65 shown is a dispensing applicator 803 according to another alternate embodiment of the present invention. As seen first in FIGS. 59-60, dispensing applicator 803 is preferably a single, unitary structure formed, for example, by injection molding or other known process. The unitary dispensing applicator 803 preferably comprises, in general, a fluid containing source region 814, end cap region 822, fracture member region 806, and tongue element 804 all integrally formed. Preferably, tongue element 804 and fracture member region 806 further comprise wings or fins 812 to engage an inner surface or cavity of the applicator sponge 800 without need for additional adhesive.

Optionally, tongue 840 may also comprise outer ribs 808 and/or inner rib 810 for added strength and support to prevent inadvertent or premature fracture of the tongue element 804. To close the end cap region 822 of the fluid source region 814, an end cap 820 is provided which preferably is snap-fit onto the end cap region 822, but may also be screwed on or attached by other known securing methods or devices. Also, fluid source region 814 may also be configured with an indented gripping region 816 configured along the length region the fluid source region in such a manner that is substantially parallel with the plane of the tongue element 804. Also, more than one such gripping region 816 may be provided.

According to this embodiment, initiation of fluid flow is effected with a relative downward movement between the fluid source region 814 and a fracture member region 806 such that a tongue member 804 snaps or fractures to allow fluid to flow therethrough. Preferably an interface 815 (see FIGS. 61-62) between fracture member region 806 and fluid source region 814 is configured with thicknesses sufficiently stronger than the interface or frangible region 824 (see FIG. 63) between the tongue element 804 and the fracture member region 806. As seen in FIG. 60, showing an exploded left front side perspective view of the dispensing applicator shown in FIG. 59, the fluid containing source region 814 is integrally connected with the fracture member region 806 and tongue element 804. Preferably tongue 804 and fracture member region 806 have wings or fins 812 to engage with an inner surface of the sponge applicator 800 to secure it in place.

As specifically seen in FIG. 63, which shows a front cross-sectional view of the dispensing applicator shown in FIG. 61 taken along line 63-63, fluid source region 814 comprises inner cavity 826 for housing the desired fluid (e.g., antiseptic) and fracture member region 806 comprises an inner cavity 807 to allow the flow of fluid therethrough. Preferably, a juncture between inner cavity 826 and inner cavity 807 is tapered such that there is a tapered region 828 where the diameter of the inner cavity reduces in size when proceeding from the fluid source region 814 toward the fracture member region 806. Such tapering allows for increased thickness and strength at the interface 815 between the source region and fracture member region 806. As shown in FIGS. 64-65, fracture member region 806 may be directly connected to an end of the source region 814 such that no "taper" region 828 is needed. In this embodiment, inner cavity 826 of source 814 leads directly into inner cavity 807 of fracture member region 806, which itself maybe but is not necessarily, tapered as shown. Such an embodiment also provides still further increased strength at the interface 815 between the source region 814 and the fracture member region 806.

Turning lastly to FIGS. 66-68, illustrated are further alternative embodiments of the applicator heads having different tongues or fins 804 (FIG. 66), 809/811 (FIG. 67), and 813/815 (FIG. 68), each in accordance with the present invention. First, FIGS. 66A-B show a partial perspective view of a second alternative applicator head fin 804. In this embodiment, tongue 804 is the same as shown and described above regarding FIGS. 59-65. Lower fin 812, however, is not present. Fins of tongue 804 are sufficient to engage with and hold sponge applicator head 800 in place during use. Second, FIGS. 67A-B show a partial perspective view of a third alternative set of applicator head tongue 809 and fins 811. As compared to FIGS. 59-66, the tongue and fins 809, 811 of this alternate configuration generally comprise an arced or semi-circular design or configuration. Third, FIGS. 68A-B show a partial perspective view of a fourth alternative set of applicator head fins 813, 815. As compared to FIGS. 59-67, the tongue and fins 813, 815 of this alternate configuration generally comprise a somewhat square-shaped tongue element 813 with a plurality of curved lower fins 815 on either side of the fracture member region 806. While two such fins 815 are depicted on each side of fracture member region 806, only one or even more than two such fins 815 may be used. Of course, other shapes, sizes, configurations, etc. of the fins and/or tongue elements may be used without departing from the spirit of the invention.

While the present invention is primarily directed to a dispensing applicator for the application of liquids to the surface of the head, limbs, and/or body for medical purposes (i.e., pre-surgical disinfection), dispensing applicators according to the present invention may be used in a wide variety of purposes and environments. For example, a dispensing applicator according to the present invention can be used for application of lubricant(s) or adhesive(s). The range of sizes can also vary widely, as long as the several wall thicknesses are controlled appropriately to afford the desired functional characteristics discussed herein. It should also be appreciated by those of skill in the art that the fluid reservoirs, in selected embodiments, are flexibly bounded and allow an operator to control volumetric application based on the amount of pressure applied to the exterior of the reservoir. As a consequence of this design, it should also be recognized by those of skill in the art, that an operator releasing a compressed reservoirs, may partially suction released fluid back into the reservoir and minimize pooling.

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings sufficient to enable one of ordinary skill in the art to practice the invention, and to provide the best mode of practicing the invention presently contemplated by the inventor, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. Accordingly, the disclosed embodiments are not mutually exclusive combinations of features; rather, the invention may comprise a combination of different individual features selected from different individual embodiments, as understood by persons of ordinary skill in the art. The scope of the invention, therefore, shall be defined solely by the appended claims.

Further, while there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A dispensing applicator comprising a frangible applicator tip, said applicator comprising:
    a substantially rigid unitary body having a substantially cylindrical fluid source region, a fracture member region, and a substantially rigid tongue element, said tongue element extending outwardly from said fracture member region, and wherein said tongue element has a central portion and at least two side portions;
    an applicator head comprising a generally triangular cross-section base provided with an inner cavity for receiving at least said tongue element; and
    a frangible region defined as a region at the juncture of said fracture member region and said tongue element;
    wherein fracture of said frangible region allows partial fluid release from said fracture member region to said applicator head,
    wherein said tongue element is provided with one or more reinforcing ribs extending from said fracture member region across said frangible region.

2. The dispensing applicator according to claim 1, wherein said side portions of said tongue element extend outwardly so as to engage with said inner cavity of said applicator head.

3. The dispensing applicator according to claim 1, wherein said one or more reinforcing ribs are configured to resist deflection of said tongue.

4. The dispensing applicator according to claim 3, wherein said one or more ribs are non-uniformly dimensioned and have at least two relatively long ribs disposed along each side edge and at least one pair of relatively short ribs flanking the central portion.

5. The dispensing applicator according to claim 1, wherein said substantially cylindrical fluid source region is open at one end, wherein an end cap is positioned thereon to close said open end.

6. The dispensing applicator according to claim 5, wherein said end cap is snap-fit onto said open end.

7. The dispensing applicator according to claim 5, wherein said end cap is screwed onto said open end.

8. The dispensing applicator according to claim 1, wherein said source region further comprises a grip region on an external surface thereof.

9. The dispensing applicator according to claim 1, wherein a region between said source region and said fracture member region comprises an inner cavity that is tapered in a direction from said source region toward said fracture member region.

10. The dispensing applicator according to claim 1, wherein said tongue element comprises two said side portions, and said fracture member comprises two said side portions.

11. A dispensing applicator comprising:
- a housing body having a central bore therethrough, said housing body comprising a fracture member and an elongated fluid source tube for containing a fluid;
- a substantially rigid tongue element extending outwardly from said fracture member to define an interface therebetween;
- a fluid-absorbent member having a proximal end in flow communication with said fluid source tube, and a distal end for dispersing said fluid; and
- an end cap for closure of an open end of said fluid source tube;
- a frangible region defined as a region at the juncture of said fracture member and said tongue element;
- wherein upon fracture of said frangible region said flow communication is provided between said fluid source tube and said fluid-absorbent member,
- wherein said housing body and said tongue element are configured as a unitary structure, and
- wherein said tongue element is provided with one or more reinforcing ribs extending from said fracture member across said frangible region.

12. The dispensing applicator according to claim 11, wherein said plurality of reinforcing are configured to resist deflection of said tongue, and reduce unintentional breaking of said frangible region.

13. The dispensing applicator according to claim 11, wherein said tongue element is provided with side portions that extend outwardly therefrom to engage with an cavity of said fluid-absorbent member.

14. The dispensing applicator according to claim 11, wherein said end cap is snap-fit onto said open end.

15. The dispensing applicator according to claim 11, wherein said end cap is screwed onto said open end.

16. The dispensing applicator according to claim 11, wherein said fluid-absorbent member is provided with a generally triangular cross-section base provided with an inner cavity for receiving at least said tongue element.

17. The dispensing applicator according to claim 11, wherein said tongue element comprises two side portions, and said fracture member comprises two side portions.

18. The dispensing applicator according to claim 17, wherein said side portions engage with an inner cavity of said fluid-absorbent member.

19. The dispensing applicator according to claim 11, wherein a region between said source tube and said fracture member comprises an inner cavity that is tapered in a direction from said source tube toward said fracture member.

20. The dispensing applicator according to claim 11, wherein said fluid source tube further comprises a grip region on an external surface thereof.

* * * * *